(12) United States Patent
Epple et al.

(10) Patent No.: US 7,820,705 B2
(45) Date of Patent: Oct. 26, 2010

(54) COMPOUNDS AND COMPOSITIONS AS PPAR MODULATORS

(75) Inventors: Robert Epple, San Diego, CA (US); Ross Russo, Encinitas, CA (US); Mihai Azimioara, La Jolla, CA (US); Yongping Xie, San Diego, CA (US)

(73) Assignee: IRM LLC, Hamilton (BM)

( * ) Notice: Subject to any disclaimer, the term of this patent is extended or adjusted under 35 U.S.C. 154(b) by 590 days.

(21) Appl. No.: 11/596,596

(22) PCT Filed: May 12, 2005

(86) PCT No.: PCT/US2005/016672
§ 371 (c)(1),
(2), (4) Date: Oct. 25, 2007

(87) PCT Pub. No.: WO2005/113519
PCT Pub. Date: Dec. 1, 2005

(65) Prior Publication Data
US 2008/0114044 A1 May 15, 2008

Related U.S. Application Data

(60) Provisional application No. 60/571,003, filed on May 14, 2004.

(51) Int. Cl.
*C07D 413/04* (2006.01)
*C07D 261/18* (2006.01)
*A61K 31/4439* (2006.01)
*A61K 31/422* (2006.01)
*A61K 31/42* (2006.01)

(52) U.S. Cl. ............... 514/378; 514/340; 548/248; 546/272.1

(58) Field of Classification Search .......... 548/247, 548/249
See application file for complete search history.

(56) References Cited

U.S. PATENT DOCUMENTS 2,088,996 A * 8/1937 Hoffer .................. 548/248
3,466,296 A 9/1969 Piemmons
3,562,286 A 2/1971 Bramhall et al.
6,005,116 A 12/1999 Kojima et al.
2003/0225158 A1 12/2003 Auerbach et al.

FOREIGN PATENT DOCUMENTS

| DE | 3247454 | 6/1984 |
|---|---|---|
| EP | 0378111 | 7/1990 |
| EP | 0573883 | 12/1993 |
| GB | 1224568 | 5/1971 |
| WO | 0116116 | 3/2001 |
| WO | 2004024939 | 3/2004 |
| WO | 2005033103 | 4/2005 |

OTHER PUBLICATIONS

Golub et al., Science, vol. 286, Oct. 15, 1999, pp. 531-537.*
Selkoe, Physiological Reviews, vol. 81(2), 2001, p. 760.*
Findeis, Pharmacology & Therapeutics 2007, 116, 266-286.*
Epple et al. Bioorganic & Medicinal Chemistry Letters 2006, 16, 4376-4380.*
Epple et al. Bioorganic & Medicinal Chemistry Letters 2006, 16, 5488-5492.*
Yadav, et al., "Zinc Promoted Mild and Efficient Method for the Esterification of Acid Chlorides with Alcohols", Synthetic Communications, 1998, pp. 2337-2342, vol. 28, issue 13.
Yedidia, et al., "Regioselectivity in cycloaddition reactions on solid phases", Can J. Chem., 1980, pp. 1144-1150, vol. 58.
Micetich, "Studies in Isoxazole Chemistry, I. 3- or 5-(5-Nitro-2furyl)-5 or -3-methylisoxazoles", J. Med. Chem., 1969, pp. 611-616, vol. 12, No. 4.

* cited by examiner

*Primary Examiner*—Rebecca L Anderson
*Assistant Examiner*—Matthew P Coughlin
(74) *Attorney, Agent, or Firm*—Scott W. Reid; The Genomics Institute of the Novartis Research Foundation

(57) ABSTRACT

The invention provides compounds, pharmaceutical compositions comprising such compounds and methods of using such compounds to treat or prevent diseases or disorders associated with the activity of the Peroxisome Proliferator-Activated Receptor (PPAR) families, particularly the activity of PPAR.

7 Claims, No Drawings

COMPOUNDS AND COMPOSITIONS AS PPAR MODULATORS

CROSS-REFERENCE TO RELATED APPLICATIONS

This application is a 371 U.S. national phase application of international application number PCT/US2005/016672 filed 12 May 2005, which application claims priority to U.S. Provisional Patent Application No. 60/571,003, filed 14 May 2004. The full disclosure of this application is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of the Peroxisome Proliferator-Activated Receptor (PPAR) families, particularly the activity of PPARδ.

2. Background

Peroxisome Proliferator Activated Receptors (PPARs) are members of the nuclear hormone receptor super family, which are ligand-activated transcription factors regulating gene expression. Certain PPARs are associated with a number of disease states including dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease. Accordingly, molecules that modulate the activity of PPARs, particularly PPARδ, are useful as therapeutic agents in the treatment of such diseases.

SUMMARY OF THE INVENTION

In one aspect, the present invention provides compounds of Formula I:

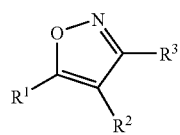

in which:

$R^1$ is selected from $C_{1-6}$alkyl, $C_{3-12}$cycloalkyl, $C_{3-8}$heterocycloalkyl, $C_{6-10}$aryl and $C_{5-10}$heteroaryl; wherein any alkyl, aryl, heteroaryl, cycloalkyl and heterocycloalkyl of $R^1$ is optionally substituted with 1 to 3 radicals independently selected from halo, nitro, cyano, $C_{1-6}$alkyl, $C_{1-6}$alkoxy, halo-substituted-$C_{1-6}$alkyl, halo-substituted-$C_{1-6}$alkoxy, —XC(O)YR$^5$ and —XYC(O)R$^5$; wherein X is a bond or $C_{1-4}$alkylene and Y is selected from a bond, O, S, and NR$^6$; and R$^5$ is selected from $C_{1-6}$alkyl, $C_{3-12}$cycloalkyl, $C_{3-8}$heterocycloalkyl, $C_{6-10}$aryl and $C_{5-10}$heteroaryl; and R$^6$ is selected from hydrogen, $C_{1-6}$alkyl, $C_{3-12}$cycloalkyl, $C_{3-8}$heterocycloalkyl, $C_{6-10}$aryl and $C_{5-10}$heteroaryl;

$R^2$ is selected from —XOXOR$^5$, —XOR$^5$, —C(O)OR$^5$, —C(O)NR$^4$R$^4$, —C(O)NR$^4$XOR$^4$, —C(O)OXOR$^5$, —C(O)XOR$^5$, —C(O)NR$^4$XOR$^5$, —C(O)NR$^4$R$^5$ and —C(O)NR$^4$XR$^5$; wherein X is a bond or $C_{1-4}$alkylene; R$^4$ is selected from hydrogen and $C_{1-6}$alkyl; R$^5$ is selected from $C_{1-6}$alkyl, $C_{3-12}$cycloalkyl, $C_{3-8}$heterocycloalkyl, $C_{6-10}$aryl and $C_{5-10}$heteroaryl; or R$^4$ and R$^5$ together with the nitrogen atom to which R$^4$ and R$^5$ are attached form $C_{3-8}$heterocycloalkyl or $C_{5-10}$heteroaryl;

wherein any alkylene group of R$^2$ is optionally substituted by halo, $C_{1-6}$alkyl and phenyl; wherein any aryl, heteroaryl, cycloalkyl and heterocycloalkyl of R$^2$ is optionally substituted with 1 to 3 radicals independently selected from halo, nitro, cyano, $C_{1-6}$alkyl, $C_{1-6}$alkoxy, halo-substituted-$C_{1-6}$alkyl and halo-substituted-$C_{1-6}$alkoxy;

$R^3$ is selected from $C_{3-12}$cycloalkyl, $C_{3-8}$heterocycloalkyl, $C_{6-10}$aryl and $C_{5-10}$heteroaryl; wherein any aryl, heteroaryl, cycloalkyl and heterocycloalkyl of R$^3$ is optionally substituted with 1 to 3 radicals independently selected from halo, nitro, cyano, $C_{1-6}$alkyl, $C_{1-6}$alkoxy, halo-substituted-$C_{1-6}$alkyl, halo-substituted-$C_{1-6}$alkoxy, —XOXC(O)OR$^5$, —XC(O)OR$^5$ wherein X is independently selected from a bond and $C_{1-4}$alkylene; and R$^5$ is selected from hydrogen and $C_{1-6}$alkyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of PPAR activity, particularly PPARδ, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which PPAR activity, particularly PPARδ, activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3] dioxole, imidazolyl, benzoimidazolyl, pyrimidinyl, furanyl, oxazolyl, isoxazolyl, triazolyl, tetrazolyl, pyrazolyl, thienyl, etc. "$C_{6-10}arylC_{0-4}alkyl$" means an aryl as described above connected via a alkylene grouping. For example, $C_{6-10}aryl$ $C_{0-4}alkyl$ includes phenethyl, benzyl, etc.

"Cycloalkyl" means a saturated or partially unsaturated, monocyclic, fused bicyclic or bridged polycyclic ring assembly containing the number of ring atoms indicated. For example, $C_{3-10}cycloalkyl$ includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}alkyl$ or a nitrogen protecting group. For example, $C_{3-8}heterocycloalkyl$ as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

Description of the Preferred Embodiments

The present invention provides compounds, compositions and methods for the treatment of diseases in which modulation of PPARδ activity can prevent, inhibit or ameliorate the pathology and/or symptomology of the diseases, which method comprises administering to the animal a therapeutically effective amount of a compound of Formula I.

In one embodiment, with reference to compounds of Formula I: $R^1$ is selected from $C_{1-6}alkyl$, $C_{3-12}cycloalkyl$, $C_{5-10}heteroaryl$ and $C_{6-10}aryl$; wherein any aryl or heteroaryl of $R_1$ is optionally substituted by 1 to 3 radicals independently selected from halo, nitro, $C_{1-6}alkyl$, $C_{1-6}alkoxy$, halo-substituted-$C_{1-6}alkyl$ and —XC(O)OR$^5$; wherein X is a bond or $C_{1-4}alkylene$; and $R^5$ is selected from hydrogen and $C_{1-6}alkyl$; $R^2$ is selected from —XOXOR$^5$, —XOR$^5$, —C(O) NR$^4$XOR$^4$, —C(O)NR$^4$XOR$^5$, —C(O)OXOR$^5$, —C(O) XOR$^5$, —C(O)NR$^4$R$^4$, —C(O)NR$^4$R$^5$ and —C(O)NR$^4$XR$^5$; wherein X is a bond or $C_{1-4}alkylene$; $R^4$ is selected from hydrogen and $C_{1-6}alkyl$; $R^5$ is $C_{3-12}cycloalkyl$, $C_{3-8}heterocycloalkyl$, $C_{6-10}aryl$ and $C_{5-10}heteroaryl$; or $R^4$ and $R^5$ together with the nitrogen atom to which $R^4$ and $R^5$ are attached form $C_{3-8}heterocycloalkyl$ or $C_{5-10}heteroaryl$; wherein any alkylene group of $R^2$ is optionally substituted by $C_{1-6}alkyl$ and phenyl; wherein any aryl, heteroaryl, cycloalkyl and heterocycloalkyl of $R^2$ is optionally substituted with 1 to 3 radicals independently selected from halo, nitro, $C_{1-6}alkyl$, $C_{1-6}alkoxy$, halo-substituted-$C_{1-6}alkyl$ and halo-substituted-$C_{1-6}alkoxy$; and $R^3$ is $C_{6-10}aryl$ optionally substituted with 1 to 3 radicals independently selected from halo, $C_{1-6}alkyl$, $C_{1-6}alkoxy$, —OXC(O)OR$^5$ and —XC(O)OR$^5$ wherein X is a bond or $C_{1-4}alkylene$; and $R^5$ is selected from hydrogen and $C_{1-6}alkyl$.

In another embodiment, $R^1$ is selected from methyl, ethyl, t-butyl, propyl, cyclopropyl, isopropyl, pyridinyl, furanyl, thienyl and phenyl optionally substituted with 1 to 2 radicals independently selected from halo, methyl, nitro, methoxy, carboxymethyl and trifluoromethyl.

In a further embodiment, $R^2$ is selected from —C(O) NHR$^4$, —C(O)NHR$^5$, —C(O)N(CH$_3$)CH$_2$R$^5$, —CH$_2$—O—(CH$_2$)$_2$OR$^5$, —CH$_2$OR$^5$, —C(O)NH(CH$_2$)$_2$OR$^5$, —C(O)O (CH$_2$)$_2$OR$^5$, —C(O)(CH$_2$)$_3$OR$^5$, —C(O)NH(CH$_2$)$_{1-3}$R$^5$, —C(O)NH(CH$_2$)$_2$OR$^4$ and —C(O)N(CH$_3$)(CH$_2$)$_2$OR$^5$; wherein $R^4$ is selected from methyl and butyl; $R^5$ is selected from phenyl, cyclopentyl, furanyl, pyridinyl and naphthyl; or $R^4$ and $R^5$ together with the nitrogen atom to which $R^4$ and $R^5$ are attached form 3,4-dihydro-1H-isoquinolin-2-yl; wherein any alkylene group of $R^2$ is optionally substituted by a radical selected from methyl and phenyl; wherein any aryl, heteroaryl, cycloalkyl and heterocycloalkyl of $R^2$ is optionally substituted with 1 to 3 radicals independently selected from halo, nitro, methyl, trifluoromethyl, trifluoromethoxy and methoxy.

In a further embodiment, $R^3$ is phenyl optionally substituted with 1 to 3 radicals independently selected from halo, methyl, methoxy, —OCH$_2$C(O)OH, —(CH$_2$)$_2$C(O)OH and —CH$_2$C(O)OH.

In another embodiment, are compounds of Formula Ia:

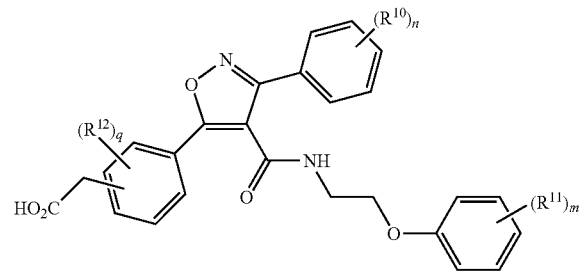

Ia in which: q, m and n are independently selected from 0, 1 and 2; and $R^{10}$, $R^{11}$ and $R^{12}$ are each independently selected from halo, $C_{1-6}alkyl$, nitro, $C_{1-6}alkoxy$ and halo-substituted-$C_{1-6}alkyl$.

Preferred compounds of Formula I are detailed in the Examples and tables, infra. Further preferred compounds are selected from: (5-{4-[2-(2,4-Dichloro-phenoxy)-ethyl-carbamoyl]-5-phenyl-isoxazol-3-yl}-phenyl)-acetic acid; (3-Chloro-4-{4-[2-(2,4-dichloro-phenoxy)-ethylcarbamoyl]-5-phenyl-isoxazol-3-yl}-phenyl)-acetic acid; (3-Chloro-4-{4-[2-(2,4-dichloro-phenoxy)-ethylcarbamoyl]-5-p-tolyl-isoxazol-3-yl}-phenyl)-acetic acid; {3-Chloro-4-[4-[2-(2,4-dichloro-phenoxy)-ethylcarbamoyl]-5-(4-fluoro-phenyl)-isoxazol-3-yl]-phenyl}-acetic acid; {3-Chloro-4-[4-[2-(2,4-dichloro-phenoxy)-ethylcarbamoyl]-5-(4-nitro-phenyl)-isoxazol-3-yl]-phenyl}-acetic acid; (3-Chloro-4-{5-(2-chloro-phenyl)-4-[2-(2,4-dichloro-phenoxy)-ethylcarbamoyl]-isoxazol-3-yl}-phenyl)-acetic acid; (3-Chloro-4-{5-(4-chloro-phenyl)-4-[2-(2,4-dichloro-phenoxy)-ethylcarbamoyl]-isoxazol-3-yl}-phenyl)-acetic acid; {3-Chloro-4-[4-[2-(2,4-dichloro-phenoxy)-ethylcarbamoyl]-5-(2-methoxy-phenyl)-isoxazol-3-yl]-phenyl}-acetic acid; {3-Chloro-4-[4-[2-(2,4-dichloro-phenoxy)-ethylcarbamoyl]-5-(3-methoxy-phenyl)-isoxazol-3-yl]-phenyl}-acetic acid; {3-Chloro-4-[4-[2-(2,4-dichloro-phenoxy)-ethylcarbamoyl]-5-(4-methoxy-phenyl)-isoxazol-3-yl]-phenyl}-acetic acid; {3-Chloro-4-[4-[2-(2,4-dichloro-phenoxy)-ethylcarbamoyl]-5-(2-trifluoromethyl-phenyl)-isoxazol-3-yl]-phenyl}-acetic acid; {3-Chloro-4-[4-[2-(2,4-dichloro-phenoxy)-ethylcarbamoyl]-5-(3-trifluoromethyl-phenyl)-isoxazol-3-yl]-phenyl}-acetic acid; {3-Chloro-4-[4-[2-(2,4-dichloro-phenoxy)-ethylcarbamoyl]-5-(4-trifluoromethyl-phenyl)-isoxazol-3-yl]-phenyl}-acetic acid; (3-{4-[2-(2,4-Dichloro-phenoxy)-ethylcarbamoyl]-5-p-tolyl-isoxazol-3-yl}-phenyl)-acetic acid; {3-[4-[2-(2,4-Dichloro-phenoxy)-ethylcarbamoyl]-5-(4-fluoro-phenyl)-isoxazol-3-yl]-phenyl}-acetic acid; {3-[4-[2-(2,4-Dichloro-phenoxy)-ethylcarbamoyl]-5-(4-nitro-phenyl)-isoxazol-3-yl]-phenyl}-acetic acid; (3-{5-(2-Chloro-phenyl)-4-[2-(2,4-dichlorophenoxy)-ethylcarbamoyl]-isoxazol-3-yl}-phenyl)-acetic acid; (3-{5-(3-Chloro-phenyl)-4-[2-(2,4-dichloro-phenoxy)-ethylcarbamoyl]-isoxazol-3-yl}-phenyl)-acetic acid; (3-{5-(4-Chloro-phenyl)-4-[2-(2,4-dichloro-phenoxy)-ethylcarbamoyl]-isoxazol-3-yl}-phenyl)-acetic acid; {3-[4-[2-(2,4-Dichloro-phenoxy)-ethylcarbamoyl]-5-(2-methoxy-phenyl)-isoxazol-3-yl]-phenyl}-acetic acid; {3-[4-[2-(2,4-Dichloro-phenoxy)-ethylcarbamoyl]-5-(3-methoxy-phenyl)-isoxazol-3-yl]-phenyl}-acetic acid; {3-[4-[2-(2,4-Dichloro-phenoxy)-ethylcarbamoyl]-5-(4-methoxy-phenyl)-isoxazol-3-yl]-phenyl}-acetic acid; {3-[4-[2-(2,4-Dichloro-phenoxy)-ethylcarbamoyl]-5-(2-trifluoromethyl-phenyl)-isoxazol-3-yl]-phenyl}-acetic acid; {3-[4-[2-(2,4-Dichloro-phenoxy)-ethylcarbamoyl]-5-(3-trifluoromethyl-phenyl)-isoxazol-3-yl]-phenyl}-acetic acid; {3-[4-[2-(2,4-Dichloro-phenoxy)-ethylcarbamoyl]-5-(4-trifluoromethyl-phenyl)-isoxazol-3-yl]-phenyl}-acetic acid; (3-{4-[2-(2,4-Dichloro-phenoxy)-ethylcarbamoyl]-5-o-tolyl-isoxazol-3-yl}-phenyl)-acetic acid; and (3-{4-[2-(2,4-Dichloro-phenoxy)-ethylcarbamoyl]-5-m-tolyl-isoxazol-3-yl}-phenyl)-acetic acid.

Further preferred compounds are detailed in the examples and tables, infra.

Pharmacology and Utility

Compounds of the invention modulate the activity of PPARs and, as such, are useful for treating diseases or disorders in which PPARs contributes to the pathology and/or symptomology of the disease. This invention further provides compounds of this invention for use in the preparation of medicaments for the treatment of diseases or disorders in which PPARs, particularly PPARδ, contributes to the pathology and/or symptomology of the disease.

Such compounds may therefore be employed for the treatment of prophylaxis, dyslipidemia, hyperlipidemia, hypercholesteremia, atherosclerosis, atherogenesis, hypertriglyceridemia, heart failure, hyper cholesteremia, myocardial infarction, vascular diseases, cardiovascular diseases, hypertension, obesity, cachexia, HIV wasting syndrome, inflammation, arthritis, cancer, Alzheimer's disease, anorexia, anorexia nervosa, bulimia, skin disorders, respiratory diseases, ophthalmic disorders, IBDs (irritable bowel disease), ulcerative colitis and Crohn's disease. Preferably for the treatment of prophylaxis, dyslipidemia, hyperlipidemia, hypercholesteremia, atherosclerosis, atherogenesis, hypertriglyceridemia, cardiovascular diseases, hypertension, obesity, inflammation, cancer, skin disorders, IBDs (irritable bowel disease), ulcerative colitis and Crohn's disease.

Compounds of the invention can also be employed to treat long term critical illness, increase muscle mass and/or muscle strength, increase lean body mass, maintain muscle strength and function in the elderly, enhance muscle endurance and muscle function, and reverse or prevent frailty in the elderly.

Further, the compounds of the present invention may be employed in mammals as hypoglycemic agents for the treatment and prevention of conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome X. Preferably type-1 and type-2 diabetes, Impaired Glucose Metabolism (IGM), Impaired Glucose Tolerance (IGT) and Impaired Fasting Glucose (IFG).

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of the invention or a pharmaceutically acceptable salt thereof. For any of the above uses, the required dosage will vary depending on the mode of administration, the particular condition, to be treated and the effect desired. The present invention also concerns: i) a compound of the invention or a pharmaceutically acceptable salt thereof for use as a medicament; and ii) the use of a compound of the invention or a pharmaceutically acceptable salt thereof for the manufacture of a medicament for preventing or treating any of the diseases or disorders described above.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

This invention also concerns a pharmaceutical composition comprising a therapeutically effective amount of a compound as described herein in combination with one or more pharmaceutically acceptable carriers.

Compounds of the invention can be administered in therapeutically effective amounts in combination with one or more therapeutic agents (pharmaceutical combinations).

Thus, the present invention also relates to pharmaceutical combinations, such as a combined preparation or pharmaceutical composition (fixed combination), comprising: 1) a compound of the invention as defined above or a pharmaceutical acceptable salt thereof; and 2) at least one active ingredient selected from:

a) anti-diabetic agents such as insulin, insulin derivatives and mimetics; insulin secretagogues such as the sulfonylureas, e.g., Glipizide, glyburide and AMARYL® (glimepiride tablets); insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPARy agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) a HDL increasing compound;

f) Cholesterol absorption modulator such as ZETIA (ezetimibe) and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-$HT_3$ receptor and/or an agent interacting with 5-$HT_4$ receptor such as tegaserod described in the U.S. Pat. No. 5,510,353 as example 13, tegaserod hydrogen maleate, cisapride, cilansetron;

or, in each case a pharmaceutically acceptable salt thereof; and optionally a pharmaceutically acceptable carrier.

Most preferred combination partners are tegaserod, imatinib, vildagliptin, metformin, a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid, a sulfonylurea receptor ligand, aliskiren, valsartan, orlistat or a statin such as pitavastatin, simvastatin, fluvastatin or pravastatin.

Preferably the pharmaceutical combinations contains a therapeutically effective amount of a compound of the invention as defined above, in a combination with a therapeutically effective amount of another therapeutic agent as described above, e.g., each at an effective therapeutic dose as reported in the art. Combination partners (1) and (2) can be administered together, one after the other or separately in one combined unit dosage form or in two separate unit dosage forms. The unit dosage form may also be a fixed combination.

The structure of the active agents identified by generic or trade names may be taken from the actual edition of the standard compendium "The Merck Index" or the Physician's Desk Reference or from databases, e.g. Patents International (e.g. IMS World Publications) or Current Drugs. The corresponding content thereof is hereby incorporated by reference.

Any person skilled in the art is fully enabled to identify the active agents and, based on these references, likewise enabled to manufacture and test the pharmaceutical indications and properties in standard test models, both in vitro and in vivo.

In another preferred aspect the invention concerns a pharmaceutical composition (fixed combination) comprising a therapeutically effective amount of a compound as described herein, in combination with a therapeutically effective amount of at least one active ingredient selected from the above described group a) to m), or, in each case a pharmaceutically acceptable salt thereof.

A pharmaceutical composition or combination as described herein for the manufacture of a medicament for the treatment of for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, IBDs (irritable bowel disease), ulcerative colitis, Crohn's disease, conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome-X.

Such therapeutic agents include estrogen, testosterone, a selective estrogen receptor modulator, a selective androgen receptor modulator, insulin, insulin derivatives and mimetics; insulin secretagogues such as the sulfonylureas, e.g., Glipizide and AMARYL® (glimepiride tablets); insulinotropic sulfonylurea receptor ligands, such as meglitinides, e.g., nateglinide and repaglinide; insulin sensitizers, such as protein tyrosine phosphatase-1B (PTP-1B) inhibitors, GSK3 (glycogen synthase kinase-3) inhibitors or RXR ligands; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors, e.g. isoleucin-thiazolidide; DPP728 and LAF237, hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (liver X receptor) and LXR (farnesoid X receptor) ligands, cholestyramine, fibrates, nicotinic acid and aspirin. A compound of the present invention may be administered either simultaneously, before or after the other active ingredient, either separately by the same or different route of administration or together in the same pharmaceutical formulation.

The invention also provides for pharmaceutical combinations, e.g. a kit, comprising: a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which $R^2$ is —C(O)OR$^5$, can be prepared by proceeding as in the following Reaction Scheme 1:

Reactions Scheme 1

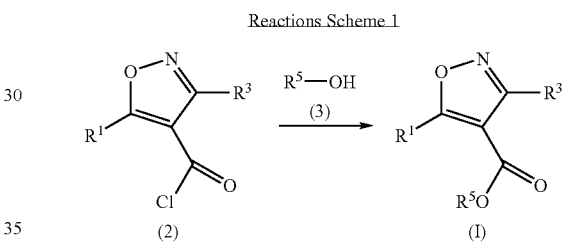

in which $R^1$, $R^3$ and $R^5$ are as defined for Formula I in the Summary of the Invention. Compounds of Formula I are prepared by reacting a compound of formula 2 with a compound of formula 3 in the presence of a suitable catalyst (e.g., dimethyl-tin chloride, or the like) and a suitable solvent (e.g., THF, or the like). The reaction is carried out in the temperature range of 0 to 60° C. and takes up to 20 hours to complete.

Compounds of Formula I, in which $R^2$ is —XOR$^5$ (X is methylene), can be prepared by proceeding as in the following Reaction Scheme 2:

Reactions Scheme 2

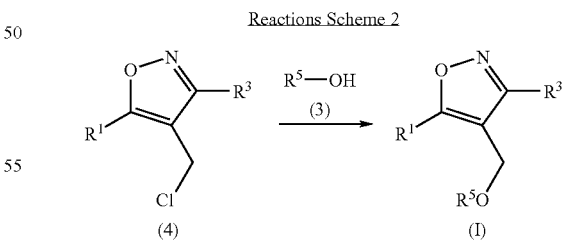

in which $R^1$, $R^3$ and $R^5$ are as defined for Formula I in the Summary of the Invention. Compounds of Formula I are prepared by reacting a compound of formula 4 with a compound of formula 3 in the presence of a suitable base (e.g., sodium hydride, or the like) and a suitable solvent (e.g., dichloromethane, or the like). The reaction is carried out in the temperature range of 0 to 90° C. and takes up to 8 hours to complete.

Compounds of Formula I, in which $R^2$ is —C(O)NR$^4$R$^5$, can be prepared by proceeding as in the following Reaction Scheme 3:

Reactions Scheme 3

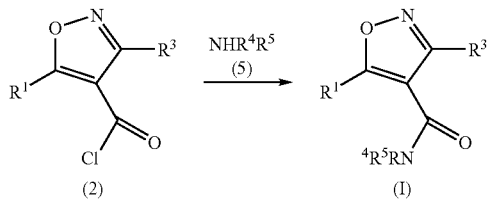

in which $R^1$, $R^3$, $R^4$ and $R^5$ are as defined for Formula I in the Summary of the Invention. Compounds of Formula I are prepared by reacting a compound of formula 2 with a compound of formula 5 in the presence of a suitable base (e.g., triethylamine, or the like) and a suitable solvent (e.g., dichloromethane, or the like). The reaction is carried out in the temperature range of 0 to 50° C. and takes up to 8 hours to complete.

Compounds of Formula I, in which $R^1$ is methyl, can be prepared by proceeding as in the following Reaction Scheme 4:

Reactions Scheme 4

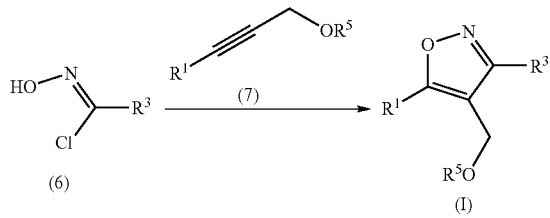

in which $R^1$, $R^3$ and $R^5$ are as defined for Formula I in the Summary of the Invention. Compounds of Formula I are prepared by reacting a compound of formula 6 with a compound of formula 7 in the presence of a suitable base (e.g., triethylamine, or the like) and optionally in the presence of a suitable solvent (e.g., dichloroethane, or the like). The reaction is carried out in the temperature range of 50 to 120° C. and takes up to 15 hours to complete.

Compounds of Formula I, in which $R^1$ is methyl, can be prepared by proceeding as in the following Reaction Scheme 5:

Reactions Scheme 5

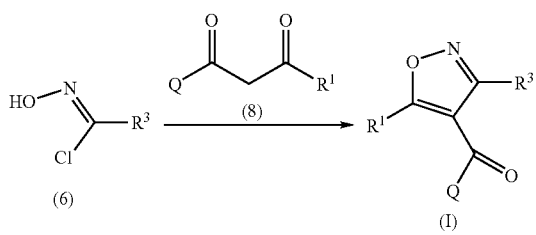

in which $R^1$, $R^3$, $R^4$ and $R^5$ are as defined for Formula I in the Summary of the Invention. Q represents —OR$^5$, —NR$^4$R$^4$, —NR$^4$XOR$^4$, —NR$^4$XOR$^5$, —NR$^4$R$^5$ and —NR$^4$XR$^5$ according to the definition of $R^2$ in the Summary of the Invention. Compounds of Formula I are prepared by reacting a compound of formula 6 with a compound of formula 8 in the presence of a suitable base (e.g., triethylamine, or the like) and a suitable solvent (e.g., dichloroethane, or the like). The reaction is carried out in the temperature range of 50 to 120° C. and takes up to 15 hours to complete.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.)

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1, 2, 3, 4 or 5; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

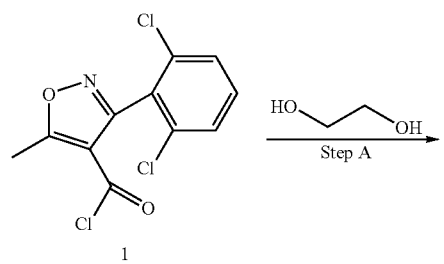

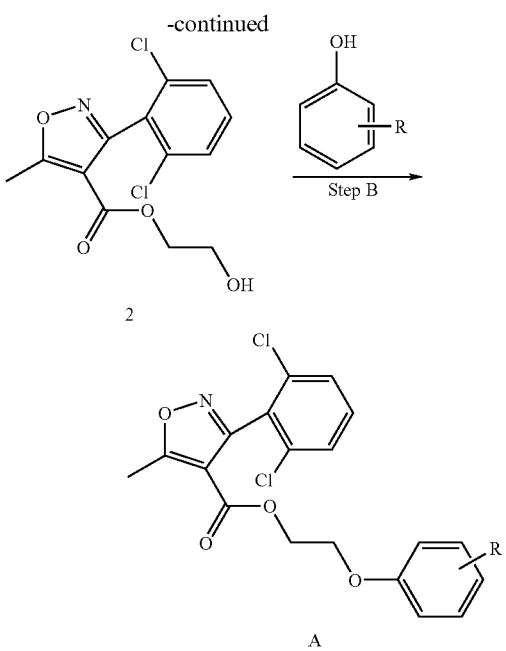

Example A1

3-(2,6-Dichloro-phenyl)-5-methyl-isoxazole-4-carboxylic acid 2-(2-nitro-4-trifluoromethyl-phenoxy)-ethyl ester

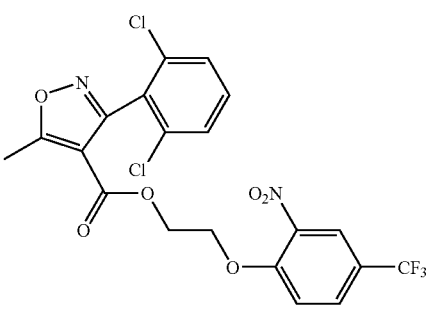

Step A: To a solution of ethylene glycol (0.62 g, 10 mmol) in THF (50 mL) is added a catalytic amount of dimethyl tin dichloride (5 mol %), K$_2$CO$_3$ (2.76 g, 20 mmol) and 3-(2,6-Dichloro-phenyl)-5-methyl-isoxazole-4-carbonyl chloride 1 (2.91 g, 10 mmol), successively, at room temperature. The mixture is stirred overnight at room temperature, then poured into water and extracted three times with DCM (300 mL). The organic layers are combined, dried (MgSO$_4$), filtered and concentrated to afford crude 2 as a white solid.

Step B: 3-(2,6-Dichloro-phenyl)-5-methyl-isoxazole-4-carboxylic acid 2-hydroxy-ethyl ester 2 (25 mg, 0.079 mmol), triphenylphosphine (31 mg, 0.119 mmol) and 2-nitro-4-trifluoromethyl-phenol (19.6 mg, 0.095 mmol) are dissolved in DCM (1 mL) and cooled to 0° C. Diethyl azodicarboxylate (27.5 mg, 0.158 mmol) is added dropwise, the solution is warmed to room temperature and stirred for 12 hours. Then the mixture is concentrated and purified on reverse phase HPLC(H₂O/MeCN gradient) to afford the title compound A1 as a yellow solid: MS calculated for $C_{20}H_{14}Cl_2F_3N_2O_6$ (M+H⁺) 505.0, found 505.0.

Example A2

3-(2,6-Dichloro-phenyl)-5-methyl-isoxazole-4-carboxylic acid 2-(2,4-dichloro-phenoxy)-ethyl ester

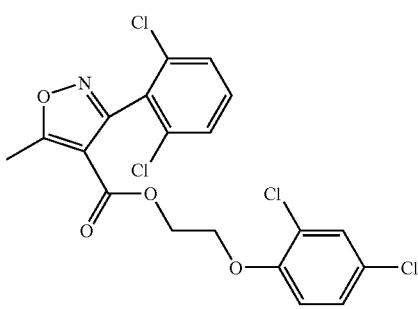

Following the procedure of Example A1, except substituting 2,4-dichlorophenol for 2-nitro-4-trifluoromethyl-phenol in Step B, the title compound is prepared as a white solid: MS calculated for $C_{19}H_{14}Cl_4NO_4$ (M+H⁺) 460.0, found 460.0.

Example B 3-(2,6-Dichloro-phenyl)-5-methyl-4-[2-(2-nitro-4-trifluoromethyl-phenoxy)-ethoxymethyl]-isoxazole

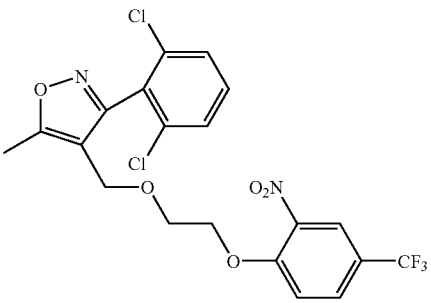

Step A: A solution of isoxazole 3 (5.0 g, 18.4 mmol) in dry THF (100 mL) is cooled to 0° C. LAH (27.8 mL of a 1 M solution in THF) is added dropwise and the reaction mixture is stirred at room temperature for 20 hours. Sodium sulfate decahydrate is added slowly together with THF (70 mL) and the mixture is stirred for another 1 hour at room temperature. The mixture is then filtered over celite, the solvent is evaporated and the remainder is purified by column chromatography using a DCM/MeOH gradient to yield intermediate 4 as a white solid: ¹H-NMR (400 MHz, CDCl₃) δ=7.32-7.21 (m,

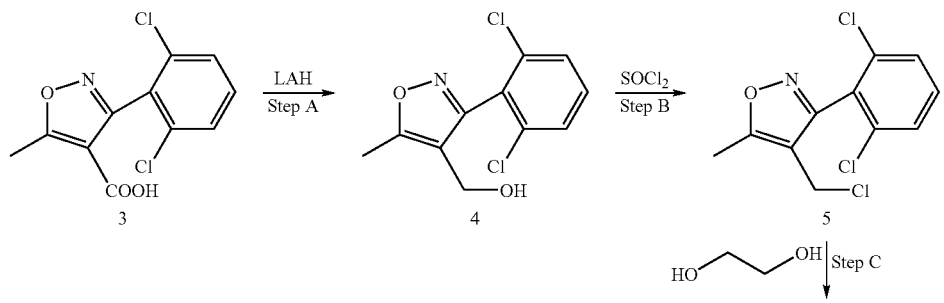

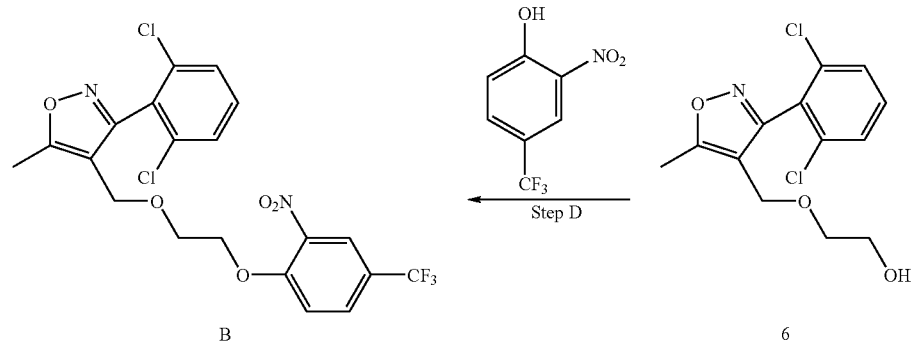

3H), 4.23 (s, 2H), 2.43 (s, 3H). MS calculated for $C_{11}H_{10}Cl_2NO_2$ (M+H$^+$) 258.0, found 258.2.

Step B: [3-(2,6-Dichloro-phenyl)-5-methyl-isoxazol-4-yl]-methanol 4 (1.23 g, 4.8 mmol) is dissolved in DCM (35 mL) and cooled to 0° C. Thionyl chloride (0.42 mL, 5.72 mmol) dissolved in DCM (15 mL) is added dropwise. After the addition is completed the reaction mixture is stirred at room temperature for 1 hour. Then the mixture is concentrated in vacuo and the remainder is purified by column chromatography using a DCM/MeOH gradient to yield intermediate 5 as a white solid: $^1$H-NMR (400 MHz, CDCl$_3$) δ=7.46-7.26 (m, 3H), 4.27 (s, 2H), 2.57 (s, 3H). MS calculated for $C_{11}H_9Cl_3NO$ (M+H$^+$) 276.0, found 276.2.

Step C: To a suspension of NaH (60% dispersion in mineral oil, 100 mg, 2.5 mmol) in ethylene glycol (10 mL) is added 4-Chloromethyl-3-(2,6-dichloro-phenyl)-5-methyl-isoxazole 5 (0.20 g, 0.72 mmol). The mixture is stirred at 80° C. for 3 hours. The mixture is then acidified with 0.5 M HCl, diluted with H$_2$O and extracted three times with DCM. The organic layers are combined, dried (MgSO$_4$), filtered and concentrated. The remainder is purified by column chromatography using a DCM/MeOH gradient to afford intermediate 6 as colorless oil: $^1$H-NMR (400 MHz, CDCl$_3$) δ=7.37-7.19 (m, 3H), 4.19 (s, 2H), 3.52 (t, J=4.5 Hz, 2H), 3.33 (t, J=4.5 Hz, 2H), 2.47 (s, 3H). MS calculated for $C_{13}H_{14}Cl_2NO_3$ (M+H$^+$) 302.0, found 302.2.

Step D: 2-[3-(2,6-Dichloro-phenyl)-5-methyl-isoxazol-4-ylmethoxy]-ethanol 6 (50 mg, 0.17 mmol), triphenylphosphine (66 mg, 0.25 mmol) and 2-nitro-4-trifluoromethyl-phenol (42 mg, 0.20 mmol) are dissolved in DCM (2 mL) and cooled to 0° C. Diethyl azodicarboxylate (58 mg, 0.34 mmol) is added dropwise, the solution is warmed to room temperature and stirred for 12 hours. Then the mixture is concentrated and purified on reverse phase HPLC(H$_2$O/MeCN gradient) to afford the title compound B as a white solid: $^1$H-NMR (400 MHz, CDCl$_3$) δ=8.11 (d, J=1.9 Hz, 1H), 7.73 (dd, J=8.8 Hz, J=1.8 Hz, 1H), 7.38-7.26 (m, 3H), 7.12 (d, J=8.8 Hz, 1H), 4.35 (s, 2H), 4.20 (t, J=4.5 Hz, 2H), 3.71 (t, J=4.5 Hz, 2H), 2.54 (s, 3H). MS calculated for $C_{20}H_{16}Cl_2F_3N_2O_5$ (M+H$^+$) 491.0, found 491.1.

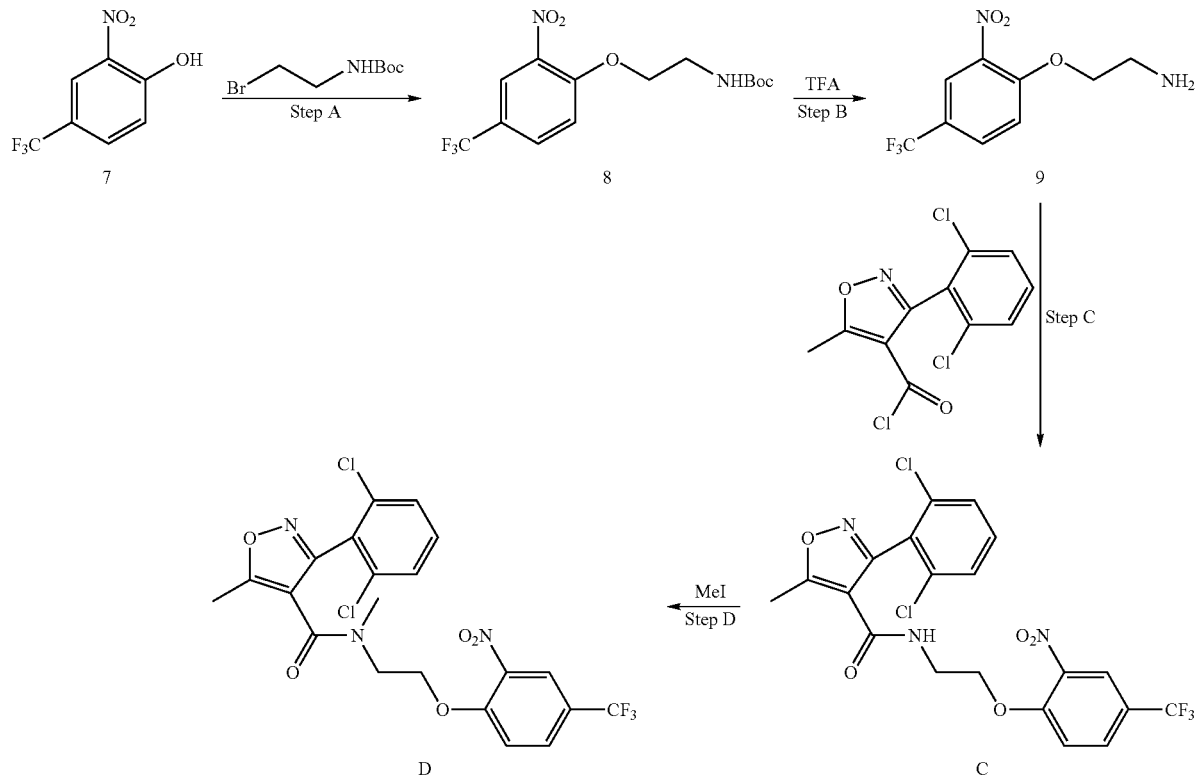

Example C 3-(2,6-Dichloro-phenyl)-5-methyl-isoxazole-4-carboxylic acid [2-(2-nitro-4-trifluoromethyl-phenoxy)-ethyl]-amide

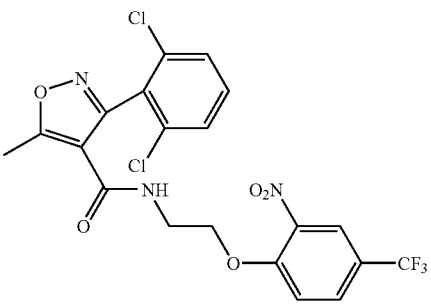

Step A: 2-nitro-4-trifluoromethyl-phenol 7 (0.5 g, 2.42 mmol) and (2-Bromo-ethyl)-carbamic acid tert-butyl ester (0.54 g, 2.42 mmol) are dissolved in MeCN. Cs$_2$CO$_3$ is added (1.58 g, 4.84 mmol) and the mixture is stirred at 90° C. for 6 hours. The mixture is then filtered, concentrated in vacuo, diluted with H₂O and extracted three times with DCM. The organic layers are combined, dried (MgSO₄), filtered, and concentrated and the remainder purified by column chromatography using a DCM/MeOH gradient to afford intermediate 8 as a yellow solid: $^1$H-NMR (400 MHz, CDCl₃) δ=8.42 (d, J=1.1 Hz, 1H), 8.37 (m, NH), 7.58 (dd, J=9.0 Hz, J=2.0 Hz, 1H), 6.92 (d, J=9.0 Hz, 1H), 4.29 (t, J=5.5 Hz, 2H), 3.60 (q, J=5.5 Hz, 2H), 1.42 (s, 9H). MS calculated for $C_9H_{10}F_3N_2O_3$ (M-Boc⁺) 251.1, found 251.2.

Step B: [2-(2-Nitro-4-trifluoromethyl-phenoxy)-ethyl]-carbamic acid tert-butyl ester 8 (0.81 g, 2.30 mmol) is dissolved in 5% trifluoroacetic acid in DCM (20 mL) and stirred at room temperature for 4 hours. The mixture is then concentrated, diluted with aqueous sat. K₂CO₃ and extracted three times with DCM. The organic layers are combined, dried (MgSO₄), filtered, and concentrated to afford intermediate 9 as a yellow oil: $^1$H-NMR (400 MHz, CDCl₃) δ=8.49 (d, J3=1.1 Hz, 1H), 7.63 (dd, J=9.0 Hz, J=2.0 Hz, 1H), 7.00 (d, J=9.0 Hz, 1H), 3.99 (t, J=5.4 Hz, 2H), 3.56 (q, J=5.3 Hz, 2H), 1.63 (s, NH2). MS calculated for $C_9H_{10}F_3N_2O_3$ (M+H⁺) 251.1, found 251.2.

Step C: 2-(2-Nitro-4-trifluoromethyl-phenoxy)-ethylamine 9 (0.25 g, 1.00 mmol) and 3-(2,6-Dichloro-phenyl)-5-methyl-isoxazole-4-carbonyl chloride 1 (0.30 g, 1.00 mmol) are dissolved in DCM (25 mL). Triethyl amine (0.21 mL, 1.50 mmol) is added and the solution is stirred at room temperature for 2 hours. The solution is then washed three times with H₂O, concentrated and purified on reverse phase HPLC(H₂O/MeCN gradient) to afford the title compound C as a yellow solid: $^1$H-NMR (400 MHz, CDCl₃) δ=8.50 (d, J=1.2 Hz, 1H), 8.09 (m, NH), 7.64 (dd, J=9.0 Hz, J=2.1 Hz, 1H), 7.41-7.16 (m, 3H), 6.83 (d, J=9.0 Hz, 1H), 4.40 (t, J=5.3 Hz, 2H), 3.42 (q, J=5.3 Hz, 2H), 2.81 (s, 3H). MS calculated for $C_{20}H_{15}Cl_2F_3N_3O_5$ (M+H⁺) 504.0, found 504.2.

Example D 3-(2,6-Dichloro-phenyl)-5-methyl-isoxazole-4-carboxylic acid methyl-[2-(2-nitro-4-trifluoromethyl-phenoxy)-ethyl]-amide

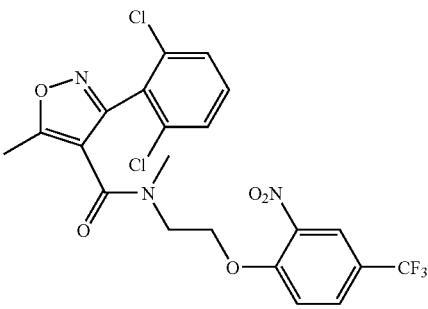

Step D: 3-(2,6-Dichloro-phenyl)-5-methyl-isoxazole-4-carboxylic acid [2-(2-nitro-4-trifluoromethyl-phenoxy)-ethyl]-amide (Example C, 20 mg, 0.04 mmol) is dissolved in DMF (0.5 mL) and cooled to 0° C. Sodium hydride (60% in mineral oil, 2 mg, 0.05 mmol) is added and the solution is stirred for 15 min at 0° C. Then methyl iodide (6.5 μL, 0.05 mmol) is added and the mixture is stirred at room temperature for 2 hours. The reaction mixture is diluted with H₂O and extracted three times with DCM. The organic layers are combined, dried (MgSO₄), filtered, and concentrated. The remainder is purified on reverse phase HPLC(H₂O/MeCN gradient) to afford the title compound D as a yellow solid: MS calculated for $C_{21}H_{17}Cl_2F_3N_3O_5$ (M+H⁺) 518.0, found 518.2.

Intermediate 16: [3-Chloro-4-(hydroxyimino-chloromethyl)-phenyl]-acetic acid methyl ester.

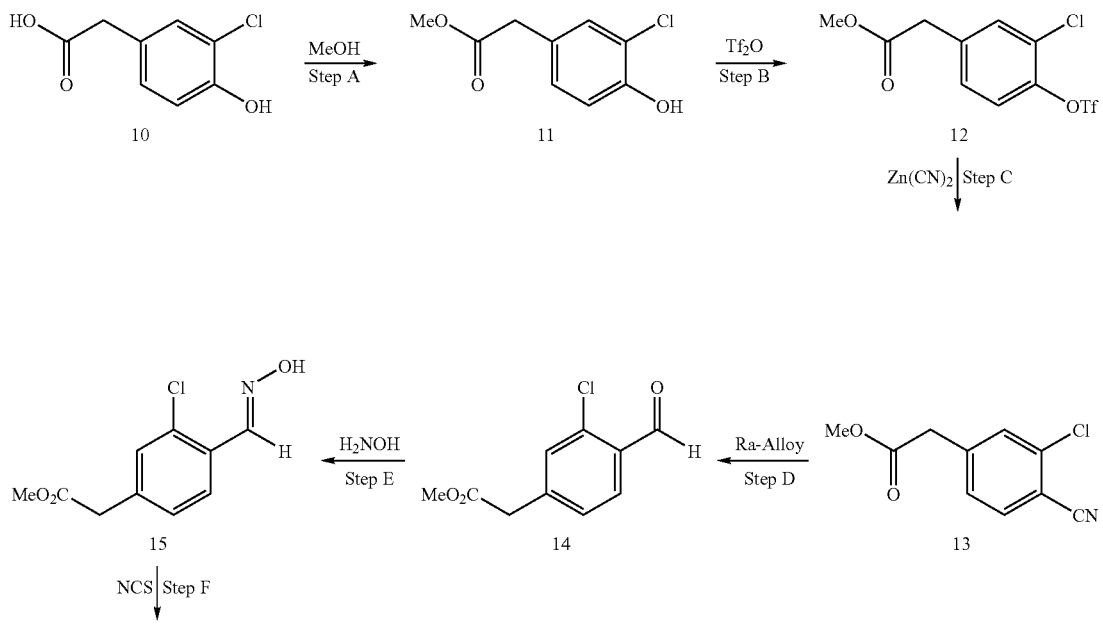

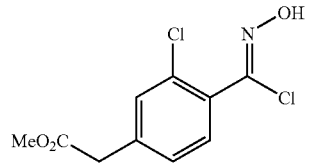

16

Step A: 3-Chloro-4-hydroxy-phenyl)-acetic acid 10 (20 g, 107 mmol) is dissolved in MeOH (250 mL) containing catalytic amounts of conc. $H_2SO_4$ (2.5 mL). The solution is heated to reflux overnight. The solvent is evaporated, the remainder is dissolved in DCM and washed with $H_2O$ (3×200 mL). The organic layer is dried ($MgSO_4$), filtered and concentrated to afford 11 as a light yellow solid: $^1$H-NMR (400 MHz, $CD_3OD$) δ=7.21 (d, J=2.1 Hz, 1H), 7.01 (dd, J=2.1 Hz, J=8.3, 1H), 6.84 (d, J=8.3 Hz, 1H), 3.67 (s, 3H), 3.54 (s, 2H). MS calculated for $C_9H_{10}ClO_3$ (M+H$^+$) 201.0, found 201.2.

Step B: To a solution of (3-Chloro-4-hydroxy-phenyl)-acetic acid methyl ester 11 (15.9 g, 79.3 mmol) and triethylamine (11.04 mL, 79.3 mmol) in DCM (160 mL) triflic anhydride (13.33 mL, 79.3 mmol) is added dropwise at 0° C. over a period of 2 hours. The reaction mixture is then diluted with EtOAc (300 mL) and washed successively with $NaHCO_3$, brine and water. The organic layer is dried ($MgSO_4$), filtered and concentrated to afford (3-chloro-4-trifluoromethanesulfonyloxy-phenyl)-acetic acid methyl ester 12 as colorless oil: MS calculated for $C_{10}H_9ClF_3O_5S$ (M+H$^+$) 333.0, found 333.1.

Step C: A solution of (3-chloro-4-trifluoromethanesulfonyloxy-phenyl)-acetic acid methyl ester 12 (24.5 g, 73.6 mmol) in dry DMF (45 mL) is combined with zinc cyanide (8.91 g, 75.9 mmol) and tetrakis(triphenylphosphine) palladium (8.50 g, 7.4 mmol). The mixture is stirred for 34 hours at 80° C., then cooled to room temperature, diluted with EtOAc (150 mL) and poured into a saturated $NaHCO_3$ solution (150 mL). A white precipitate is removed by vacuum filtration. The organic layer of the filtrate is separated and washed with $H_2O$. The organic layer is dried ($MgSO_4$), filtered and concentrated. The remainder is purified by silica gel chromatography using 20% EtOAc/hexane to give (3-chloro-4-cyano-phenyl)acetic acid methyl ester 13 as a wax-like solid: $^1$H-NMR (400 MHz, $CDCl_3$) δ=7.63 (d, J=8.0 Hz, 1H), 7.47 (d, J=1.2 Hz, 1H), 7.30 (dd, J=1.2 Hz, J=8.0 Hz, 1H), 3.72 (s, 3H), 3.69 (s, 2H). MS calculated for $C_{10}H_9O_2ClN$ (M+H$^+$) 210.0, found 210.0.

Step D: A solution of (3-chloro-4-cyano-phenyl)acetic acid methyl ester 13 (7.4 g, 35.3 mmol) in 88% formic acid (100 mL) is combined with Raney-alloy (9.0 g) and heated to reflux for 10 hours at 110° C. After cooling to room temperature, the alloy is removed by filtration over Celite. The filtrate is concentrated to ~10% of the original volume and diluted with EtOAc (250 mL) and washed three times with water (80 mL). The organic layer is dried ($MgSO_4$), filtered and concentrated to afford crude product, which is purified by silica gel chromatography using an EtOAc/hexane gradient to give (3-Chloro-4-formyl-phenyl)-acetic acid methyl ester 14 as a wax-like solid. Another amount of product 14 is collected by reesterification of saponified byproduct (3-Chloro-4-formyl-phenyl)-acetic acid: $^1$H-NMR (400 MHz, $CDCl_3$) δ=10.31 (s, 1H), 7.84 (d, J=8.0 Hz, 1H), 7.58 (s, 1H), 7.45 (d, J=8.0 Hz, 1H), 3.86 (s, 3H), 3.64 (s, 2H). MS calculated for $C_{10}H_{10}ClO_3$ (M+H$^+$) 213.0, found 213.3.

Step E: Hydroxylamine hydrochloride (2.45 g, 35.3 mmol) is dissolved in water (100 mL) and cooled to 0° C. on an ice-bath. $NaHCO_3$ (4.44 g, 52.9 mmol) is added and the solution is kept at 0° C. for 20 minutes. Then (3-Chloro-4-formyl-phenyl)-acetic acid methyl ester 14 (5.00 g, 23.5 mmol) dissolved in MeOH (75 mL) is added slowly. A white precipitate formed immediately. The ice-bath is removed and the mixture is stirred at room temperature for 2 hours. The MeOH is removed in vacuo and the product is extracted three times with DCM. The organic layers are combined, dried ($MgSO_4$), filtered, and concentrated to afford the intermediate 15 as a white solid: $^1$H-NMR (400 MHz, $CDCl_3$) δ=8.53 (s, 1H), 7.80 (d, J=8.1 Hz, 1H), 7.33 (s, 1H), 7.19 (d, J=8.0 Hz, 1H), 3.71 (s, 3H), 3.62 (s, 2H). MS calculated for $C_{10}H_{11}ClNO_3$ (M+H$^+$) 228.0, found 228.3.

Step F: [3-Chloro-4-(hydroxyimino-methyl)-phenyl]-acetic acid methyl ester 15 (0.91 g, 4.0 mmol) and N-chlorosuccinimide (0.53 g, 4.0 mmol) are dissolved in DMF (20 mL). After adding catalytic amounts of HCl(g) to the solution, an exothermic reaction occurs. After 2 hours of stirring at room temperature the mixture is diluted with $H_2O$ and extracted three times with ether to afford intermediate 16 as a wax-like solid, which is used immediately without further purification: MS calculated for $C_{10}H_{10}Cl_2NO_3$ (M+H$^+$) 262.0, found 262.3.

Example E1

(3-Chloro-4-{5-methyl-4-[2-(2-nitro-4-trifluoromethyl-phenoxy)-ethoxymethyl]-isoxazol-3-yl}-phenyl)-acetic acid

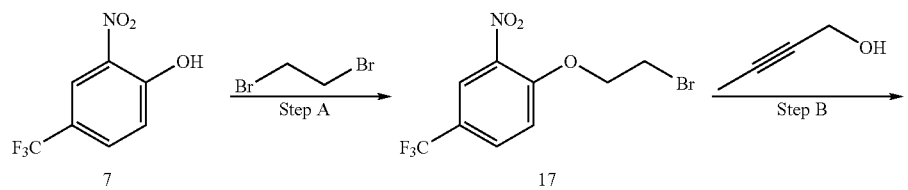

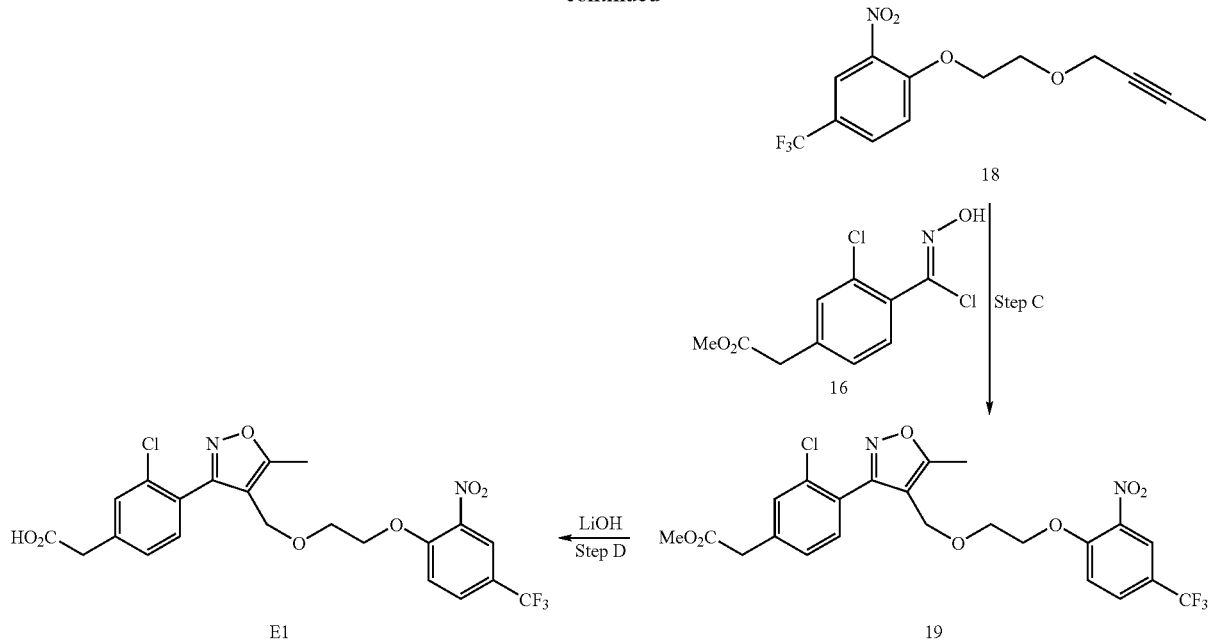

Step A: 2-nitro-4-trifluoromethyl-phenol 7 (1.3 g, 6.3 mmol) and 1,2-dibromo ethane (2.71 mL, 31 mmol) are dissolved in MeCN. $Cs_2CO_3$ is added (4.1 g, 12.6 mmol) and the mixture is stirred at 90° C. for 12 hours. The mixture is then filtered, concentrated in vacuo, diluted with $H_2O$ and extracted three times with DCM. The organic layers are combined, dried ($MgSO_4$), filtered, and concentrated and the remainder purified by column chromatography using a hexanes/EtOAc gradient to afford intermediate 17 as a yellow solid: $^1$H-NMR (400 MHz, $CDCl_3$) δ=8.06 (d, J=2.0 Hz, 1H), 7.73 (dd, J=8.8 Hz, J=2.0 Hz, 1H), 7.12 (d, J=8.8 Hz, 1H), 4.42 (t, J=6.4 Hz, 2H), 3.63 (t, J=6.4 Hz, 2H). MS calculated for $C_9H_8BrF_3NO_3$ (M+H$^+$) 314.0, found 314.2.

Step B: 1-(2-Bromo-ethoxy)-2-nitro-4-trifluoromethyl-benzene 17 (1.1 g, 3.5 mmol), 2-butyne-1-ol (0.53 mL, 7.0 mmol) and LiOH (0.6 g, 14.0 mmol) are dissolved in DMSO (10 mL). The mixture is stirred for 6 h at room temperature, diluted with $H_2O$ and extracted three times with DCM. The organic layers are combined, dried ($MgSO_4$), filtered, and concentrated and the remainder purified by column chromatography using a hexanes/EtOAc gradient to afford intermediate 18 as a yellow oil: $^1$H-NMR (400 MHz, $CDCl_3$) δ=8.06 (d, J=2.0 Hz, 1H), 7.71 (dd, J=8.9 Hz, J=2.0 Hz, 1H), 7.16 (d, J=8.9 Hz, 1H), 4.29 (t, J=4.7 Hz, 2H), 4.15 (q, J=2.3 Hz, 2H), 3.87 (t, J=4.7 Hz, 2H), 1.79 (t, J=2.3 Hz, 3H). MS calculated for $C_{13}H_{13}F_3NO_4$ (M+H$^+$) 304.1, found 304.3.

Step C: 1-(2-But-2-ynyloxy-ethoxy)-2-nitro-4-trifluoromethyl-benzene 18 (40 mg, 0.13 mmol) and chloroxime 16 (35 mg, 0.13 mmol) are dissolved in DCE (1 mL) together with triethylamine (50 μL, 0.36 mmol). The mixture is stirred for 10 h at 90° C. Then the mixture is concentrated in vacuo to yield crude (3-Chloro-4-{5-methyl-4-[2-(2-nitro-4-trifluoromethyl-phenoxy)-ethoxymethyl]-isoxazol-3-yl}-phenyl)-acetic acid methyl ester 19 as part of a mixture of two regioisomers, which is used in the next step without further purification. MS calculated for $C_{23}H_{21}ClF_3N_2O_7$ (M+H$^+$) 529.1, found 529.3.

Step D: The crude (3-Chloro-4-{5-methyl-4-[2-(2-nitro-4-trifluoromethyl-phenoxy)-ethoxymethyl]-isoxazol-3-yl}-phenyl)-acetic acid methyl ester 19 is dissolved in THF (1 mL), a solution of 1 M LiOH in $H_2O$ (0.2 mL) is added and the mixture is stirred overnight at 60° C. The mixture is acidified with 1 M HCl, EtOAc (10 mL) is added and the organic layer washed with $H_2O$ (3×5 mL). The organic layer is dried ($MgSO_4$), filtered, concentrated and purified on reverse phase HPLC($H_2O$/MeCN gradient) to afford the title compound E1 as a white solid: $^1$H-NMR (400 MHz, $CDCl_3$) δ=8.03 (d, J=2.0 Hz, 1H), 7.67 (dd, J=8.8 Hz, J=1.9 Hz, 1H), 7.33 (m, 2H), 7.18 (m, 1H), 7.05 (d, J=8.8 Hz, 1H), 4.32 (s, 2H), 4.12 (t, J=4.5 Hz, 2H), 3.66 (t, J=4.5 Hz, 2H), 3.61 (s, 2H), 2.43 (s, 3H). MS calculated for $C_{22}H_{19}ClF_3N_2O_7$ (M+H$^+$) 515.1, found 515.3.

Example E2

{3-Chloro-4-[5-methyl-4-(2-nitro-4-trifluoromethyl-phenoxymethyl)-isoxazol-3-yl]-phenyl}-acetic acid

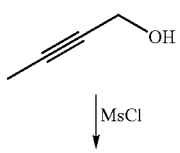

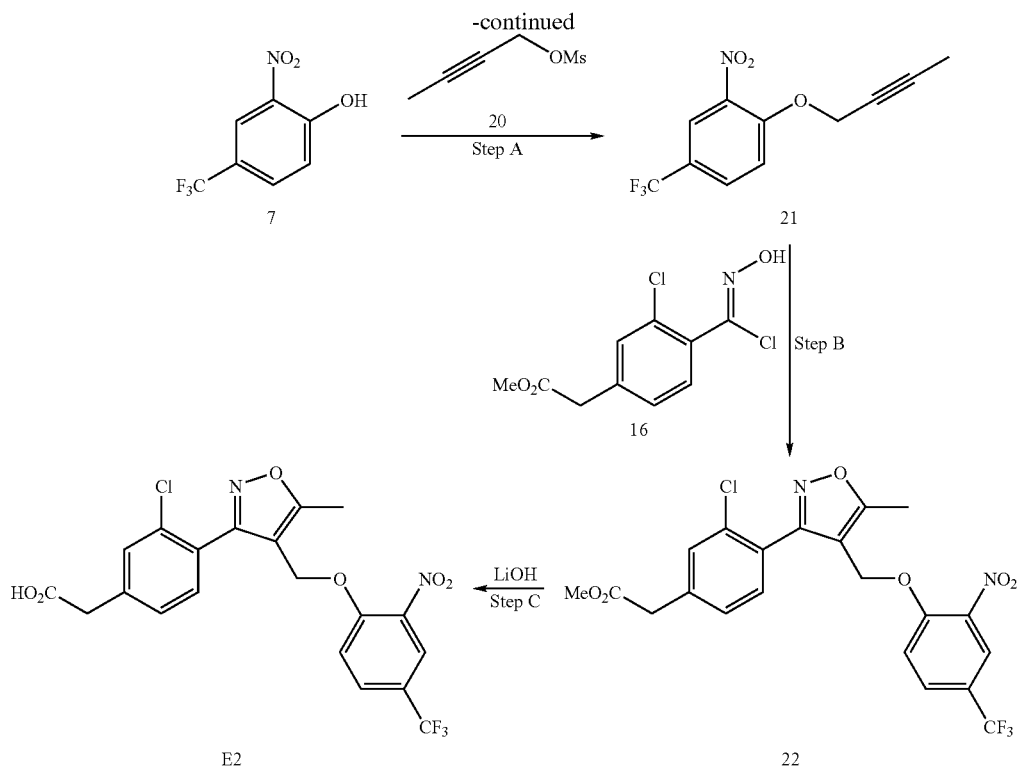

Step A: 2-Butyne-1-ol (1.4 g, 20 mmol) is dissolved in ether (50 mL) and cooled to 0° C. Triethylamine (3.3 mL, 24 mmol) is added to the solution. Methanesulfonyl chloride (1.6 mL, 22 mmol) is dissolved in ether (5 mL) and added dropwise to the reaction solution. The mixture is stirred for 30 minutes at 0° C., then filtered and concentrated to give crude methanesulfonic acid but-2-ynyl ester 20 (2.96 g, 20 mmol, quant.) as a colorless liquid: $^1$H-NMR (400 MHz, CDCl$_3$) δ=4.79 (q, J=2.4 Hz, 2H), 3.08 (s, 3H), 1.87 (t, J=2.4 Hz, 3H).

2-nitro-4-trifluoromethyl-phenol 7 (4.1 g, 20 mmol) and methanesulfonic acid but-2-ynyl ester 20 (3.0 g, 20 mmol) are dissolved in MeCN. Cs$_2$CO$_3$ is added (13.0 g, 40 mmol) and the mixture is stirred at 90° C. for 12 hours. The mixture is then filtered, concentrated in vacuo, diluted with H$_2$O and extracted three times with DCM. The organic layers are combined, dried (MgSO$_4$), filtered, and concentrated and the remainder purified by column chromatography using a hexanes/EtOAc gradient to afford 1-but-2-ynyloxy-2-nitro-4-trifluoromethyl-benzene 21 as a yellow solid: $^1$H-NMR (400 MHz, CDCl$_3$) δ=8.06 (d, J=1.7 Hz, 1H), 7.73 (dd, J=8.8 Hz, J=1.8 Hz, 1H), 7.30 (d, J=8.8 Hz, 1H), 4.81 (q, J=2.3 Hz, 2H), 1.79 (t, J=2.3 Hz, 3H). MS calculated for C$_{11}$H$_9$F$_3$NO$_3$ (M+H$^+$) 260.1, found 260.3.

Step B: 1-But-2-ynyloxy-2-nitro-4-trifluoromethyl-benzene 21 (34 mg, 0.13 mmol) and chloroxime 16 (35 mg, 0.13 mmol) are dissolved in DCE (1 mL) together with triethylamine (25 µL, 0.18 mmol). The mixture is stirred for 10 h at 90° C. Then the mixture is concentrated in vacuo to yield crude {3-Chloro-4-[5-methyl-4-(2-nitro-4-trifluoromethyl-phenoxymethyl)-isoxazol-3-yl]-phenyl}-acetic acid methyl ester 22 as part of a mixture of two regioisomers, which is used in the next step without further purification. MS calculated for C$_{21}$H$_{17}$ClF$_3$N$_2$O$_6$ (M+H$^+$) 485.1, found 485.3.

Step C: The crude {3-Chloro-4-[5-methyl-4-(2-nitro-4-trifluoromethyl-phenoxymethyl)-isoxazol-3-yl]-phenyl}-acetic acid methyl ester 22 is dissolved in THF (1 mL), a solution of 1 M LiOH in H$_2$O (0.2 mL) is added and the mixture is stirred overnight at 60° C. The mixture is acidified with 1 M HCl, EtOAc (10 mL) is added and the organic layer washed with H$_2$O (3×5 mL). The organic layer is dried (MgSO$_4$), filtered, concentrated and purified on reverse phase HPLC (H$_2$O/MeCN gradient) to afford the title compound E2 as a white solid: $^1$H-NMR (400 MHz, CDCl$_3$) δ=7.97 (d, J=1.9 Hz, 1H), 7.61 (dd, J=8.8 Hz, J=1.8 Hz, 1H), 7.36 (m, 2H), 7.21 (m, 1H), 6.94 (d, J=8.7 Hz, 1H), 4.94 (s, 2H), 3.63 (s, 2H), 2.51 (s, 3H). MS calculated for C$_{20}$H$_{15}$ClF$_3$N$_2$O$_6$ (M+H$^+$) 471.1, found 471.3

Intermediate 26: [3-Chloro-4-(4-chlorocarbonyl-5-methyl-isoxazol-3-yl)-phenyl]-acetic acid methyl ester.

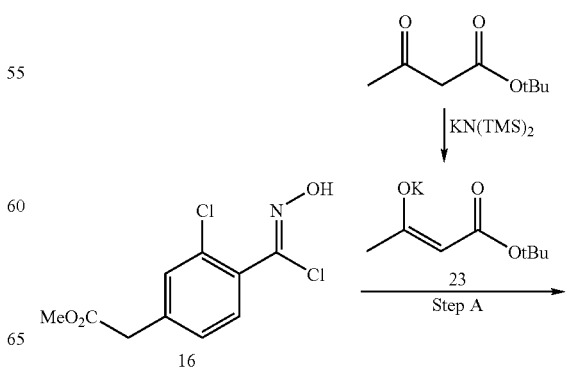

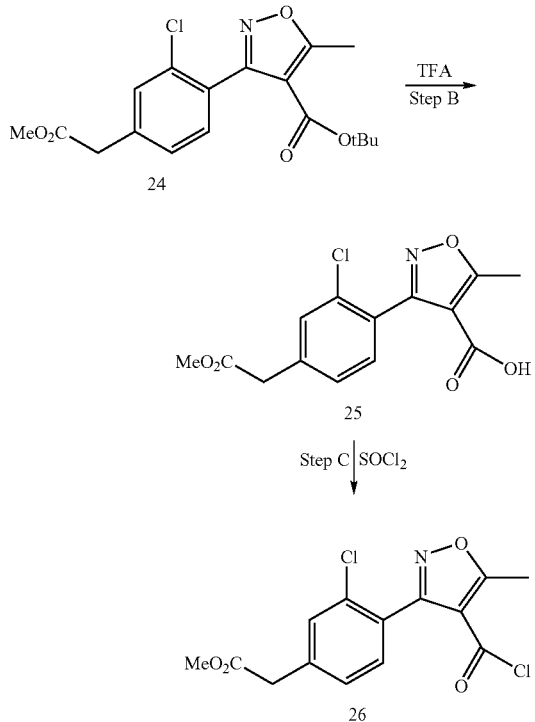

Step A: tert-Butyl acetoacetate (5.0 g, 32 mmol) is dissolved in ether (100 mL). Potassium bis(trimethylsilyl)amide (5.7 g, 29 mmol) is added slowly while stirring at room temperature. Then the mixture is concentrated and triturated with hexane. The precipitate is filtered and dried to yield crude potassium enolate 23 (4.6 g, 23 mmol, 81%). Enolate 23 (1.0 g, 5.0 mmol) is dissolved in MeCN (50 mL) and cooled to 0° C. Intermediate 16 (1.1 g, 4.2 mmol) dissolved in MeCN (10 mL) is added dropwise and the solution is stirred at 0° C. for 2 hours. The solvent is evaporated and the remainder is purified by column chromatography using a hexanes/EtOAc gradient to afford 3-(2-chloro-4-methoxycarbonylmethyl-phenyl)-5-methyl-isoxazole-4-carboxylic acid tert-butyl ester 24 as a white solid: $^1$H-NMR (400 MHz, CDCl$_3$) δ=7.41 (d, J=1.5 Hz, 1H), 7.33 (d, J=7.8 Hz, 1H), 7.25 (dd, J=8.0 Hz, J=1.5 Hz, 1H), 3.69 (s, 3H), 3.65 (s, 2H), 2.73 (s, 3H), 1.28 (s, 9H). MS calculated for C$_{18}$H$_{21}$ClNO$_5$ (M+H$^+$) 366.1, found 366.4.

Step B: 3-(2-chloro-4-methoxycarbonylmethyl-phenyl)-5-methyl-isoxazole-4-carboxylic acid tert-butyl ester 24 (1.0 g, 2.7 mmol) is dissolved in trifluoroacetic acid (20 mL) and stirred at room temperature for 4 hours. Then the solvent is evaporated and the remainder is dried on high vacuum to afford 3-(2-Chloro-4-methoxycarbonylmethyl-phenyl)-5-methyl-isoxazole-4-carboxylic acid 25 as a white solid: $^1$H-NMR (400 MHz, CDCl$_3$) δ=10.36 (s, 1H), 7.42 (s, 1H), 7.36 (d, J=7.8 Hz, 1H), 7.27 (dd, J=8.4 Hz, J=0.6 Hz, 1H), 3.74 (s, 3H), 3.68 (s, 2H), 2.78 (s, 3H). MS calculated for C$_{14}$H$_{13}$ClNO$_5$ (M+H$^+$) 310.0, found 310.3.

Step C: 3-(2-Chloro-4-methoxycarbonylmethyl-phenyl)-5-methyl-isoxazole-4-carboxylic acid 25 (0.6 g, 1.9 mmol) and thionyl chloride (155 μL, 2.1 mmol) are dissolved in toluene (25 mL). The mixture is stirred at 120° C. for 10 hours. Then the reaction mixture is cooled down to 0° C. and triethylamine (600 μL, 3.8 mmol) are added dropwise. The resulting solution containing crude [3-Chloro-4-(4-chlorocarbonyl-5-methyl-isoxazol-3-yl)-phenyl]-acetic acid methyl ester 26 is used without further purification: MS calculated for C$_{14}$H$_{12}$Cl$_2$NO$_4$ (M+H$^+$) 328.0, found 328.2.

Example F1

(3-Chloro-4-{4-[2-(2,4-dichloro-phenoxy)-ethylcarbamoyl]-5-methyl-isoxazol-3-yl}-phenyl)-acetic acid

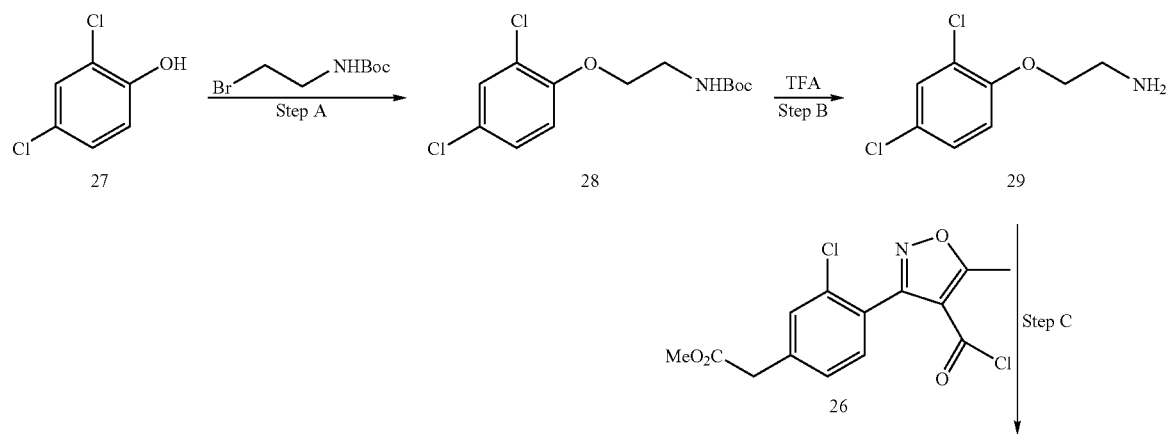

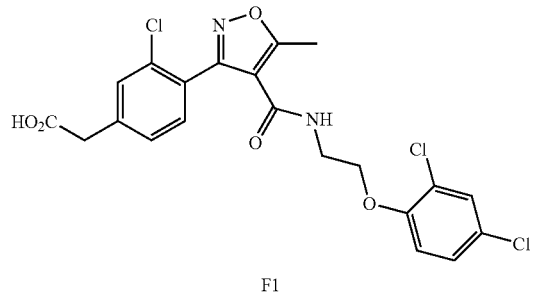

F1

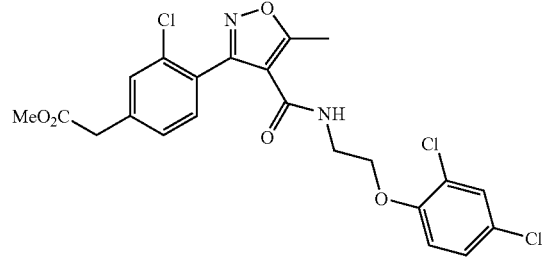

30

Step A: 2,4-Dichloro-phenol 27 (2.0 g, 12.3 mmol) and (2-Bromo-ethyl)-carbamic acid tert-butyl ester (2.75 g, 12.3 mmol) are dissolved in MeCN (40 mL). $Cs_2CO_3$ is added (8.0 g, 24.6 mmol) and the mixture is stirred at 90° C. for 6 hours. The mixture is then filtered, concentrated in vacuo, diluted with $H_2O$ and extracted three times with DCM. The organic layers are combined, dried ($MgSO_4$), filtered, and concentrated and the remainder purified by column chromatography using a DCM/MeOH gradient to afford intermediate 28 as a white solid: $^1$H-NMR (400 MHz, $CDCl_3$) δ=7.37 (d, J=2.5 Hz, 1H), 7.18 (dd, J=8.8 Hz, J=2.5 Hz, 1H), 6.84 (d, J=8.8 Hz, 1H), 5.03 (m, NH), 4.06 (t, J=5.0 Hz, 2H), 3.57 (q, J=5.2 Hz, 2H), 1.45 (s, 9H). MS calculated for $C_9H_{10}Cl_2NO_3$ (M-tBu$^+$) 251.1, found 251.1.

Step B: [2-(2,4-Dichloro-phenoxy)-ethyl]-carbamic acid tert-butyl ester 28 (0.81 g, 2.30 mmol) is dissolved in 60% trifluoroacetic acid in DCM (20 mL) and stirred at room temperature for 1 hour. The mixture is then concentrated, diluted with aqueous sat. $K_2CO_3$ and extracted three times with DCM. The organic layers are combined, dried ($MgSO_4$), filtered, and concentrated to afford intermediate 29 as a white solid: MS calculated for $C_8H_{10}Cl_2NO$ (M+H$^+$) 206.0, found 206.0.

Step C: A solution of 2-(2,4-Dichloro-phenoxy)-ethylamine 29 (17 mg, 0.08 mmol) in toluene (2 mL) is cooled to 0° C. A solution of intermediate 26 (0.08 mmol) and triethylamine (23 μL, 0.16 mmol) in MeCN (1 mL) is added and the solution is warmed to room temperature. After stirring at room temperature for 1 h the mixture is poured into $H_2O$ and extracted three times with EtOAc. The organic layers are combined, dried ($MgSO_4$), filtered, and concentrated to afford crude (3-Chloro-4-{4-[2-(2,4-dichloro-phenoxy)-ethylcarbamoyl]-5-methyl-isoxazol-3-yl}-phenyl)-acetic acid methyl ester 30.

Step D: The crude (3-Chloro-4-{4-[2-(2,4-dichloro-phenoxy)-ethylcarbamoyl]-5-methyl-isoxazol-3-yl}-phenyl)-acetic acid methyl ester 30 is dissolved in THF (2 mL). A solution of 1 M LiOH in $H_2O$ (0.2 mL) and MeOH (25 μL) is added and the mixture is stirred overnight at room temperature. The mixture is acidified with 1 M HCl, EtOAc (10 mL) is added and the organic layer washed with $H_2O$ (3×5 mL). The organic layer is dried ($MgSO_4$), filtered, concentrated and purified on reverse phase HPLC ($H_2O$/MeCN gradient) to afford the title compound F1 as a white solid: $^1$H-NMR (400 MHz, $CDCl_3$) δ=7.40 (d, J=8.2 Hz, 1H), 7.28 (d, J=2.2 Hz, 1H), 7.21-19 (m, 2H), 7.12 (dd, J=8.8 Hz, J=2.5 Hz, 1H), 6.68 (d, J=8.7 Hz, 1H), 5.74 (m, NH), 3.89 (t, J=4.8 Hz, 2H), 3.63 (q, J=5.0 Hz, 2H), 3.45 (s, 2H), 2.69 (s, 3H). MS calculated for $C_{21}H_{18}Cl_3N_2O_5$ (M+H$^+$) 483.0, found 483.3.

Example F2

(3-Chloro-4-{5-methyl-4-[2-(2-nitro-4-trifluoromethyl-phenoxy)-ethylcarbamoyl]-isoxazol-3-yl}-phenyl)-acetic acid

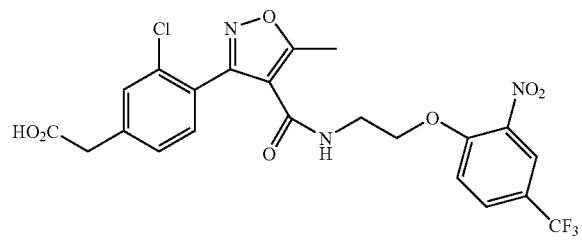

Following the procedure of Example F1, except substituting intermediate 9 for intermediate 29 in Step C, the title compound F2 is prepared as a white solid: $^1$H-NMR (400 MHz, $CDCl_3$) δ=8.39 (s, 1H), 7.98 (m, NH), 7.54 (d, J=8.9 Hz, 1H), 7.29 (m, 2H), 7.17 (m, 1H), 6.75 (d, J=9.1 Hz, 1H), 4.29 (t, J=5.4 Hz, 2H), 3.52 (s, 2H), 3.36 (q, J=5.2 Hz, 2H), 2.70 (s, 3H). MS calculated for $C_{22}H_{18}CF_3N_3O_7$ (M+H$^+$) 528.1, found 528.3.

Intermediate 33

2-(2,4-Bis-trifluoromethyl-phenoxy)-ethylamine

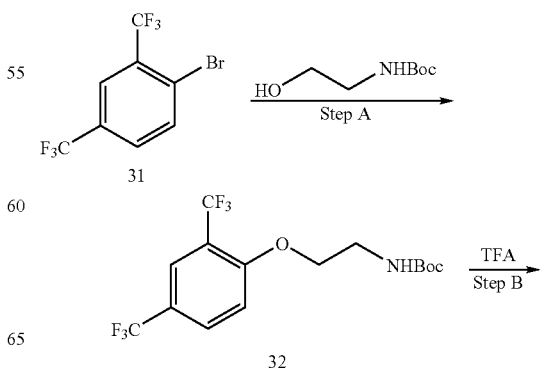

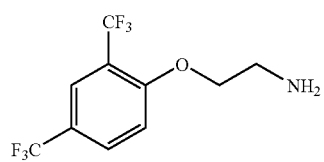

Step A: (2-Hydroxy-ethyl)-carbamic acid tert-butyl ester (0.2 mL, 1.29 mmol) is dissolved in 3 mL dry dimethylacetamide. 2-Potassium-1,1,1,3,3,3-hexamethyl-disilazane (0.52 g, 2.6 mmol, 2 equiv.) is added, followed by 1-bromo-2,4-bis-trifluoromethyl-benzene 31 (0.26 mL, 1.5 mmol, 1.2 equiv.). The mixture is stirred at 60° C. under nitrogen for 18 hours. The mixture is cooled, diluted with 50 mL water and extracted with dichloromethane (3×50 mL). The combined organic extracts are washed with water and 10% aqueous citric acid, dried over $Na_2SO_4$ and concentration. Silica gel chromatography (5% to 25% ethyl acetate in hexanes) yielded [2-(2,4-Bis-trifluoromethyl-phenoxy)-ethyl]-carbamic acid tert-butyl ester 32 as a colorless, mobile oil: $^1$H-NMR (400 MHz, $CDCl_3$) δ=7.61 (s, 1H), 7.00 (d, J=8 Hz, 1H), 6.76 (d, J=8 Hz, 1H), 5.10 (s, 1H), 4.26 (t, J=4 Hz, 2H), 3.65 (m, 2H), 1.45 (s, 9H). $^{19}$F-NMR (376 MHz, $CDCl_3$) δ=−61.5, −62.0. No molecular ion could be obtained; a loss of tert-butyl group is observed: MS calculated for $C_{11}H_{10}F_6NO_3$ (M+H$^+$—$C_4H_8$) 318.1, found 318.3.

Step B: [2-(2,4-Bis-trifluoromethyl-phenoxy)-ethyl]-carbamic acid tert-butyl ester 32 from Step A above (0.23 g, 0.62 mmol) is dissolved in DCM (4 mL) and trifluoroacetic acid (2 mL). After 1 hour, the reaction is completed by LCMS. The mixture is then concentrated, diluted with aqueous saturated $K_2CO_3$ and extracted three times with DCM. The organic layers are combined, dried ($MgSO_4$), filtered, and concentrated to afford intermediate 33 as oil: MS calculated for $C_{10}H_{10}F_6NO$ (M+H$^+$) 274.07, found 274.3.

Example F3

(4-{4-[2-(2,4-Bis-trifluoromethyl-phenoxy)-ethylcarbamoyl]-5-methyl-isoxazol-3-yl}-3-chloro-phenyl)-acetic acid

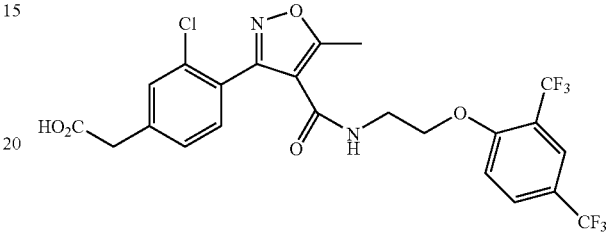

Following the procedure of Example F1, except substituting intermediate 33 for intermediate 29 in Step C, the title compound F3 is prepared as a white solid: $^1$H-NMR (400 MHz, $CDCl_3$) δ=7.73 (s, 1H), 7.70 (d, J=9.0 Hz, 1H), 7.40 (d, J=7.8 Hz, 1H), 7.27 (s, 1H), 7.23 (dd, J=7.7 Hz, J=1.4 Hz, 1H), 6.95 (d, J=8.8 Hz, 1H), 5.63 (m, NH), 4.04 (t, J=5.0 Hz, 2H), 3.65 (q, J=5.1 Hz, 2H), 3.50 (s, 2H), 2.68 (s, 3H). MS calculated for $C_{23}H_{18}ClF_6N_2O_5$ (M+H$^+$) 551.1, found 551.3.

Example G1

(3-Chloro-4-{4-[2-(2,4-dichloro-phenoxy)-ethylcarbamoyl]-5-phenyl-isoxazol-3-yl}-phenyl)-acetic acid

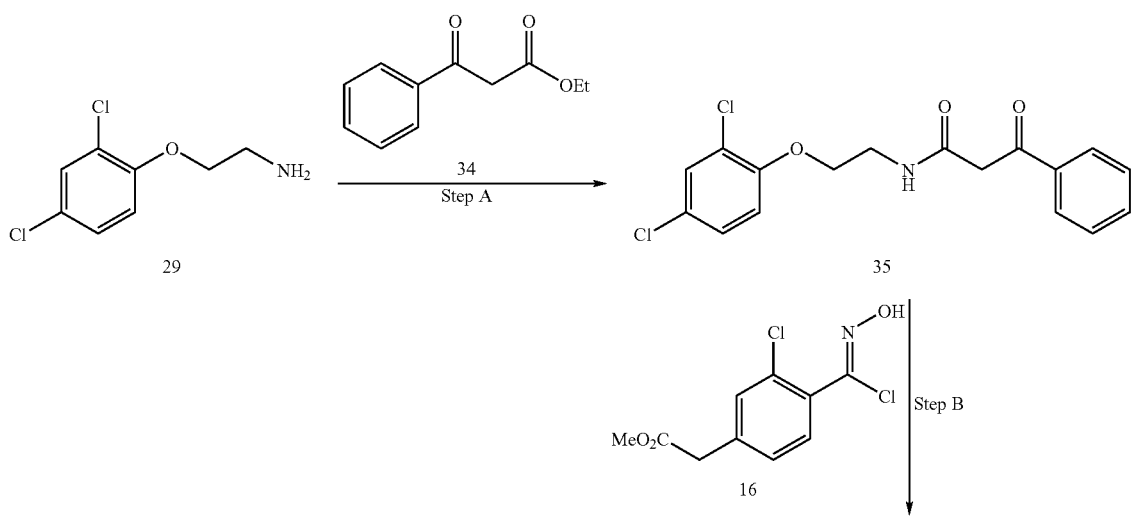

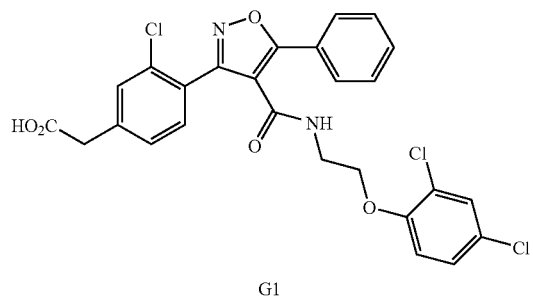

G1

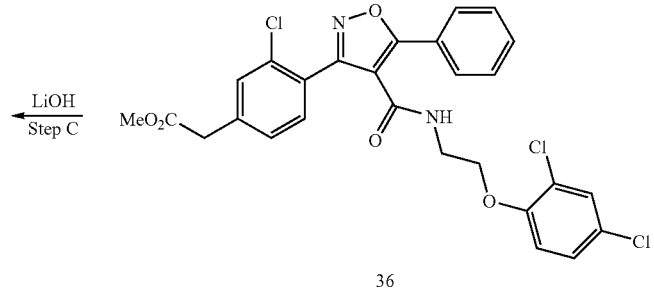

36

Step A: To a solution of 2-(2,4-Dichloro-phenoxy)-ethylamine 29 (412 mg, 2.0 mmol) in toluene (1.5 mL) is added ethyl benzoylacetate 34 (384 mg, 2.0 mmol). The mixture is heated to 160° C. for 10 minutes in a microwave. The resulting mixture is concentrated and purified on reverse phase HPLC ($H_2O$/MeCN gradient) to afford N-[2-(2,4-dichlorophenoxy)-ethyl]-3-oxo-3-phenyl-propionamide 35 as a white solid: $^1$H-NMR (400 MHz, $CDCl_3$) δ=7.98 (d, J=7.2 Hz, 2H), 7.60-7.35 (m, 5H), 7.15 (dd, J=2.5 Hz, J=8.8 Hz, 1H), 6.83 (d, J=8.8 Hz, 1H), 4.10 (t, J=5.2 Hz, 2H), 3.98 (s, 2H), 3.76 (q, J=5.3 Hz, 2H). MS calculated for $C_{17}H_{16}Cl_2NO_3$ (M+H$^+$) 352.0, found 352.1.

Step B: N-[2-(2,4-dichloro-phenoxy)-ethyl]-3-oxo-3-phenyl-propionamide 35 (300 mg, 0.85 mmol) is dissolved in $CH_3CN$ (5 mL). Potassium bis(trimethylsilyl)amide (170 mg, 0.85 mmol) is added slowly while stirring at room temperature. Then the mixture is cooled to 0° C., and a solution of intermediate 16 (0.71 mmol) in $CH_3CN$ (4 mL) is added dropwise. The mixture is stirred at room temperature for 3 hours, then concentrated to afford crude (3-Chloro-4-{4-[2-(2,4-dichloro-phenoxy)-ethylcarbamoyl]-5-phenyl-isoxazol-3-yl}-phenyl)-acetic acid methyl ester 36.

Step C: The crude (3-Chloro-4-{4-[2-(2,4-dichloro-phenoxy)-ethylcarbamoyl]-5-phenyl-isoxazol-3-yl}-phenyl)-acetic acid methyl ester 36 (0.85 mmol) is dissolved in THF (5 mL). A solution of 1 M LiOH in $H_2O$ (2 mL) is added and the mixture is stirred overnight at room temperature. The mixture is acidified with 1 M HCl (3 mL), DCM (50 mL) is added and the organic layer washed with $H_2O$ (3×30 mL). The organic layer is dried ($MgSO_4$), filtered, concentrated and purified on reverse phase HPLC ($H_2O$/MeCN gradient) to afford the title compound G1 as a white solid: $^1$H-NMR (400 MHz, $CDCl_3$) δ=7.93 (dd, J=1.8 Hz, J=7.8 Hz, 2H), 7.52-7.23 (m, 7H), 7.17 (dd, J=8.8 Hz, J=2.5 Hz, 1H), 6.71 (d, J=8.8 Hz, 1H), 6.15 (t, J=5.3 Hz, NH), 3.92 (t, J=4.8 Hz, 2H), 3.72 (q, J=5.3 Hz, 2H), 3.50 (s, 2H). MS calculated for $C_{26}H_{20}Cl_3N_2O_5$ (M+H$^+$) 545.0, found 545.3.

By repeating the procedure described in the above examples, using appropriate starting materials, the following compounds of Formula I are obtained as identified in Table 1.

TABLE 1

| Compound Number | Compound Structure | Physical Data $^1$H NMR 400 MHz (DMSO-$d_6$) and/or MS (m/z) |
|---|---|---|
| G2 | 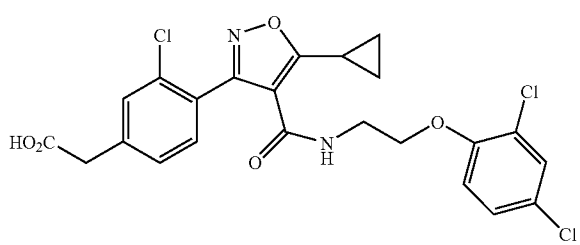 | $^1$H-NMR (400 MHz, $CDCl_3$) δ = 7.46 (d, J = 7.7 Hz, 1H), 7.37 (d, J = 2.5 Hz, 1H), 7.30-7.27 (m, 2H), 7.20 (dd, J = 8.8 Hz, J = 2.5 Hz, 1H), 6.77 (d, J = 8.8 Hz, 1H), 5.92 (t, J = 5.5 Hz, NH), 3.99 (t, J = 4.9 Hz, 2H), 3.74 (q, J = 5.2 Hz, 2H), 3.53 (s, 2H), 2.86 (m, 1H), 1.35 (m, 2H), 1.24 (m, 2H). MS calculated for $C_{23}H_{20}Cl_3N_2O_5$ (M + H$^+$) 509.0, found 509.2. |
| G3 | 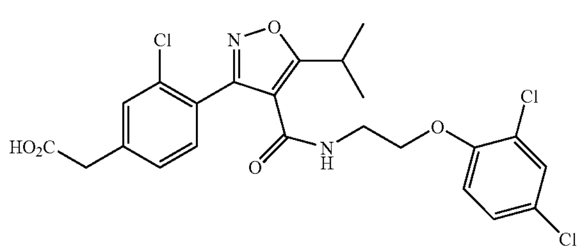 | $^1$H-NMR (400 MHz, $CDCl_3$) δ = 7.49 (d, J = 7.8 Hz, 1H), 7.37 (d, J = 2.5 Hz, 1H), 7.30-7.27 (m, 2H), 7.20 (dd, J = 8.8 Hz, J = 2.5 Hz, 1H), 6.76 (d, J = 8.8 Hz, 1H), 5.85 (t, J = 5.5 Hz, NH), 3.96 (t, J = 4.9 Hz, 2H), 3.84 (m, 1H), 3.72 (q, J = 5.2 Hz, 2H), 3.51 (s, 2H), 1.43 (d, J = 7.0 Hz, 6H). MS calculated for $C_{23}H_{22}Cl_3N_2O_5$ (M + H$^+$) 511.1, found 511.3. |

TABLE 1-continued

| Compound Number | Compound Structure | Physical Data ¹H NMR 400 MHz (DMSO-d$_6$) and/or MS (m/z) |
|---|---|---|
| G4 | 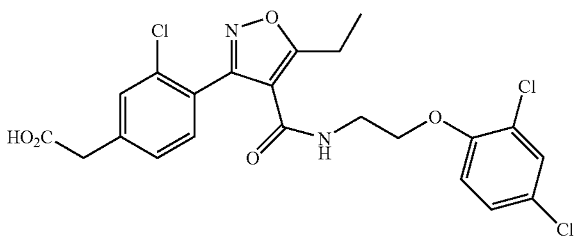 | ¹H-NMR (400 MHz, CDCl$_3$) δ = 7.49 (d, J = 7.6 Hz, 1H), 7.37 (d, J = 2.5 Hz, 1H), 7.31-7.27 (m, 2H), 7.20 (dd, J = 8.8 Hz, J = 2.5 Hz, 1H), 6.76 (d, J = 8.8 Hz, 1H), 5.84 (t, J = 5.5 Hz, NH), 3.97 (t, J = 4.9 Hz, 2H), 3.72 (q, J = 5.2 Hz, 2H), 3.52 (s, 2H), 3.20 (q, J = 7.6 Hz, 2H), 1.41 (t, J = 7.6 Hz, 3H). MS calculated for C$_{22}$H$_{20}$Cl$_3$N$_2$O$_5$ (M + H⁺) 497.0, found 497.2. |
| G5 | 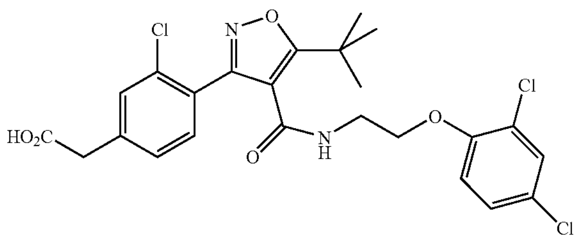 | ¹H-NMR (400 MHz, CDCl$_3$) δ = 7.36 (d, J = 7.9 Hz, 1H), 7.31 (d, J = 2.2 Hz, 1H), 7.13 (s, 2H), 7.11 (s, 1H), 6.63 (d, J = 8.8 Hz, 1H), 6.00 (t, J = 5.5 Hz, NH), 3.80 (t, J = 4.8 Hz, 2H), 3.64 (q, J = 5.1 Hz, 2H), 3.37 (s, 2H), 1.43 (s, 9H). MS calculated for C$_{24}$H$_{24}$Cl$_3$N$_2$O$_5$ (M + H⁺) 525.1, found 525.0. |
| G6 | 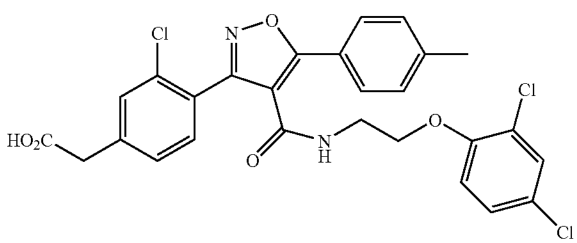 | ¹H-NMR (400 MHz, CDCl$_3$) δ = 7.79 (d, J = 8.0 Hz, 2H), 7.51 (d, J = 7.8 Hz, 1H), 7.34-7.16 (m, 6H), 6.73 (d, J = 8.8 Hz, 1H), 6.18 (t, J = 5.5 Hz, NH), 3.94 (t, J = 4.8 Hz, 2H), 3.74 (q, J = 5.1 Hz, 2H), 3.53 (s, 2H), 2.37 (s, 3H). MS calculated for C$_{27}$H$_{22}$Cl$_3$N$_2$O$_5$ (M + H⁺) 559.1, found 559.0. |
| G7 | 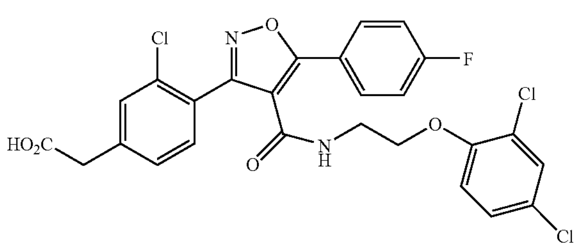 | ¹H-NMR (400 MHz, CDCl$_3$) δ = 8.24 (m, 2H), 7.74 (d, J = 7.8 Hz, 1H), 7.58-7.35 (m, 6H), 6.94 (d, J = 8.8 Hz, 1H), 6.32 (t, J = 5.5 Hz, NH), 4.14 (t, J = 4.8 Hz, 2H), 3.96 (q, J = 5.1 Hz, 2H), 3.72 (s, 2H). MS calculated for C$_{26}$H$_{19}$Cl$_3$FN$_2$O$_5$ (M + H⁺) 563.0, found 563.0. |
| G8 | 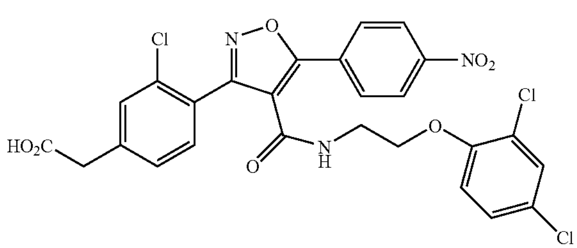 | ¹H-NMR (400 MHz, CDCl$_3$) δ = 8.31 (d, J = 8.9 Hz, 2H), 8.24 (d, J = 8.9 Hz, 2H), 7.54 (d, J = 8.2 Hz, 1H), 7.34-7.18 (m, 4H), 6.71 (d, J = 8.8 Hz, 1H), 6.12 (t, J = 5.5 Hz, NH), 3.92 (t, J = 4.7 Hz, 2H), 3.76 (q, J = 5.0 Hz, 2H), 3.49 (s, 2H). MS calculated for C$_{26}$H$_{19}$Cl$_3$N$_3$O$_7$ (M + H⁺) 590.0, found 590.0. |
| G9 | 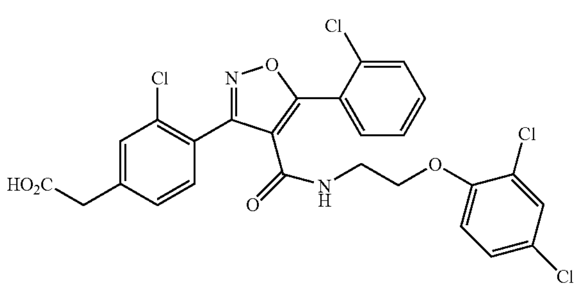 | ¹H-NMR (400 MHz, CDCl$_3$) δ = 7.47-6.99 (m, 9H), 6.53 (d, J = 8.8 Hz, 1H), 5.91 (t, J = 5.5 Hz, NH), 3.75 (t, J = 4.7 Hz, 2H), 3.50 (q, J = 5.1 Hz, 2H), 3.43 (s, 2H). MS calculated for C$_{26}$H$_{19}$Cl$_4$N$_2$O$_5$ (M + H⁺) 579.0, found 579.0. |

TABLE 1-continued

| Compound Number | Compound Structure | Physical Data $^1$H NMR 400 MHz (DMSO-$d_6$) and/or MS (m/z) |
|---|---|---|
| G10 | 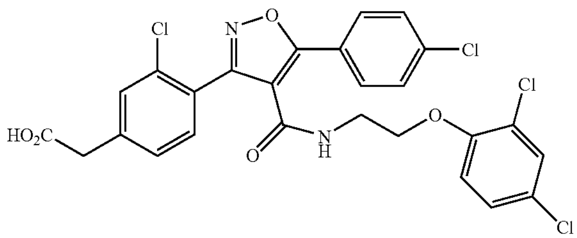 | $^1$H-NMR (400 MHz, CDCl$_3$) δ = 7.94 (d, J = 8.6 Hz, 2H), 7.52 (d, J = 11.8 Hz, 1H), 7.42 (d, J = 8.6 Hz, 2H), 7.36-7.18 (m, 4H), 6.71 (d, J = 8.8 Hz, 1H), 6.10 (t, J = 5.5 Hz, NH), 3.93 (t, J = 4.8 Hz, 2H), 3.74 (q, J = 5.1 Hz, 2H), 3.51 (s, 2H). MS calculated for C$_{26}$H$_{19}$Cl$_4$N$_2$O$_5$ (M + H$^+$) 579.0, found 579.0. |
| G11 | 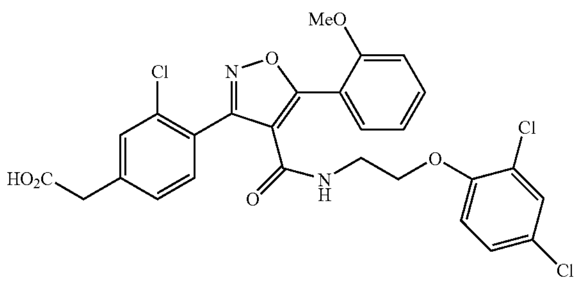 | $^1$H-NMR (400 MHz, CDCl$_3$) δ = 7.67 (d, J = 2.6 Hz, 1H), 7.65 (d, J = 2.6 Hz, 1H), 7.61-7.12 (m, 6H), 6.99 (d, J = 8.4 Hz, 1H), 6.76 (d, J = 8.8 Hz, 1H), 6.56 (t, J = 5.5 Hz, NH), 3.99 (t, J = 4.8 Hz, 2H), 3.87 (s, 3H), 3.73 (q, J = 5.2 Hz, 2H), 3.65 (s, 2H). MS calculated for C$_{27}$H$_{21}$Cl$_3$N$_2$O$_6$ (M + H$^+$) 575.1, found 575.0. |
| G12 | 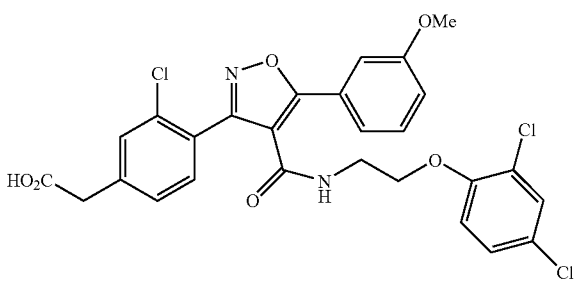 | $^1$H-NMR (400 MHz, CDCl$_3$) δ = 7.61-7.12 (m, 9H), 6.71 (d, J = 8.8 Hz, 1H), 6.19 (t, J = 5.5 Hz, NH), 3.93 (t, J = 4.8 Hz, 2H), 3.83 (s, 3H), 3.74 (q, J = 5.2 Hz, 2H), 3.53 (s, 2H). MS calculated for C$_{27}$H$_{21}$Cl$_3$N$_2$O$_6$ (M + H$^+$) 575.1, found 575.0. |
| G13 | 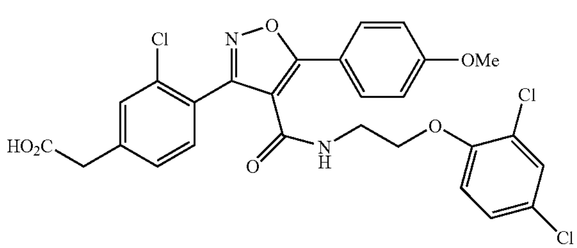 | $^1$H-NMR (400 MHz, CDCl$_3$) δ = 7.90 (d, J = 8.9 Hz, 2H), 7.51 (d, J = 7.8 Hz, 1H), 7.34-6.96 (m, 5H), 6.94 (d, J = 8.9 Hz, 2H), 6.72 (d, J = 8.8 Hz, 1H), 6.15 (t, J = 5.5 Hz, NH), 3.93 (t, J = 4.8 Hz, 2H), 3.83 (s, 3H), 3.74 (q, J = 5.2 Hz, 2H), 3.52 (s, 2H). MS calculated for C$_{27}$H$_{21}$Cl$_3$N$_2$O$_6$ (M + H$^+$) 575.1, found 575.0. |
| G14 | 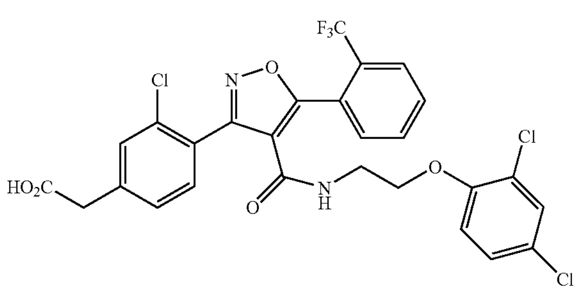 | $^1$H-NMR (400 MHz, CDCl$_3$) δ = 7.80 (d, J = 7.7 Hz, 1H), 7.67-7.16 (m, 8H), 6.68 (d, J = 8.8 Hz, 1H), 5.89 (t, J = 5.5 Hz, NH), 3.85 (t, J = 4.8 Hz, 2H), 3.62 (q, J = 5.2 Hz, 2H), 3.60 (s, 2H). MS calculated for C$_{27}$H$_{19}$Cl$_3$F$_3$N$_2$O$_5$ (M + H$^+$) 613.0, found 613.0. |

TABLE 1-continued

| Compound Number | Compound Structure | Physical Data $^1$H NMR 400 MHz (DMSO-$d_6$) and/or MS (m/z) |
|---|---|---|
| G15 | 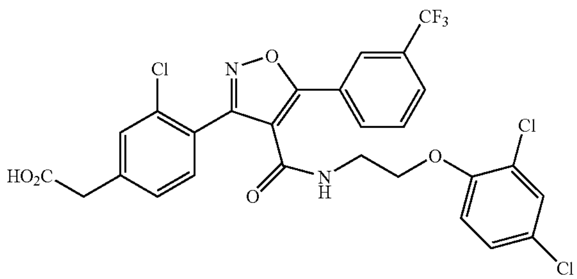 | $^1$H-NMR (400 MHz, CDCl$_3$) δ = 8.26 (s, 1H), 8.16 (d, J = 8.0 Hz, 1H), 7.71 (d, J = 7.9 Hz, 1H), 7.58-7.12 (m, 6H), 6.67 (d, J = 8.8 Hz, 1H), 6.08 (t, J = 5.5 Hz, NH), 3.88 (t, J = 4.8 Hz, 2H), 3.70 (q, J = 5.2 Hz, 2H), 3.46 (s, 2H). MS calculated for C$_{27}$H$_{19}$Cl$_3$F$_3$N$_2$O$_5$ (M + H$^+$) 613.0, found 613.0. |
| G16 | 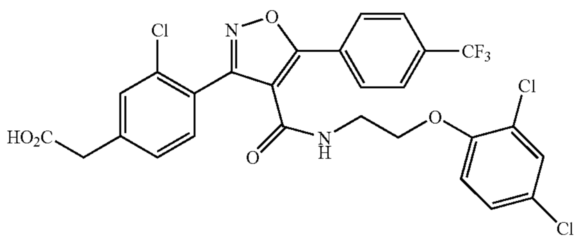 | $^1$H-NMR (400 MHz, CDCl$_3$) δ = 8.23 (d, J = 8.3 Hz, 2H), 7.82 (d, J = 8.3 Hz, 2H), 7.62 (d, J = 7.7 Hz, 1H), 7.44-7.27 (m, 4H), 6.81 (d, J = 8.8 Hz, 1H), 6.24 (t, J = 5.5 Hz, NH), 4.02 (t, J = 4.8 Hz, 2H), 3.84 (q, J = 5.2 Hz, 2H), 3.59 (s, 2H). MS calculated for C$_{27}$H$_{19}$Cl$_3$F$_3$N$_2$O$_5$ (M + H$^+$) 613.0, found 613.0. |
| G17 | 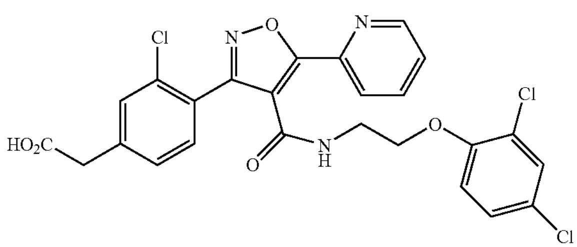 | $^1$H-NMR (400 MHz, CDCl$_3$) δ = 8.69 (d, J = 4.7 Hz, 1H), 8.20 (d, J = 8.0 Hz, 1H), 8.04-7.14 (m, 7H), 6.83 (d, J = 8.8 Hz, 1H), 5.74 (m, NH), 4.15 (t, J = 4.8 Hz, 2H), 3.85 (m, 2H), 3.68 (s, 2H). MS calculated for C$_{25}$H$_{19}$Cl$_3$N$_3$O$_5$ (M + H$^+$) 546.0, found 546.0. |
| G18 | 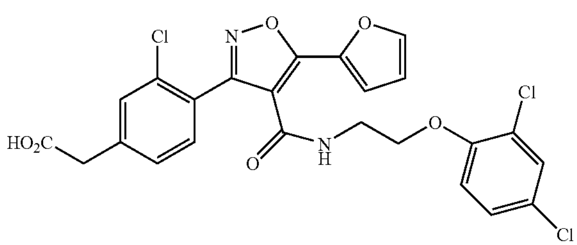 | $^1$H-NMR (400 MHz, CDCl$_3$) δ = 7.64-7.22 (m, 7H), 6.83 (d, J = 8.8 Hz, 1H), 6.72 (t, J = 5.5 Hz, NH), 6.65 (m, 1H), 4.08 (t, J = 4.8 Hz, 2H), 3.84 (q, J = 5.2 Hz, 2H), 3.61 (s, 2H). MS calculated for C$_{24}$H$_{18}$Cl$_3$N$_2$O$_6$ (M + H$^+$) 535.0, found 535.0. |
| G19 | 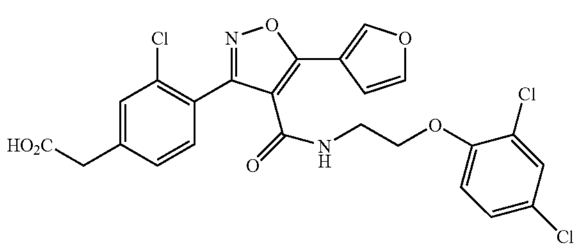 | $^1$H-NMR (400 MHz, CDCl$_3$) δ = 8.60 (s, 1H), 7.55-7.06 (m, 7H), 6.75 (d, J = 8.8 Hz, 1H), 5.94 (t, J = 5.5 Hz, NH), 3.96 (t, J = 4.8 Hz, 2H), 3.75 (q, J = 5.2 Hz, 2H), 3.49 (s, 2H). MS calculated for C$_{24}$H$_{18}$Cl$_3$N$_2$O$_6$ (M + H$^+$) 535.0, found 535.0. |

Example H1

[3-Chloro-4-(4-{[2-(2,4-dichloro-phenoxy)-ethyl]-methyl-carbamoyl}-5-phenyl-isoxazol-3-yl)-phenyl]-acetic acid

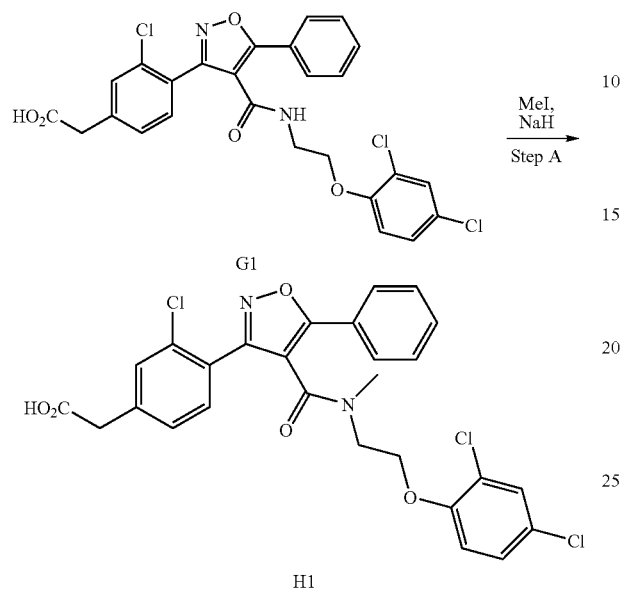

Step A: To a solution of example G1 (50 mg, 0.092 mmol) in DMF (1.5 mL) is added NaH (60% dispersion, 7.4 mg, 0.18 mmol) at 0° C. The mixture is stirred at 0° C. for 10 minutes, then MeI (10 uL, 0.14 mmol) is added and the mixture is stirred at room temperature for 30 minutes. The resulting mixture is concentrated and purified on reverse phase HPLC ($H_2O$/MeCN gradient) to afford [3-Chloro-4-(4-{[2-(2,4-dichloro-phenoxy)-ethyl]-methyl-carbamoyl}-5-phenyl-isoxazol-3-yl)-phenyl]-acetic acid H1 as a white solid: $^1$H-NMR (400 MHz, $CDCl_3$) δ=7.69 (d, J=7.5 Hz, 2H), 7.45-7.10 (m, 8H), 6.73 (d, J=8.8 Hz, 1H), 4.11 (m, 2H), 3.61 (m, 2H), 3.49 (s, 2H), 2.95 (s, 3H). MS calculated for $C_{27}H_{22}Cl_3N_2O_5$ (M+H$^+$) 559.1, found 559.1.

Example H2

(3-Chloro-4-{4-[2-(2,4-dichloro-phenoxy)-ethoxymethyl]-5-phenyl-isoxazol-3-yl}-phenyl)-acetic acid

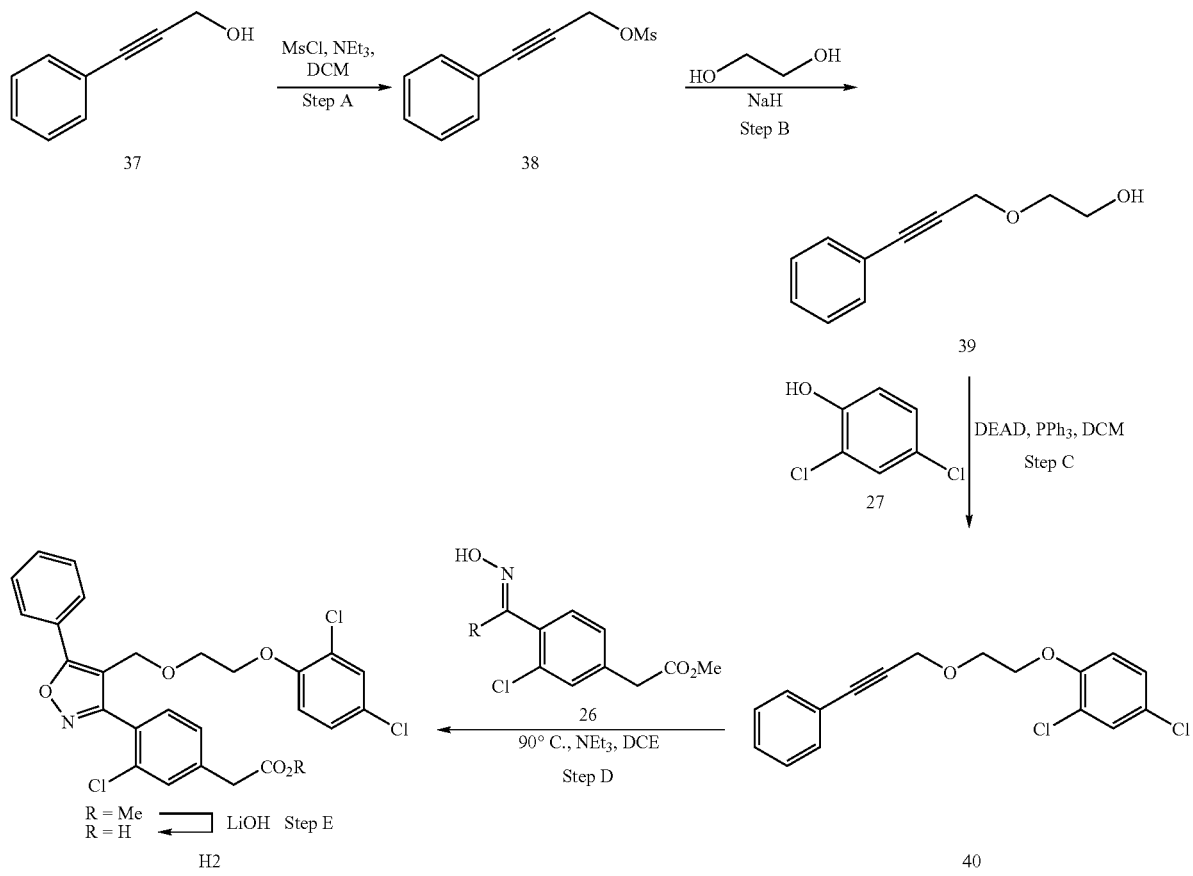

Step A: 3-Phenyl-prop-2-yn-1-ol 37 (3.0 g, 22.7 mmol) is dissolved in DCM (50 mL). The solution is cooled to 0° C., then methanesulfonyl chloride (4.5 mL, 34.1 mmol) and triethyl amine (4.7 mL, 34.1 mmol) is added. The mixture is allowed to warm to room temperature and stirred overnight at room temperature. The mixture is washed with $H_2O$ (2×30 mL). The organic layer is dried ($MgSO_4$), filtered, and concentrated to afford crude methanesulfonic acid 3-phenyl-prop-2-ynyl ester 38 as a clear oil: $^1$H-NMR (400 MHz, $CDCl_3$) δ=7.47-7.32 (m, 5H), 4.38 (s, 2H), 3.67 (s, 3H).

Step B: Sodium hydride (60% dispersion, 250 mg, 17.4 mmol) is suspended in ethylene glycol (10 mL) and stirred for 20 minutes at room temperature. To the resulting solution is added mesylate 38 (1.0 g, 4.8 mmol) and the mixture is heated to 100° C. overnight. The mixture is diluted with DCM (120 mL) and washed with $H_2O$ (2×60 mL). The organic layer is dried ($MgSO_4$), filtered, concentrated and purified by column chromatography using a DCM/MeOH gradient to afford intermediate 39 as a yellow oil: $^1$H-NMR (400 MHz, $CDCl_3$) δ=7.46-7.30 (m, 5H), 4.43 (s, 2H), 3.80 (t, J=4.5 Hz, 2H), 3.72 (t, J=4.5 Hz, 2H), 2.12 (s, OH). MS calculated for $C_{11}H_{13}O_2$ (M+H$^+$) 177.1, found 177.1.

Step C: Intermediate 39 (0.30 g, 1.7 mmol), 2,4-dichlorophenol 27 (0.33 g, 2.0 mmol) and triphenyl phosphine (0.89 g, 3.4 mmol) is dissolved in DCM (25 mL). Diethyl azodicarboxylate (0.61 mL, 2.6 mmol) is added and the solution is stirred at room temperature for 4 hours. The crude mixture is purified by column chromatography using a DCM/MeOH gradient to afford intermediate 40 as an oil: $^1$H-NMR (400 MHz, $CDCl_3$) δ=7.46-6.88 (m, 8H), 4.53 (s, 2H), 4.23 (t, J=4.8 Hz, 2H), 4.01 (t, J=4.8 Hz, 2H). MS calculated for $C_{17}H_{15}Cl_2O_2$ (M+H$^+$) 321.0, found 321.0.

Step D: Intermediate 26 (0.20 g, 0.75 mmol) is dissolved in DCE (5 mL). Triethylamine (125 μL, 0.9 mmol) is added and a precipitate forms. Intermediate 40 (0.24 g, 0.75 mmol) is added and the mixture is stirred at 90° C. for 16 hours. The solvent is removed in vacuo and the remainder (crude intermediate 41 as a mixture of regioisomers) is used in the next step without further purification.

Step E: (3-Chloro-4-{4-[2-(2,4-dichloro-phenoxy)-ethoxymethyl]-5-phenyl-isoxazol-3-yl}-phenyl)-acetic acid methyl ester 41 (0.75 mmol) is dissolved in THF (5 mL). A solution of 1 M LiOH in $H_2O$ (3.5 mL) is added and the mixture is stirred for 6 hours at room temperature. The mixture is acidified with 1 M HCl (3 mL), DCM (50 mL) is added and the organic layer washed with $H_2O$ (2×30 mL). The organic layer is dried ($MgSO_4$), filtered, concentrated and purified on reverse phase HPLC ($H_2O$/MeCN gradient) to afford the title compound H2 as a white solid: $^1$H-NMR (400 MHz, $CDCl_3$) δ=7.84 (m, 2H), 7.44-7.19 (m, 7H), 7.06 (dd, J=8.8 Hz, J=2.5 Hz, 1H), 6.70 (d, J=8.8 Hz, 1H), 4.45 (s, 2H), 4.00 (t, J=4.5 Hz, 2H), 3.71 (t, J=4.5 Hz, 2H), 3.62 (s, 2H). MS calculated for $C_{26}H_{21}Cl_3NO_5$ (M+H$^+$) 532.0, found 532.1.

Example H3

(3-Chloro-4-{4-[4-(2,4-dichloro-phenoxy)-butyryl]-5-phenyl-isoxazol-3-yl}-phenyl)-acetic acid

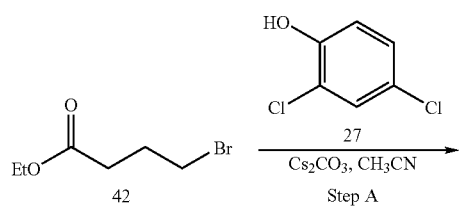

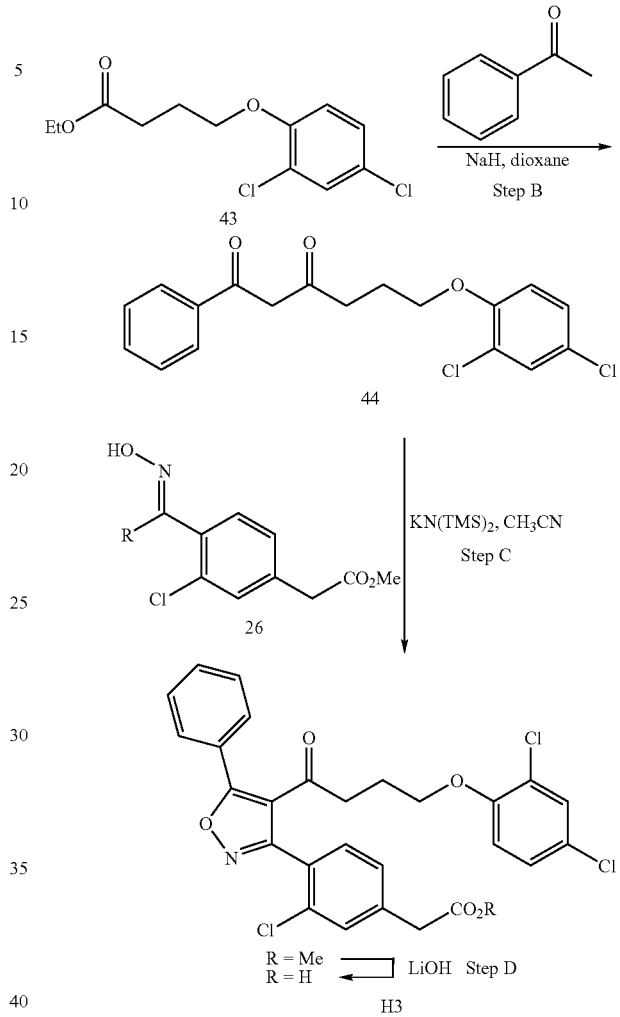

Step A: Ethyl-4-bromobutyrate 42 (1.0 g, 5.1 mmol) and 2,4-dichlorophenol 27 (0.84 g, 5.1 mmol) is dissolved in MeCN (50 mL). $Cs_2CO_3$ is added and the suspension is stirred at 50° C. for 7 hours. The mixture is then filtered, concentrated in vacuo, diluted with $H_2O$ and extracted three times with EtOAc. The organic layers are combined, dried ($MgSO_4$), filtered, and concentrated to afford intermediate 43 as an oil: $^1$H-NMR (400 MHz, $CDCl_3$) δ=7.27 (d, J=2.5 Hz, 1H), 7.08 (dd, J=2.5 Hz, J=8.8 Hz, 1H), 6.76 (d, J=8.8 Hz, 1H), 4.07 (q, J=7.1 Hz, 2H), 3.98 (t, J=6.1 Hz, 2H), 2.48 (t, J=7.2 Hz, 2H), 2.07 (m, 2H), 1.18 (t, J=7.1 Hz, 3H). MS calculated for $C_{12}H_{15}Cl_2O_3$ (M+H$^+$) 277.0, found 277.1.

Step B: Sodium hydride (60% dispersion, 560 mg, 14 mmol) is dissolved in dioxane (30 mL) and stirred vigorously for 10 min at room temperature. To the vigorously stirring solution is added acetophenone (dropwise) (0.54 mL, 4.7 mmol) and intermediate 43 (1.29 g, 4.7 mmol) dissolved in dioxane (10 mL). The mixture is heated to reflux for 3 hours, then cooled to room temperature and poured into a cold solution of 0.5 M HCl (100 mL). EtOAc (200 mL) is added and the organic layer is washed with $H_2O$ and brine (2×100 mL). The organic layer is dried ($MgSO_4$), filtered, concentrated and purified by column chromatography using a hexanes/EtOAc gradient to afford intermediate 44 as an oil: MS calculated for $C_{18}H_{17}Cl_2O_3$ (M+H$^+$) 351.0, found 351.1.

Step C: Intermediate 44 (0.20 g, 0.57 mmol) is dissolved in MeCN (5 mL). Potassium bis(trimethylsilyl)amide (270 mg, 1.36 mmol) is added slowly while stirring at room temperature. Then the mixture is cooled to 0° C., and a solution of intermediate 16 (0.71 mmol) in CH$_3$CN (4 mL) is added dropwise. The mixture is stirred at room temperature for 3 hours, then concentrated to afford crude (3-Chloro-4-{4-[2-(2,4-dichloro-phenoxy)-ethyl-carbamoyl]-5-phenyl-isoxazol-3-yl}-phenyl)-acetic acid methyl ester 45 as a mixture of regioisomers. MS calculated for C$_{28}$H$_{23}$Cl$_3$N$_2$O$_5$ (M+H$^+$) 558.1, found 558.1.

Step D: Crude (3-Chloro-4-{4-[2-(2,4-dichloro-phenoxy)-ethylcarbamoyl]-5-phenyl-isoxazol-3-yl}-phenyl)-acetic acid methyl ester 45 is dissolved in THF (5 mL). A solution of 1 M LiOH in H$_2$O (3.5 mL) is added and the mixture is stirred for 6 h at room temperature. The mixture is acidified with 1 M HCl (3 mL), DCM (50 mL) is added and the organic layer washed with H$_2$O (2×30 mL). The organic layer is dried (MgSO$_4$), filtered, concentrated and purified on reverse phase HPLC (H$_2$O/MeCN gradient) to afford the title compound H2 as a white solid (minor isomer!): $^1$H-NMR (400 MHz, CDCl$_3$) δ=7.65 (d, J=7.0 Hz, 2H), 7.39-6.93 (m, 8H), 6.54 (d, J=8.8 Hz, 1H), 3.72 (t, J=5.9 Hz, 2H), 3.53 (s, 2H), 2.50 (t, J=6.8 Hz, 2H), 1.88 (m, 2H). MS calculated for C$_{27}$H$_{21}$Cl$_3$N$_2$O$_5$ (M+H$^+$) 544.0, found 544.1.

Example I1

(5-{4-[2-(2,4-Dichloro-phenoxy)-ethyl-carbamoyl]-5-phenyl-isoxazol-3-yl}-phenyl)-acetic acid

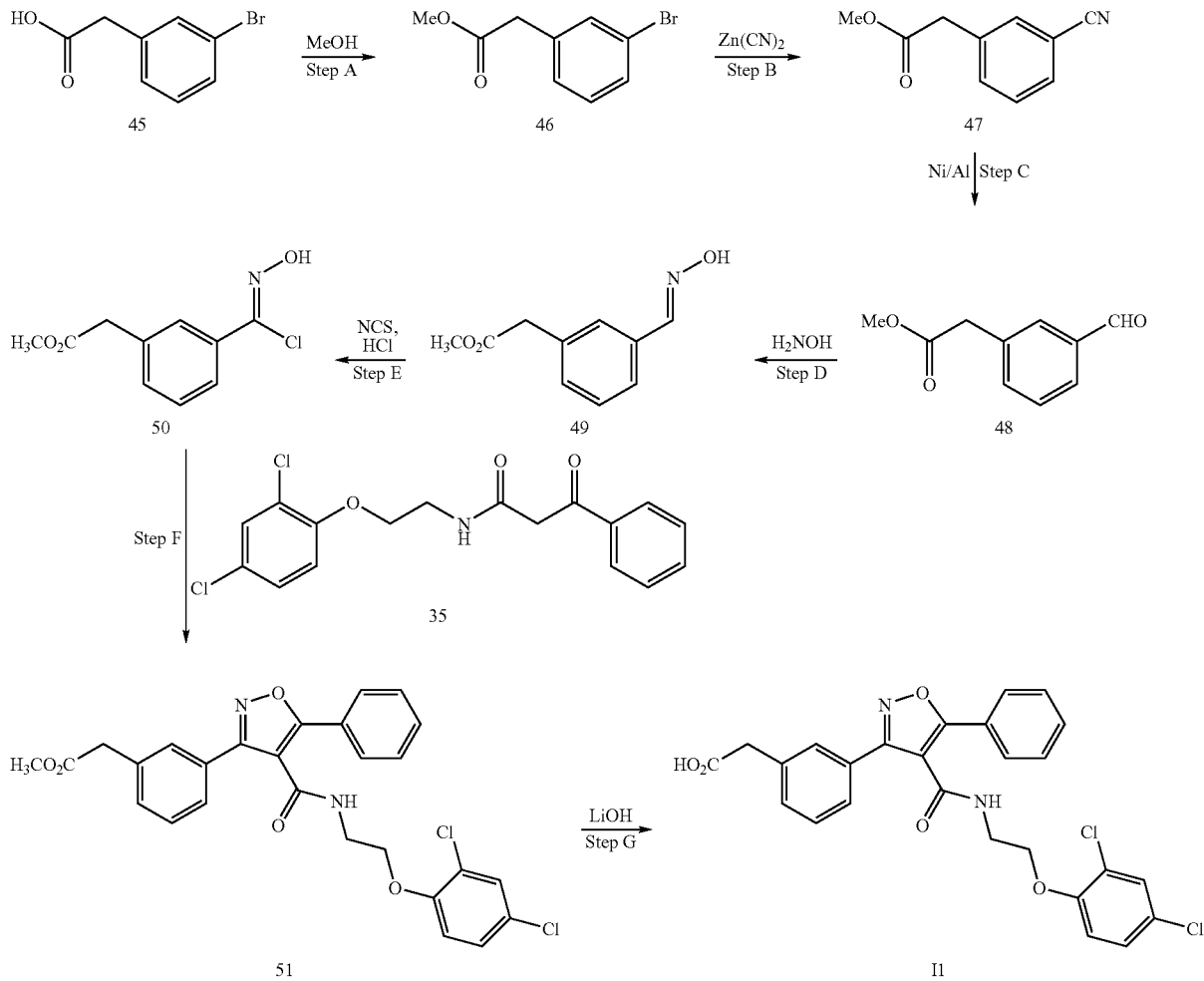

Step A: 3-Bromophenyl acetic acid 45 (1.17 g, 5.44 mmol) is dissolved in MeOH (15 mL) containing catalytic amounts of conc. H$_2$SO$_4$ (0.2 mL). The solution is heated to reflux overnight. The solvent is evaporated, the remainder is dissolved in DCM and washed with water and saturated aqueous NaHCO$_3$. The organic layer is dried (MgSO$_4$), filtered and concentrated to afford the methyl ester 46 as an oil: $^1$H-NMR (400 MHz, CDCl$_3$) δ=7.44 (s, 1H), 7.40 (ddd, J=2.0, 2.4, 6.8 Hz, 1H), 7.20 (m, 2H), 3.70 (s, 3H), 3.59 (s, 2H). MS calculated for C$_9$H$_{10}$BrO$_2$ (M+H$^+$) 229.1, found 229.0.

Step B: To a solution of (3-bromophenyl)-acetic acid methyl ester 46 (1.20 g, 5.28 mmol) in dry dimethyl-acetamide (5 mL) is added under argon zinc cyanide (0.78 g, 6.64 mmol) and tetrakis(triphenylphosphine) palladium (0.63 g, 0.55 mmol). The mixture is stirred for 24 hours at 80° C. After cooling to room temperature, the mixture is diluted with EtOAc (15 mL) and water (20 mL). The resulting precipitate is removed by vacuum filtration. The organic layer of the filtrate is separated and washed with $H_2O$, then dried over $MgSO_4$, filtered and concentrated. Purification by silica gel chromatography (0 to 20% EtOAc/hexane) to give (3-cyanophenyl)acetic acid methyl ester 47 as an oil: $^1$H-NMR (400 MHz, $CDCl_3$) δ=7.63 (d, J=8.0 Hz, 1H), 7.47 (d, J=1.2 Hz, 1H), 7.30 (dd, J=1.2 Hz, J=8.0 Hz, 1H), 3.72 (s, 3H), 3.69 (s, 2H). MS calculated for $C_{10}H_9O_2ClN$ (M+H$^+$) 210.0, found 210.0.

Step C: A solution of (3-cyanophenyl)acetic acid methyl ester 47 (0.86 g, 4.9 mmol) in 88% formic acid (6 mL) is combined with Raney nickel alloy (0.48 g) and heated to reflux for 24 hours at 110° C. After cooling to room temperature, the alloy is removed by filtration over Celite. The filtrate is concentrated to ~10% of the original volume and diluted with EtOAc (50 mL) and washed three times with water (20 mL). The organic layer is dried (MgSO$_4$), filtered and concentrated to afford crude product, which is purified by silica gel chromatography using an EtOAc/hexane gradient to give (3-formylphenyl)-acetic acid methyl ester 48 as an oil: $^1$H-NMR (400 MHz, $CDCl_3$) δ=9.97 (s, 1H), 7.40-7.52 (m, 4H), 3.68 (s, 3H), 3.67 (s, 2H). MS calculated for $C_{10}H_{11}O_3$ (M+H$^+$) 179.1, found 179.1.

Step D: (3-Formylphenyl)-acetic acid methyl ester 48 (0.28 g, 1.6 mmol) is dissolved in dimethoxy-ethane (5 mL). Hydroxy-amine hydrochloride (0.11 g, 1.58 mmol) is added, followed by ethyl-diisopropylamine (0.3 mL, 1.7 mmol). The mixture is stirred at room temperature for 2 hours. The solvent is removed in vacuo and the residue is extracted three times with dichloromethane. The organic layers are combined, dried over MgSO$_4$, filtered, and concentrated to afford the oxime 49 as a white solid: $^1$H-NMR (400 MHz, $CDCl_3$) δ=8.12 (s, 1H), 7.65-7.70 (m, 4H), 3.70 (s, 3H), 3.64 (s, 2H). MS calculated for $C_{10}H_{12}NO_3$ (M+H$^+$) 194.1, found 104.1.

Step E: [3-(Hydroxyimino-methyl)-phenyl]-acetic acid methyl ester 49 (0.3 g, 1.6 mmol) and N-chlorosuccinimide (0.27 g, 2.0 mmol) are dissolved in DME (4 mL). After adding catalytic amounts of HCl (4M solution in dioxane) to the solution, an exothermic reaction occurred. After stirring for 2 hours at room temperature, the mixture is diluted with $H_2O$ and extracted three times with ethyl acetate to afford intermediate 50 as a semi-solid; a stock solution is made in DME; MS calculated for $C_{10}H_{11}ClNO_3$ (M+H$^+$) 228.1, found 228.0.

Step F: A solution of N-[2-(2,4-Dichloro-phenoxy)-ethyl]-3-oxo-3-phenyl-propionamide 35 (0.11 g, 0.3 mmol) in DME (4 mL) is cooled to –20° C. Potassium t-butoxide (0.6 mL of a 1.0 M solution in THF) is added and the solution is stirred for 20 minutes at –20° C. Intermediate 50 (0.07 g, 0.3 mmol) is added as a solution in 1 mL DME. The mixture is stirred for 30 minutes at –20° C., then it is warmed to room temperature. After stirring at room temperature for 1 hour the mixture is poured into $H_2O$ and extracted three times with EtOAc. The organic layers are combined, dried (MgSO4), filtered, and concentrated to afford crude (3-{4-[2-(2,4-dichloro-phenoxy)-ethyl-carbamoyl]-5-phenyl-isoxazol-3-yl}-phenyl)-acetic acid methyl ester 51.

Step G: The crude (3-{4-[2-(2,4-dichloro-phenoxy)-ethyl-carbamoyl]-5-phenyl-isoxazol-3-yl}-phenyl)-acetic acid methyl ester 51 is dissolved in DME (2 mL). A solution of 1 M LiOH in $H_2O$ (0.2 mL) and is added and the mixture is stirred overnight at room temperature. The mixture is concentrated, then acidified with 1 M HCl, extracted with EtOAc (10 mL), dried over MgSO$_4$, filtered, concentrated and purified on reverse phase HPLC ($H_2O$/MeCN gradient) to afford the title compound I1 as an off-white solid: $^1$H-NMR (400 MHz, CD$_3$CN) δ=7.61 (s, 1H), 7.57 (m, 1H), 7.38 (m, 5H), 7.33 (d, J=2.4 Hz, 1H), 7.28 (m, 2H), 7.20 (dd, J=9.2, 2.8 Hz, 1H), 7.16 (t, J=5.2 Hz, NH), 6.90 (d, J=8.8 Hz, 1H), 4.04 (t, J=5.2 Hz, 2H), 3.63 (q, J=5.2 Hz, 2H), 3.59 (s, 2H). MS calculated for $C_{26}H_{21}Cl_2N_2O_5$ (M+H$^+$) 511.0, found 511.0.

By repeating the procedure described in the above examples, using appropriate starting materials, the following compounds of Formula I are obtained as identified in Table 2.

TABLE 2

| Compound Number | Compound Structure | Physical Data $^1$H NMR 400 MHz and/or MS (m/z) |
|---|---|---|
| I2 | 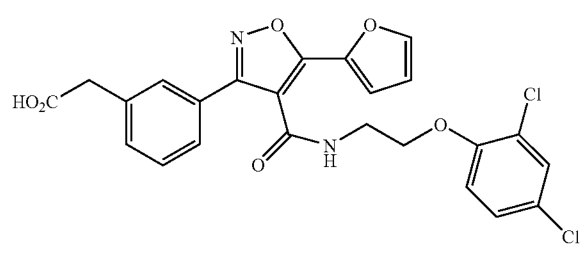 | $^1$H-NMR (400 MHz, d$^6$-DMSO) δ = 9.06 (1H), 7.92 (1H), 7.66-7.16 (m, 7H), 6.68 (1H), 4.20 (2H), 3.63 (2H), 3.62 (2H). MS calculated for $C_{24}H_{19}Cl_2N_2O_6$ (M + H$^+$) 501.1, found 501.0. |
| I3 | 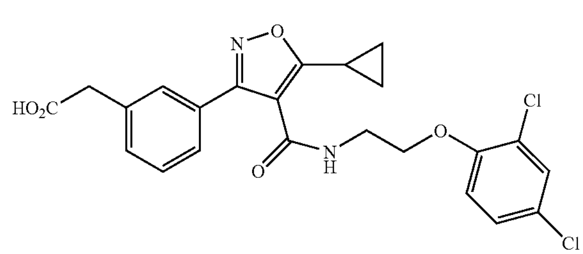 | $^1$H-NMR (400 MHz, d$^6$-DMSO) δ = 8.63 (1H), 7.65-7.19 (m, 6H), 4.17 (2H), 3.60 (2H), 3.60 (2H), 2.32 (1H), 1.07 (4H). MS calculated for $C_{23}H_{21}Cl_2N_2O_5$ (M + H$^+$) 475.1, found 475.0. |

TABLE 2-continued

| Compound Number | Compound Structure | Physical Data $^1$H NMR 400 MHz and/or MS (m/z) |
|---|---|---|
| I4 | 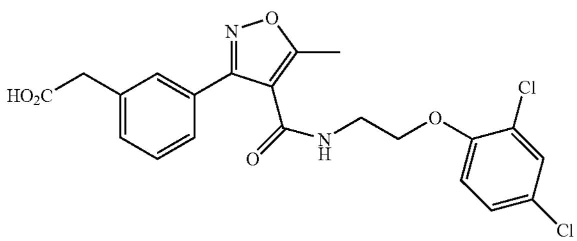 | MS calculated for $C_{21}H_{19}Cl_2N_2O_5$ (M + H$^+$) 449.1, found 449.1. |
| I5 | 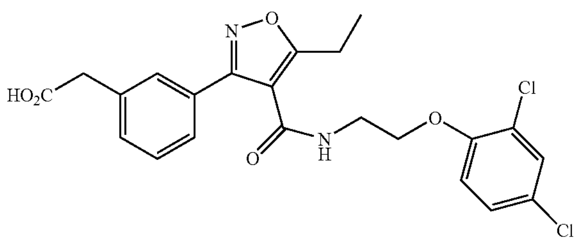 | $^1$H-NMR (400 MHz, CDCl$_3$) δ = 7.53 (s, 1H), 7.49 (m, 1H), 7.33-7.25 (m, 3H), 7.14 (dd, J = 2.5 Hz, J = 8.8 Hz, 1H), 6.73 (d, J = 8.8 Hz, 1H), 5.95 (t, NH), 3.97 (t, J = 5.2 Hz, 2H), 3.70 (q, J = 5.2 Hz, 2H), 3.63 (s, 2H), 3.12 (q, J = 7.6 Hz, 2H), 1.36 (t, J = 7.6 Hz, 3H). MS calculated for $C_{22}H_{21}Cl_2N_2O_5$ (M + H$^+$) 463.1, found 463.1. |
| I6 | 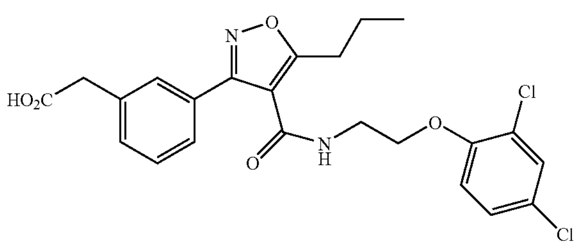 | $^1$H-NMR (400 MHz, CDCl$_3$) δ = 7.53 (s, 1H), 7.49 (m, 1H), 7.33-7.25 (m, 3H), 7.14 (dd, J = 2.5 Hz, J = 8.8 Hz, 1H), 6.73 (d, J = 8.8 Hz, 1H), 5.96 (t, NH), 3.97 (t, J = 5.2 Hz, 2H), 3.70 (q, J = 5.2 Hz, 2H), 3.63 (s, 2H), 3.06 (t, J = 7.6 Hz, 2H), 1.81 (m, 2H), 1.56 (t, J = 7.4 Hz, 3H). MS calculated for $C_{23}H_{23}Cl_2N_2O_5$ (M + H$^+$) 477.1, found 477.1. |
| I7 | 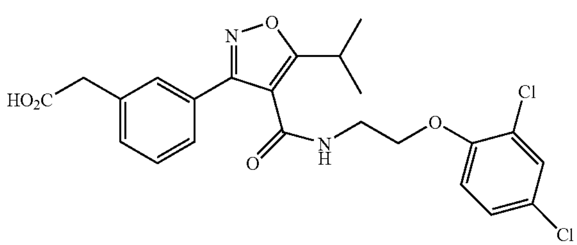 | $^1$H-NMR (400 MHz, CDCl$_3$) δ = 7.51 (s, 1H), 7.47 (m, 1H), 7.30-7.23 (m, 3H), 7.13 (dd, J = 2.5 Hz, J = 8.8 Hz, 1H), 6.71 (d, J = 8.8 Hz, 1H), 5.97 (t, NH), 3.95 (t, J = 5.2 Hz, 2H), 3.76-3.67 (m, 3H), 3.60 (s, 2H), 1.37 (d, J = 7.0 Hz, 6H). MS calculated for $C_{23}H_{23}Cl_2N_2O_5$ (M + H$^+$) 477.1, found 477.1. |
| I8 | 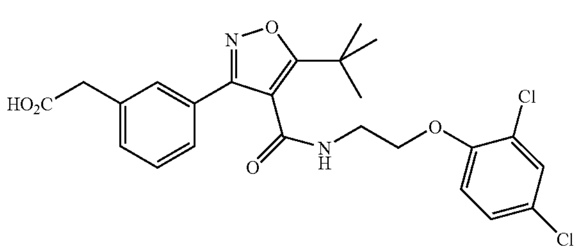 | $^1$H-NMR (400 MHz, CDCl$_3$) δ = 7.54 (s, 1H), 7.50 (m, 1H), 7.36-7.17 (m, 3H), 7.13 (dd, J = 2.5 Hz, J = 8.8 Hz, 1H), 6.69 (d, J = 8.8 Hz, 1H), 6.20 (t, NH), 3.95 (t, J = 4.7 Hz, 2H), 3.70 (q, J = 4.7 Hz, 2H), 3.59 (s, 2H), 1.41 (s, 9H). MS calculated for $C_{24}H_{25}Cl_2N_2O_5$ (M + H$^+$) 491.1, found 491.2. |
| I9 | 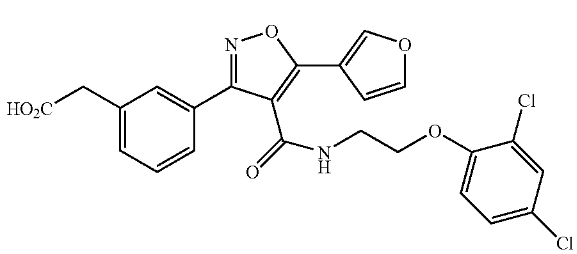 | $^1$H-NMR (400 MHz, CDCl$_3$) δ = 8.44 (s, 1H), 7.58-7.49 (m, 3H), 7.31-7.25 (m, 3H), 7.13 (dd, J = 2.5 Hz, J = 8.8 Hz, 1H), 6.96 (d, J = 1.5 Hz, 1H), 6.71 (d, J = 8.8 Hz, 1H), 5.95 (t, NH), 3.96 (t, J = 5.2 Hz, 2H), 3.73 (q, J = 5.2 Hz, 2H), 3.64 (s, 2H). MS calculated for $C_{24}H_{19}Cl_2N_2O_6$ (M + H$^+$) 501.1, found 501.1. |

TABLE 2-continued

| Compound Number | Compound Structure | Physical Data ¹H NMR 400 MHz and/or MS (m/z) |
|---|---|---|
| I10 | 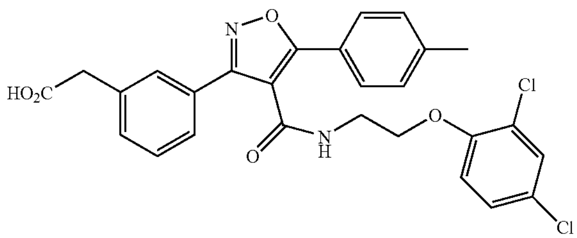 | ¹H-NMR (400 MHz, CDCl₃) δ = 7.71 (s, 1H), 7.69 (s, 1H), 7.67 (s, 1H), 7.63 (d, J = 6.6 Hz, 1H), 7.31-7.24 (m, 4H), 7.13 (m, 3H), 6.68 (d, J = 8.8 Hz, 1H), 6.26 (t, NH), 3.97 (t, J = 5.2 Hz, 2H), 3.74 (q, J = 5.2 Hz, 2H), 3.65 (s, 2H), 2.32 (s, 3H). MS calculated for C$_{27}$H$_{23}$Cl$_2$N$_2$O$_5$ (M + H⁺) 525.1, found 525.2. |
| I11 | 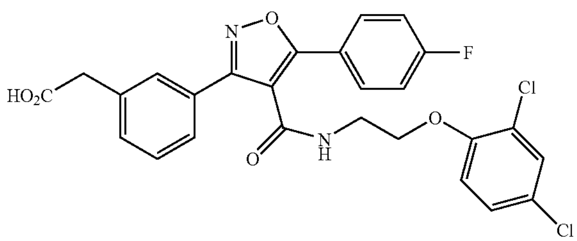 | ¹H-NMR (400 MHz, CDCl₃) δ = 7.92-7.89 (m, 2H), 7.67 (s, 1H), 7.60 (d, J = 6.6 Hz, 1H), 7.29-7.24 (m, 3H), 7.14 (dd, J = 2.5 Hz, J = 8.8 Hz, 1H), 7.08 (m, 2H), 6.70 (d, J = 8.8 Hz, 1H), 6.15 (t, NH), 3.98 (t, J = 5.2 Hz, 2H), 3.76 (q, J = 5.2 Hz, 2H), 3.66 (s, 2H). MS calculated for C$_{26}$H$_{20}$Cl$_2$FN$_2$O$_5$ (M + H⁺) 529.1, found 529.2. |
| I12 | 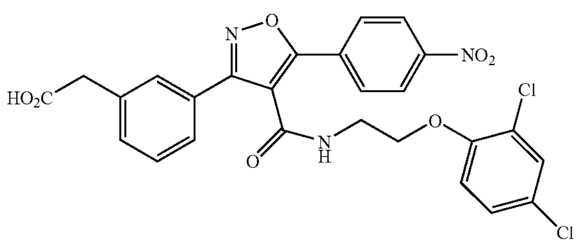 | ¹H-NMR (400 MHz, CDCl₃) δ = 8.24 (d, J = 8.8 Hz, 1H), 8.10 (d, J = 8.8 Hz, 1H), 7.66 (s, 1H), 7.61 (d, J = 6.6 Hz, 1H), 7.30-7.24 (m, 3H), 7.15 (dd, J = 2.5 Hz, J = 8.8 Hz, 1H), 6.70 (d, J = 8.8 Hz, 1H), 6.23 (t, NH), 3.99 (t, J = 4.9 Hz, 2H), 3.76 (q, J = 4.9 Hz, 2H), 3.66 (s, 2H). MS calculated for C$_{26}$H$_{20}$Cl$_2$N$_3$O$_7$ (M + H⁺) 556.1, found 556.1. |
| I13 | 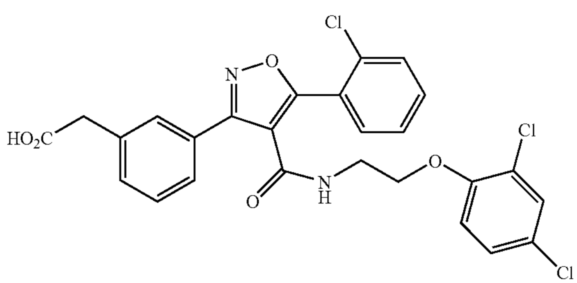 | ¹H-NMR (400 MHz, CDCl₃) δ = 7.66 (s, 1H), 7.63 (d, J = 6.7 Hz, 1H), 7.52 (m, 1H), 7.31-7.21 (m, 6H), 7.09 (dd, J = 2.5 Hz, J = 8.8 Hz, 1H), 6.62 (d, J = 8.8 Hz, 1H), 6.13 (t, NH), 3.84 (t, J = 4.8 Hz, 2H), 3.62 (q, J = 4.8 Hz, 2H), 3.61 (s, 2H). MS calculated for C$_{26}$H$_{20}$Cl$_3$N$_2$O$_5$ (M + H⁺) 545.0, found 545.1. |
| I14 | 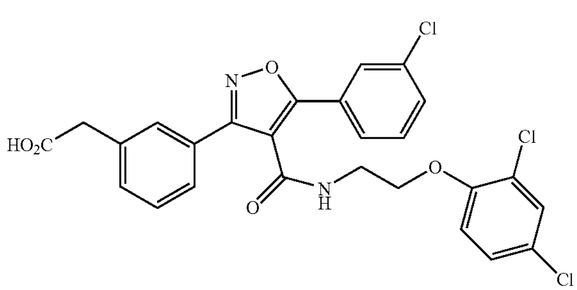 | ¹H-NMR (400 MHz, CDCl₃) δ = 7.87 (s, 1H), 7.76 (d, J = 7.7 Hz, 1H), 7.68 (s, 1H), 7.62 (m, 1H), 7.38-7.23 (m, 5H), 7.14 (dd, J = 2.5 Hz, J = 8.8 Hz, 1H), 6.70 (d, J = 8.8 Hz, 1H), 6.20 (t, NH), 3.99 (t, J = 5.2 Hz, 2H), 3.77 (q, J = 5.2 Hz, 2H), 3.67 (s, 2H). MS calculated for C$_{26}$H$_{20}$Cl$_3$N$_2$O$_5$ (M + H⁺) 545.0, found 545.1. |
| I15 | 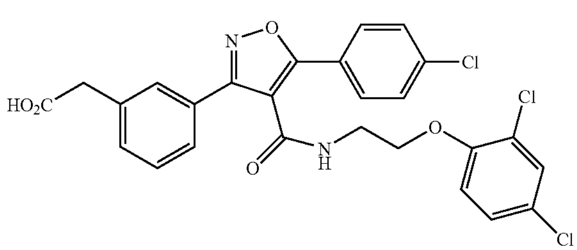 | ¹H-NMR (400 MHz, CDCl₃) δ = 7.79 (d, J = 8.6 Hz, 2H), 7.64 (s, 1H), 7.59 (m, 1H), 7.32 (d, J = 8.6 Hz, 2H), 7.27-7.25 (m, 3H), 7.14 (dd, J = 2.5 Hz, J = 8.8 Hz, 1H), 6.67 (d, J = 8.8 Hz, 1H), 6.27 (t, NH), 3.95 (t, J = 5.2 Hz, 2H), 3.73 (q, J = 5.2 Hz, 2H), 3.64 (s, 2H). MS calculated for C$_{26}$H$_{20}$Cl$_3$N$_2$O$_5$ (M + H⁺) 545.0, found 545.1. |

TABLE 2-continued

| Compound Number | Compound Structure | Physical Data $^1$H NMR 400 MHz and/or MS (m/z) |
|---|---|---|
| I16 | 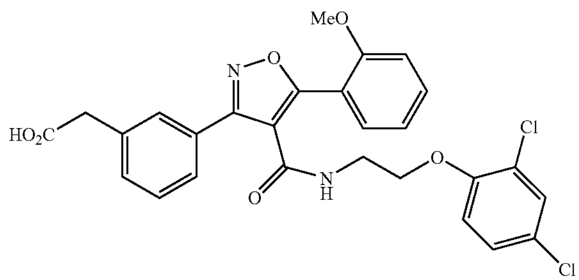 | MS calculated for $C_{27}H_{23}Cl_2N_2O_6$ (M + H$^+$) 541.1, found 541.1. |
| I17 | 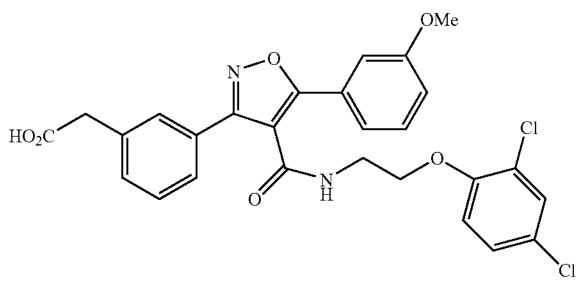 | $^1$H-NMR (400 MHz, CDCl$_3$) δ = 7.69 (s, 1H), 7.64 (m, 1H), 7.41 (m, 2H), 7.30-7.24 (m, 4H), 7.13 (dd, J = 2.5 Hz, J = 8.8 Hz, 1H), 6.93 (m, 1H), 6.69 (d, J = 8.8 Hz, 1H), 6.28 (t, NH), 3.97 (t, J = 5.0 Hz, 2H), 3.81 (s, 3H), 3.76 (q, J = 5.0 Hz, 2H), 3.66 (s, 2H). MS calculated for $C_{27}H_{23}Cl_2N_2O_6$ (M + H$^+$) 541.1, found 541.2. |
| I18 | 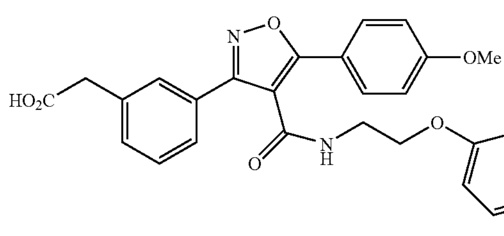 | MS calculated for $C_{27}H_{23}Cl_2N_2O_6$ (M + H$^+$) 541.1, found 541.2. |
| I19 | 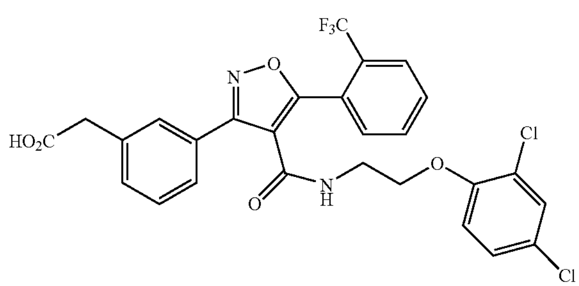 | $^1$H-NMR (400 MHz, CDCl$_3$) δ = 7.75-7.33 (m, 7H), 7.32-7.29 (m, 3H), 7.12 (dd, J = 2.5 Hz, J = 8.8 Hz, 1H), 6.62 (d, J = 8.8 Hz, 1H), 6.05 (t, NH), 3.81 (t, J = 5.1 Hz, 2H), 3.66 (s, 2H), 3.62 (q, J = 5.1 Hz, 2H). MS calculated for $C_{27}H_{20}Cl_2F_3N_2O_6$ (M + H$^+$) 579.1, found 579.1. |
| I20 | 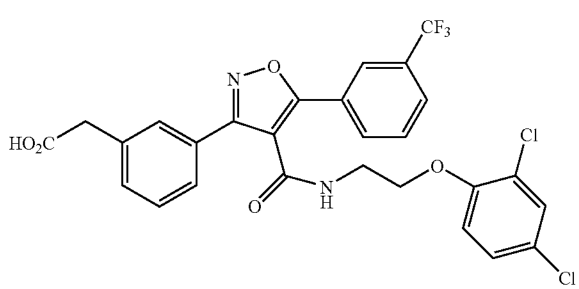 | MS calculated for $C_{27}H_{20}Cl_2F_3N_2O_6$ (M + H$^+$) 579.1, found 579.1. |

TABLE 2-continued

| Compound Number | Compound Structure | Physical Data ¹H NMR 400 MHz and/or MS (m/z) |
|---|---|---|
| I21 | 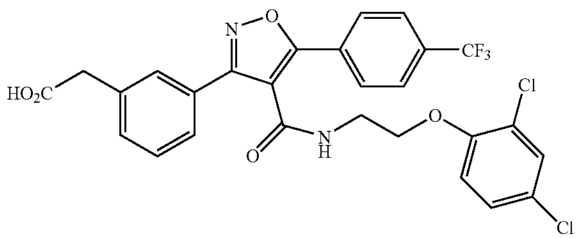 | MS calculated for $C_{27}H_{20}Cl_2F_3N_2O_6$ (M + H⁺) 579.1, found 579.1. |
| I22 | 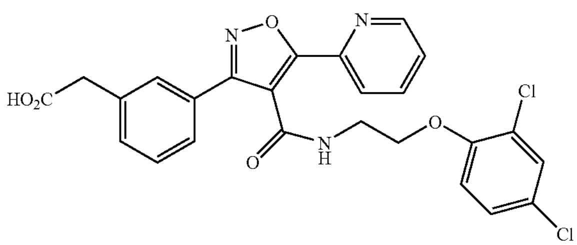 | ¹H-NMR (400 MHz, CDCl₃) δ = 8.60 (d, J = 4.3 Hz, 1H), 8.09 (d, J = 7.9 Hz, 1H), 7.94 (m, 1H), 7.94 (m, 1H), 7.94 (m, 1H), 7.58 (m, NH), 7.41 (m, 3H), 7.30 (d, J = 2.5 Hz, 1H), 7.13 (dd, J = 2.5 Hz, J = 8.8 Hz, 1H), 6.81 (d, J = 8.8 Hz, 1H), 4.15 (t, J = 4.8 Hz, 2H), 3.84 (q, J = 4.8 Hz, 2H), 3.69 (s, 2H). MS calculated for $C_{25}H_{20}Cl_2N_3O_5$ (M + H⁺) 512.1, found 512.1. |
| I23 | 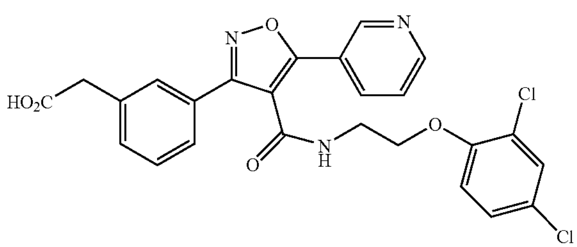 | MS calculated for $C_{25}H_{20}Cl_2N_3O_5$ (M + H⁺) 512.1, found 512.1. |
| I24 | 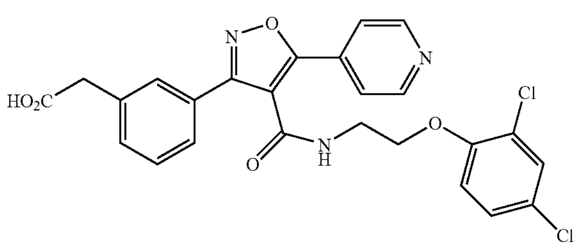 | MS calculated for $C_{25}H_{20}Cl_2N_3O_5$ (M + H⁺) 512.1, found 512.1. |
| I25 | 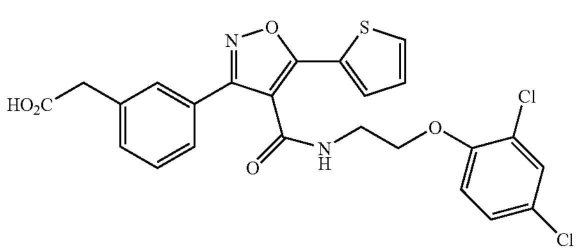 | ¹H-NMR (400 MHz, CDCl₃) δ = 7.91 (m, 1H), 7.61 (s, 1H), 7.57 (m, 1H), 7.52 (m, 1H), 7.31-7.25 (m, 3H), 7.14-7.09 (m, 2H), 6.70 (d, J = 2.5 Hz, 1H), 6.16 (m, NH), 3.99 (t, J = 5.2 Hz, 2H), 3.84 (q, J = 5.2 Hz, 2H), 3.64 (s, 2H). MS calculated for $C_{24}H_{19}Cl_2N_2O_5S$ (M + H⁺) 517.0, found 517.1. |
| I26 | 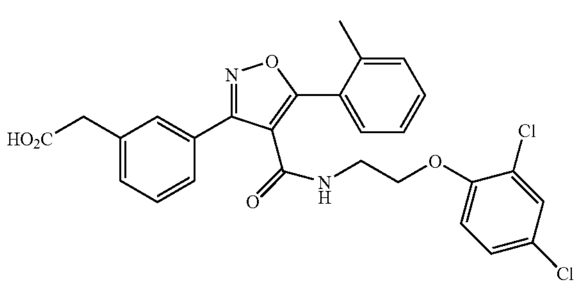 | ¹H-NMR (400 MHz, CDCl₃) δ = 7.71 (s, 1H), 7.68 (d, J = 7.0 Hz, 1H), 7.43-7.11 (m, 8H), 6.63 (d, J = 8.8 Hz, 1H), 6.10 (t, NH), 3.83 (t, J = 5.2 Hz, 2H), 3.66 (m, 4H), 2.35 (s, 3H). MS calculated for $C_{27}H_{23}Cl_2N_2O_5$ (M + H⁺) 525.1, found 525.2. |

TABLE 2-continued

| Compound Number | Compound Structure | Physical Data <br> $^1$H NMR 400 MHz and/or MS (m/z) |
|---|---|---|
| I27 | 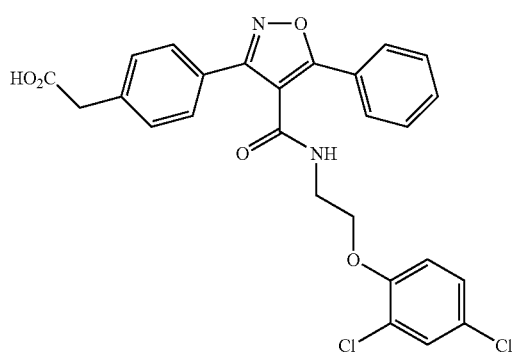 | $^1$H-NMR (400 MHz, CDCl$_3$) δ = 7.67-7.59 (m, 3H), 7.28-7.10 (m, 6H), 6.68 (d, J = 8.8 Hz, 1H), 6.32 (t, NH), 3.96 (t, J = 5.2 Hz, 2H), 3.74 (q, J = 5.2 Hz, 2H), 3.64 (s, 3H), 2.35 (s, 3H). MS calculated for C$_{27}$H$_{23}$Cl$_2$N$_2$O$_5$ (M + H$^+$) 525.1, found 525.2. |

Example I29

(4-{4-[2-(2,4-Dichloro-phenoxy)-ethyl-carbamoyl]-5-phenyl-isoxazol-3-yl}-phenyl)-acetic acid Following the procedure of Example I1 above, using 4-bromophenyl acetic acid instead of intermediate 45, the title compound I29 is prepared as a white solid: $^1$H-NMR (400 MHz, CD$_3$CN) δ=8.00 (m, 1H), 7.86 (d, J=8.4 Hz, 2H), 7.62 (m, 5H), 7.55 (m, 2H), 7.44 (m, 2H), 7.12 (d, J=8.8 Hz, 1H), 4.26 (t, J=4.8 Hz, 2H), 3.87 (q, J=5.2 Hz, 2H), 3.76 (s, 2H). MS calculated for C$_{26}$H$_{21}$Cl$_2$N$_2$O$_5$ (M+H$^+$) 511.0, found 511.1.

Example I30

(4-{4-[2-(2,4-Dichloro-phenoxy)-ethyl-carbamoyl]-5-phenyl-isoxazol-3-yl}-2-methyl-phenoxy)-acetic acid

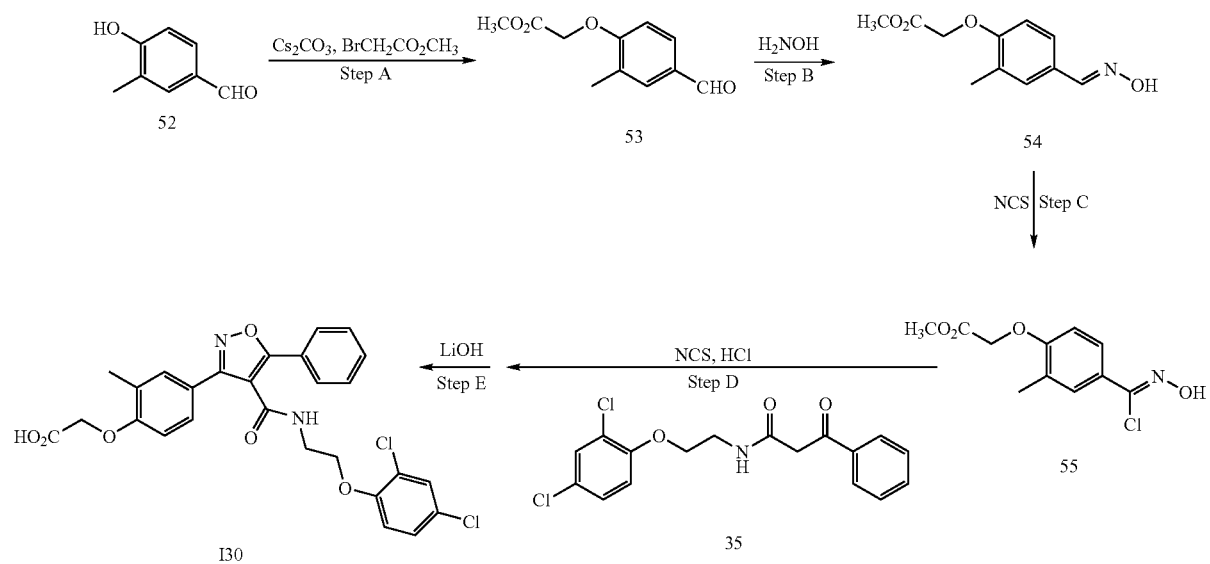

Step A: 4-Hydroxy-3-methyl-benzaldehyde 52 (0.50 g, 3.67 mmol) is dissolved in 10 mL acetonitrile. Cesium carbonate (2.07 g, 6.35 mmol) and methyl bromoacetate (0.40 mL, 4.35 mmol) are added and the suspension is vigorously stirred at room temperature overnight. The suspension is poured into 1N aqueous HCl and extracted with EtOAc. Drying over MgSO4, filtration and concentration yielded (4-formyl-2-methyl-phenoxy)-acetic acid methyl ester 53: $^1$H-NMR (400 MHz, CDCl$_3$) δ=9.86 (s, 1H), 7.71 (d, J=1.6 Hz, 1H), 7.68 (dd, J=8.4, 1.6 Hz, 1H), 6.77 (d, J=8.4 Hz, 1H), 4.75 (s, 2H), 3.81 (s, 3H), 2.34 (s, 3H). MS calculated for $C_{11}H_{13}O_4$ (M+H$^+$) 209.0, found 209.0.

Step B: (4-Formyl-2-methyl-phenoxy)-acetic acid methyl ester 53 (0.8 g, 3.6 mmol) is dissolved in dimethoxy-ethane (5 mL). Hydroxy-amine hydrochloride (0.47 g, 6.8 mmol) is added, followed by ethyl-diisopropylamine (1.4 mL, 8.5 mmol). The mixture is stirred at room temperature for 6 hours. The solvent is removed in vacuo and the residue is extracted three times with ethyl acetate. The organic layers are combined, dried over MgSO$_4$, filtered, and concentrated to afford the oxime 54 as a white solid: $^1$H-NMR (400 MHz, CDCl$_3$) δ=8.06 (s, 1H), 7.42 (d, J=1.6 Hz, 1H), 7.32 (dd, J=8.4, 1.6 Hz, 1H), 6.68 (d, J=8.4 Hz, 1H), 4.69 (s, 2H), 3.81 (s, 3H), 2.30 (s, 3H). MS calculated for $C_{11}H_{14}NO_4$ (M+H$^+$) 224.1, found 224.1.

Step C: [4-(Hydroxyimino-methyl)-2-methyl-phenoxy]-acetic acid methyl ester 54 (0.05 g, 0.22 mmol) and N-chlorosuccinimide (0.025 g, 0.19 mmol) are dissolved in DME (2 mL). After adding catalytic amounts of HCl (4M solution in dioxane) to the solution, an exothermic reaction occurred. After stirring for 2 hours at room temperature, the mixture is diluted with H$_2$O and extracted three times with ethyl acetate to afford intermediate 55; the crude material is dissolved in 1 mL DME and used as such; MS calculated for $C_{11}H_{12}ClNO_4$ (M+H$^+$) 258.1, found 258.0.

Step D: A solution of N-[2-(2,4-Dichloro-phenoxy)-ethyl]-3-oxo-3-phenyl-propionamide 35 (0.04 g, 0.12 mmol) in DME (1 mL) is cooled to −20° C. Potassium t-butoxide (0.2 mL of a 1.0 M solution in THF) is added and the solution is stirred for 10 min at −20° C. Intermediate 55 prepared in Step C is added as a solution in 1 mL DME. The mixture is stirred for 30 min at −20° C., and then it is warmed to room temperature. After stirring at room temperature for 1 hour the mixture is poured into water and extracted three times with EtOAc. The organic layers are combined, dried (MgSO$_4$), filtered, and concentrated to afford crude (4-{4-[2-(2,4-dichloro-phenoxy)-ethyl-carbamoyl]-5-phenyl-isoxazol-3-yl}-2-methyl-phenoxy)-acetic acid methyl ester. MS calculated for $C_{28}H_{25}Cl_2N_2O_6$ (M+H$^+$) 555.0, found 555.0.

Step E: The crude (4-{4-[2-(2,4-dichloro-phenoxy)-ethyl-carbamoyl]-5-phenyl-isoxazol-3-yl}-2-methyl-phenoxy)-acetic acid methyl ester is dissolved in DME (1 mL). A solution of 1 M LiOH in H$_2$O (0.2 mL) and is added and the mixture is stirred overnight at room temperature. The mixture is concentrated, then acidified with 1 M HCl, extracted with EtOAc (10 mL), dried over MgSO$_4$, filtered, concentrated and purified on reverse phase HPLC (H$_2$O/MeCN gradient) to afford the title compound I30 as a white solid: $^1$H-NMR (400 MHz, CD$_3$CN) δ=7.56 (d, J=1.6, 1H), 7.49 (dd, J=8.4, 2.4 Hz, 1H), 7.45 (m, 5H), 7.39 (d, J=2.4 Hz, 1H), 7.27 (dd, J=8.8, 2.8 Hz, 1H), 7.20 (t, J=5.6 Hz, NH), 6.96 (d, J=8.8 Hz, 1H), 6.73 (d, J=8.8 Hz, 1H), 4.64 (s, 2H), 4.08 (t, J=5.2 Hz, 2H), 3.70 (q, J=5.3 Hz, 2H), 2.23 (s, 3H). MS calculated for $C_{27}H_{23}Cl_2N_2O_6$ (M+H$^+$) 541.0, found 541.0.

Example I31

(4-{4-[2-(2,4-Dichloro-phenoxy)-ethyl-carbamoyl]-5-phenyl-isoxazol-3-yl}-phenoxy)-acetic acid

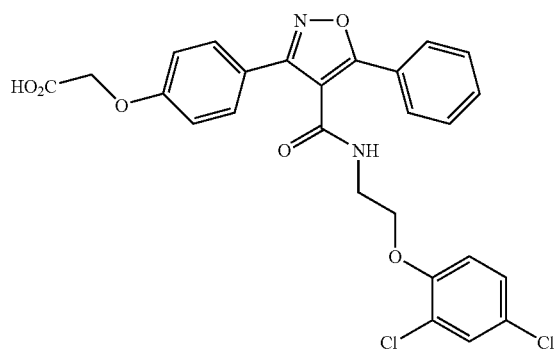

Following an analogous procedure to the one for Example I29 above, the title compound I31 is prepared as a white solid: $^1$H-NMR (400 MHz, CDCl$_3$) δ=7.86 (m, 2H), 7.70 (d, J=8.8 Hz, 2H), 7.40 (m, 3H), 7.28 (d, J=2.4 Hz, 1H), 7.17 (dd, J=8.8, 2.4 Hz, 1H), 6.87 (d, J=8.8 Hz, 2H), 6.72 (d, J=8.8 Hz, 2H), 6.21 (t, J=5.6 Hz, NH), 4.60 (s, 2H), 4.01 (t, J=5.2 Hz, 2H), 3.81 (td, J=5.6, 5.2 Hz, 2H). MS calculated for $C_{26}H_{21}Cl_2N_2O_6$ (M+H$^+$) 527.0, found 526.9.

Example I32

(5-{4-[2-(2,4-Dichloro-phenoxy)-ethylcarbamoyl]-5-phenyl-isoxazol-3-yl}-2-methoxy-phenyl)-acetic acid

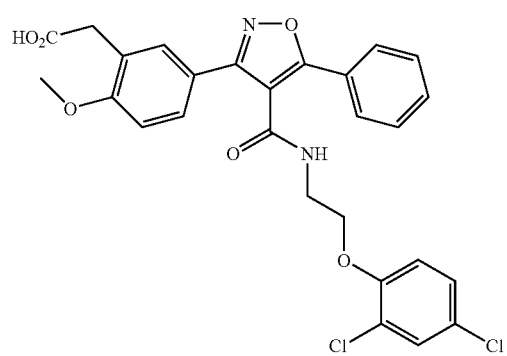

Following the procedure of Example I30 above, using the appropriate bromide in Step A, the title compound I32 is prepared as a white solid: MS calculated for $C_{27}H_{23}Cl_2N_2O_6$ (M+H$^+$) 541.0, found 541.0.

Example I33

3-(3-{4-[2-(2,4-Dichloro-phenoxy)-ethyl-carbamoyl]-5-phenyl-isoxazol-3-yl}-phenyl)-propionic acid

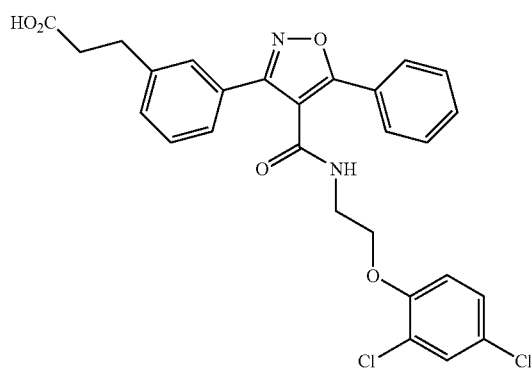

Following the procedure of Example I1 above, using the appropriate bromide in Step A, the title compound I33 is prepared as a white solid: MS calculated for $C_{27}H_{23}Cl_2N_2O_5$ (M+H$^+$) 525.0, found 525.0.

Example I34

3-(4-{4-[2-(2,4-Dichloro-phenoxy)-ethyl-carbamoyl]-5-phenyl-isoxazol-3-yl}-phenyl)-propionic acid

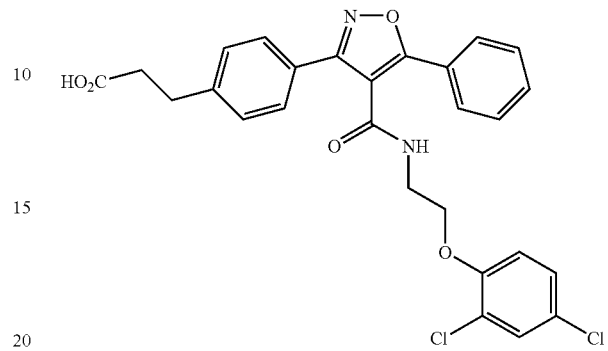

Following the procedure of Example I1 above, using the appropriate bromide in Step A, the title compound I34 is prepared as a white solid: MS calculated for $C_{27}H_{23}Cl_2N_2O_5$ (M+H$^+$) 525.0, found 525.0.

Example J1

(3-Chloro-4-{4-[2-(2,4-dichloro-phenoxy)-ethylcarbamoyl]-3-phenyl-isoxazol-5-yl}-phenyl)-acetic acid

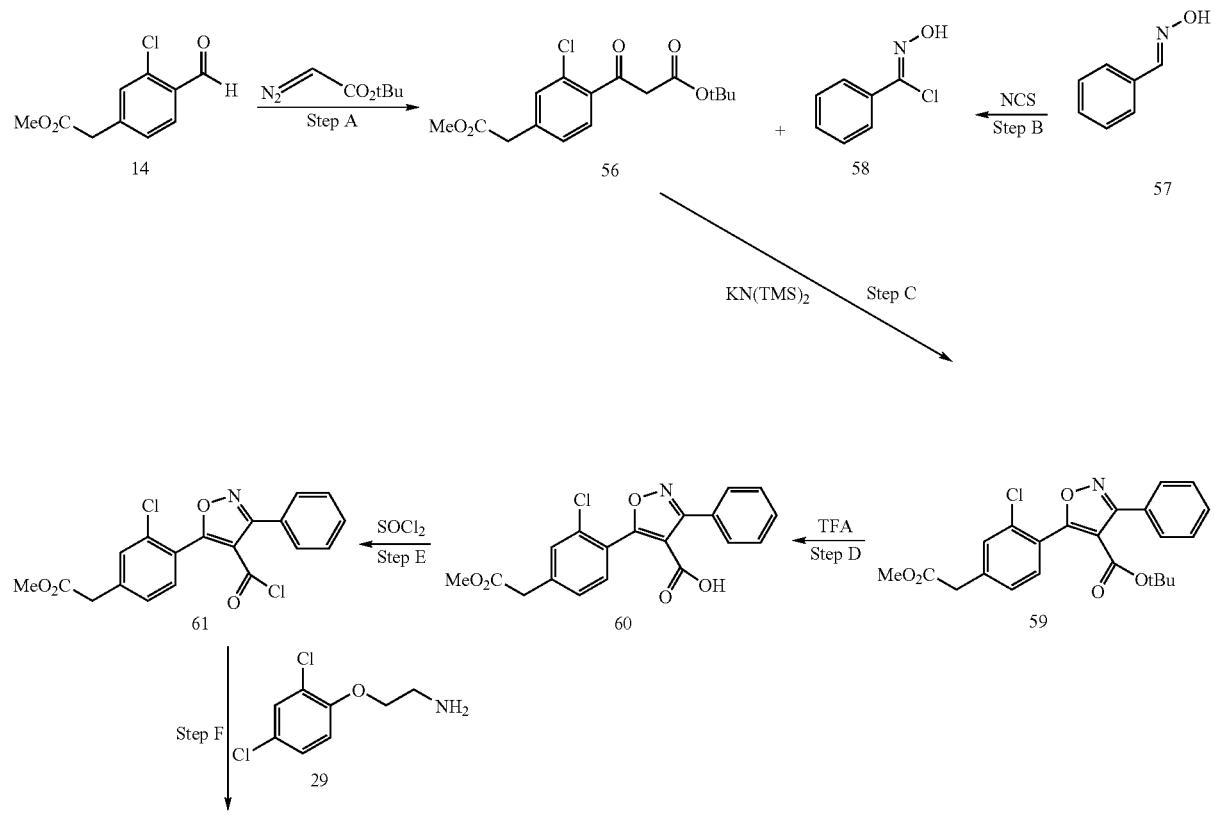

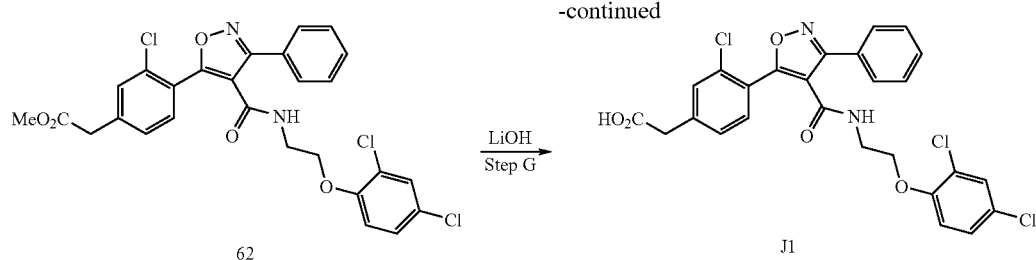

Step A: A flame-dried flask is charged with tert-butyldiazoacetate (0.62 mL, 4.48 mmol) and anhydrous tin(II) chloride (168 mg, 0.88 mmol) in dry DCM (10 mL). (3-Chloro-4-formyl-phenyl)-acetic acid methyl ester 14 (500 mg, 2.35 mmol) is dissolved in DCM (5 mL) and added dropwise to the reaction mixture. After stirring for 6 h at room temperature the reaction mixture is poured into brine (50 mL) and extracted with ether (3×50 mL). The combined organic layers are dried (MgSO$_4$), filtered, concentrated and purified on reverse phase HPLC (H$_2$O/MeCN gradient) to afford 3-(2-Chloro-4-methoxycarbonylmethyl-phenyl)-3-oxo-propionic acid tert-butyl ester 56 as a white solid: MS calculated for C$_{16}$H$_{19}$Cl$_2$NaO$_5$ (M+Na$^+$) 349.1, found 349.1.

Step B: Benzaldoxime 57 (0.50 g, 4.1 mmol) and N-chlorosuccinimide (0.55 g, 4.1 mmol) are dissolved in MeCN (10 mL). After stirring for 3 hours at room temperature the solvent is removed in vacuo to afford benzyl chloroxime 58 (0.64 g, 4.1 mmol, quant.) as a wax-like solid, which is used immediately without further purification: MS calculated for C$_7$H$_7$ClNO (M+H$^+$) 156.0, found 156.0.

Step C: Intermediate 56 (115 mg, 0.35 mmol) is dissolved in MeCN (3 mL). Potassium bis(trimethylsilyl)amide (106 mg, 0.53 mmol) is added slowly while stirring at room temperature. Then the mixture is cooled to 0° C., and a solution of intermediate 58 (55 mg, 0.35 mmol) in CH$_3$CN (1 mL) is added. The mixture is stirred at room temperature overnight, then H$_2$O (5 mL) is added and the mixture is extracted with DCM (3×10 mL). After concentration the crude product is purified on reverse phase HPLC (H$_2$O/MeCN gradient) to afford 5-(2-chloro-4-methoxycarbonylmethyl-phenyl)-3-phenyl-isoxazole-4-carboxylic acid tert-butyl ester 59 as a white solid: $^1$H-NMR (400 MHz, CDCl$_3$) δ=7.73 (m, 2H), 7.47 (m, 5H), 7.33 (m, 1H), 3.72 (s, 3H), 3.68 (s, 2H), 1.23 (s, 9H). MS calculated for C$_{23}$H$_{23}$ClNO$_5$ (M+H$^+$) 428.1, found 428.1.

Step D: 5-(2-Chloro-4-methoxycarbonylmethyl-phenyl)-3-phenyl-isoxazole-4-carboxylic acid tert-butyl ester 59 (25 mg, 0.06 mmol) is dissolved in trifluoroacetic acid (1 mL) and stirred at room temperature for 2 hours. Then the solvent is evaporated and the remainder is dried on high vacuum to afford 5-(2-Chloro-4-methoxycarbonylmethyl-phenyl)-3-phenyl-isoxazole-4-carboxylic acid 60 as a white solid: $^1$H-NMR (400 MHz, CDCl$_3$) δ=7.62 (m, 2H), 7.38 (m, 5H), 7.24 (m, 1H), 3.64 (s, 3H), 3.59 (s, 2H). MS calculated for C$_{19}$H$_{15}$ClNO$_5$ (M+H$^+$) 372.1, found 372.1.

Step E: 5-(2-Chloro-4-methoxycarbonylmethyl-phenyl)-3-phenyl-isoxazole-4-carboxylic acid 60 (22 mg, 0.06 mmol) and thionyl chloride (5 μL, 0.07 mmol) are dissolved in toluene (0.8 mL). The mixture is stirred at 120° C. for 3 hours. Then the reaction mixture is cooled down to 0° C. and triethylamine (35 μL, 0.25 mmol) are added dropwise. The resulting solution containing crude [3-chloro-4-(4-chlorocarbonyl-3-phenyl-isoxazol-5-yl)-phenyl]-acetic acid methyl ester 61 is used without further purification: MS calculated for C$_{19}$H$_{14}$Cl$_2$NO$_4$ (M+H$^+$) 390.0, found 390.1.

Step F: A solution of 2-(2,4-Dichloro-phenoxy)-ethylamine 29 (19 mg, 0.09 mmol) in toluene (0.2 mL) is cooled to 0° C. The above solution of intermediate 61 (0.06 mmol) is added and the solution is warmed to room temperature. After stirring at room temperature for 1 hour the mixture is poured into H$_2$O and extracted three times with DCM. The organic layers are combined, dried (MgSO$_4$), filtered, and concentrated to afford crude (3-Chloro-4-{4-[2-(2,4-dichloro-phenoxy)-ethyl-carbamoyl]-3-phenyl-isoxazol-5-yl}-phenyl)-acetic acid methyl ester 62.

Step G: The crude (3-Chloro-4-{4-[2-(2,4-dichloro-phenoxy)-ethyl-carbamoyl]-3-phenyl-isoxazol-5-yl}-phenyl)-acetic acid methyl ester 62 is dissolved in THF (2 mL). A solution of 1 M LiOH in H$_2$O (0.6 mL) is added and the mixture is stirred overnight at room temperature. The mixture is acidified with 1 M HCl, DCM (10 mL) is added and the organic layer washed with H$_2$O (3×5 mL). The organic layer is dried (MgSO$_4$), filtered, concentrated and purified on reverse phase HPLC (H$_2$O/MeCN gradient) to afford the title compound J1 as a white solid: $^1$H-NMR (400 MHz, CDCl$_3$) δ=7.66 (m, 2H), 7.51 (d, J=7.9 Hz, 1H), 7.34-7.19 (m, 6H), 7.09 (dd, J=8.8 Hz, J=2.5 Hz, 1H), 6.62 (d, J=8.8 Hz, 1H), 6.04 (t, J=5.6 Hz, NH), 3.86 (t, J=4.9 Hz, 2H), 3.63 (q, J=5.2 Hz, 2H), 3.51 (s, 2H). MS calculated for C$_{26}$H$_{20}$Cl$_3$N$_2$O$_5$ (M+H$^+$) 545.0, found 545.0.

Transcriptional Assay

Transfection assays are used to assess the ability of compounds of the invention to modulate the transcriptional activity of the PPARs. Briefly, expression vectors for chimeric proteins containing the DNA binding domain of yeast GAL4 fused to the ligand-binding domain (LBD) of either PPARδ, PPARα or PPARγ are introduced via transient transfection into mammalian cells, together with a reporter plasmid where the luciferase gene is under the control of a GAL4 binding site. Upon exposure to a PPAR modulator, PPAR transcriptional activity varies, and this can be monitored by changes in luciferase levels. If transfected cells are exposed to a PPAR agonist, PPAR-dependent transcriptional activity increases and luciferase levels rise.

293T human embryonic kidney cells (8×10$^6$) are seeded in a 175 cm$^2$ flask a day prior to the start of the experiment in 10% FBS, 1% Penicillin/Streptomycin/Fungizome, DMEM Media. The cells are harvested by washing with PBS (30 ml) and then dissociating using trypsin (0.05%; 3 ml). The trypsin is inactivated by the addition of assay media (DMEM, CA-dextran fetal bovine serum (5%). The cells are spun down and resuspended to 170,000 cells/ml. A Transfection mixture of GAL4-PPAR LBD expression plasmid (1 μg), UAS-luciferase reporter plasmid (1 μg), Fugene (3:1 ratio; 6 μL) and serum-free media (200 μL) was prepared and incubated for 15-40 minutes at room temperature. Transfection mixtures are added to the cells to give 0.16M cells/mL, and cells (50 μl/well) are then plated into 384 white, solid-bottom, TC-treated plates. The cells are further incubated at 37° C., 5.0% $CO_2$ for 5-7 hours. A 12-point series of dilutions (3 fold serial dilutions) are prepared for each test compound in DMSO with a starting compound concentration of 10 μM. Test compound (500 nl) is added to each well of cells in the assay plate and the cells are incubated at 37° C., 5.0% $CO_2$ for 18-24 hours. The cell lysis/luciferase assay buffer, Bright-Glo™ (25%; 25 μl; Promega), is added to each well. After a further incubation for 5 minutes at room temperature, the luciferase activity is measured.

Raw luminescence values are normalized by dividing them by the value of the DMSO control present on each plate. Normalized data is analyzed and dose-response curves are fitted using Prizm graph fitting program. EC50 is defined as the concentration at which the compound elicits a response that is half way between the maximum and minimum values. Relative efficacy (or percent efficacy) is calculated by comparison of the response elicited by the compound with the maximum value obtained for a reference PPAR modulator.

Compounds of Formula I, in free form or in pharmaceutically acceptable salt form, exhibit valuable pharmacological properties, for example, as indicated by the in vitro tests described in this application. Compounds of the invention preferably have an EC50 for PPARδ of less than 1 μM, more preferably less than 500 nm, more preferably less than 100 nM. Compounds of the invention are at least 100-fold selective for PPARδ over PPARγ.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

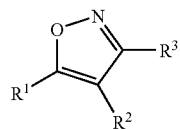

I in which $R^1$ is selected from $C_{1-6}$alkyl, $C_{3-12}$cycloalkyl, $C_{3-8}$heterocycloalkyl, $C_{6-10}$aryl and $C_{5-10}$heteroaryl; wherein any alkyl, aryl, heteroaryl, cycloalkyl and heterocycloalkyl of $R^1$ is optionally substituted with 1 to 3 radicals independently selected from halo, nitro, cyano, $C_{1-6}$alkyl, $C_{1-6}$alkoxy, halo-substituted-$C_{1-6}$alkyl, halo-substituted-$C_{1-6}$alkoxy, —XC(O)Y$R^5$ and —XYC(O)$R^5$; wherein X is a bond or $C_{1-4}$-alkylene and Y is selected from a bond, O, S, and N$R^6$; and $R^5$ is selected from $C_{1-6}$alkyl, $C_{3-12}$cycloalkyl, $C_{3-8}$heterocycloalkyl, $C_{6-10}$aryl and $C_{5-10}$heteroaryl; and $R^6$ is selected from hydrogen, $C_{1-6}$alkyl, $C_{3-12}$cycloalkyl, $C_{3-8}$heterocycloalkyl, $C_{6-10}$aryl and $C_{5-10}$heteroaryl;

$R^2$ is —C(O)N$R^4$XO$R^5$; wherein X is a bond or $C_{1-4}$alkylene; $R^4$ is selected from hydrogen and $C_{1-6}$alkyl; $R^5$ is selected from $C_{3-12}$cycloalkyl, $C_{3-8}$heterocycloalkyl, $C_{6-10}$aryl and $C_{5-10}$heteroaryl;

wherein any alkylene group of $R^2$ is optionally substituted by halo, $C_{1-6}$alkyl and phenyl; wherein any aryl, heteroaryl, cycloalkyl and heterocycloalkyl of $R^2$ is substituted with 2 to 3 radicals independently selected from halo, nitro, cyano, methyl, $C_{1-6}$alkoxy, halo-substituted-$C_{1-6}$alkyl and halo-substituted-$C_{1-6}$alkoxy;

$R^3$ is selected from $C_{3-12}$cycloalkyl, $C_{3-8}$heterocycloalkyl, $C_{6-10}$aryl and $C_{5-10}$heteroaryl; wherein any aryl, heteroaryl, cycloalkyl and heterocycloalkyl of $R^3$ is optionally substituted with 1 to 3 radicals independently selected from halo, nitro, cyano, $C_{1-6}$alkyl, $C_{1-6}$alkoxy, halo-substituted-$C_{1-6}$alkyl, halo-substituted-$C_{1-6}$alkoxy, —XOXC(O)O$R^5$, —XC(O)O$R^5$ wherein X is independently selected from a bond and $C_{1-4}$alkylene; and $R^5$ is selected from hydrogen and $C_{1-4}$alkyl; or a pharmaceutically acceptable salts thereof.

2. The compound of claim 1 in which:

$R^1$ is selected from $C_{1-6}$alkyl, $C_{3-12}$cycloalkyl, $C_{5-10}$heteroaryl and $C_{6-10}$aryl; wherein any aryl or heteroaryl of $R_1$ is optionally substituted by 1 to 3 radicals independently selected from halo, nitro, $C_{1-6}$alkyl, $C_{1-6}$alkoxy, halo-substituted-$C_{1-6}$alkyl and —XC(O)O$R^5$; wherein X is a bond or $C_{1-4}$alkylene; and $R^5$ is selected from hydrogen and $C_{1-6}$alkyl;

$R^2$ is —C(O)N$R^4$XO$R^5$; wherein X is a bond or $C_{1-4}$alkylene; $R^4$ is selected from hydrogen and $C_{1-6}$alkyl; $R^5$ is $C_{3-12}$cycloalkyl, $C_{3-8}$heterocycloalkyl, $C_{6-10}$aryl and $C_{5-10}$heteroaryl;

wherein any alkylene group of $R^2$ is optionally substituted by $C_{1-6}$alkyl and phenyl; wherein any aryl, heteroaryl, cycloalkyl and heterocycloalkyl of $R^2$ is substituted with 2 to 3 radicals independently selected from halo, nitro, $C_{1-6}$alkoxy, halo-substituted-$C_{1-6}$alkyl and halo-substituted-$C_{1-6}$alkoxy; and $R^3$ is $C_{6-10}$aryl optionally substituted with 1 to 3 radicals independently selected from halo, $C_{1-6}$alkyl, $C_{1-6}$alkoxy, —OXC(O)O$R^5$ and —XC(O)O$R^5$ wherein X is a bond or $C_{1-4}$alkylene; and $R^5$ is selected from hydrogen and $C_{1-6}$alkyl.

3. The compound of claim 1 in which:

$R^1$ is selected from methyl, ethyl, t-butyl, propyl, cyclopropyl, isopropyl, pyridinyl, furanyl, thienyl and phenyl optionally substituted with 1 to 2 radicals independently selected from halo, methyl, nitro, methoxy, carboxymethyl and trifluoromethyl;

$R^2$ is selected from —C(O)NH(CH$_2$)$_2$O$R^5$ and —C(O)N(CH$_3$)(CH$_2$)$_2$O$R^5$; wherein $R^5$ is selected from phenyl, cyclopentyl, furanyl, pyridinyl and naphthyl; wherein any alkylene group of $R^2$ is optionally substituted by a radical selected from methyl and phenyl; wherein any aryl, heteroaryl, cycloalkyl and heterocycloalkyl of $R^2$ is substituted with 2 to 3 radicals independently selected from halo, nitro, methyl, trifluoromethyl, trifluoromethoxy and methoxy; and $R^3$ is phenyl optionally substituted with 1 to 3 radicals independently selected from halo, methyl, methoxy, —OCH$_2$C(O)OH, —(CH$_2$)$_2$C(O)OH and —CH$_2$C(O)OH.

4. A compound of Formula Ia:

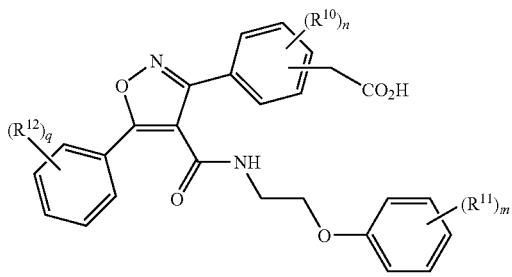

in which: q, m and n are independently selected from 0, 1 and 2; and $R^{10}$, $R^{11}$ and $R^{12}$ are each independently is selected from halo, $C_{1-6}$alkyl, nitro, $C_{1-6}$alkoxy and halo-substituted-$C_{1-6}$alkyl.

5. A compound selected from: (5-{4-[2-(2,4-Dichloro-phenoxy)-ethyl-carbamoyl]-5-phenyl-isoxazol-3-yl}-phenyl)-acetic acid; (3-Chloro-4-{4-[2-(2,4-dichloro-phenoxy)-ethylcarbamoyl]-5-phenyl-isoxazol-3-yl}-phenyl)-acetic acid; (3-Chloro-4-{4-[2-(2,4-dichloro-phenoxy)-ethylcarbamoyl]-5-p-tolyl-isoxazol-3-yl}-phenyl)-acetic acid; {3-Chloro-4-[4-[2-(2,4-dichloro-phenoxy)-ethylcarbamoyl]-5-(4-fluoro-phenyl)-isoxazol-3-yl]-phenyl}-acetic acid; {3-Chloro-4-[4-[2-(2,4-dichloro-phenoxy)-ethylcathamoyl]-5-(4-nitro-phenyl)-isoxazol-3-yl]-phenyl}-acetic acid; (3-Chloro-4-{5-(2-chloro-phenyl)-4-[2-(2,4-dichloro-phenoxy)-ethylcarbamoyl]-isoxazol-3-yl}-phenyl)-acetic acid; (3-Chloro-4-{5-(4-chloro-phenyl)-4-[2-(2,4-dichloro-phenoxy)-ethylcarbamoyl]-isoxazol-3-yl}-phenyl)-acetic acid; {3-Chloro-4-[4-[2-(2,4-dichloro-phenoxy)-ethylcarbamoyl]-5-(2-methoxy-phenyl)-isoxazol-3-yl]-phenyl}-acetic acid; {3-Chloro-4-[4-[2-(2,4-dichloro-phenoxy)-ethylcarbamoyl]-5-(3-methoxy-phenyl)-isoxazol-3-yl]-phenyl}-acetic acid; {3-Chloro-4-[4-[2-(2,4-dichloro-phenoxy)-ethylcarbamoyl]-5-(4-methoxy-phenyl)-isoxazol-3-yl]-phenyl}-acetic acid; {3-Chloro-4-[4-[2-(2,4-dichloro-phenoxy)-ethylcarbamoyl]-5-(2-trifluoromethyl-phenyl)-isoxazol-3-yl]-phenyl}-acetic acid; {3-Chloro-4-[4-[2-(2,4-dichloro-phenoxy)-ethylcarbamoyl]-5-(3-trifluoromethyl-phenyl)-isoxazol-3]-phenyl}-acetic acid; {3-Chloro-4-[4-[2-(2,4-dichloro-phenoxy)-ethylcarbamoyl]-5-(4-trifluoromethyl-phenyl)-isoxazol-3-yl]-phenyl}-acetic acid; (3-{4-[2-(2,4-Dichloro-phenoxy)-ethylcarbamoyl]-5-p-tolyl-isoxazol-3-yl}-phenyl)-acetic acid; {3-[4-[2-(2,4-Dichloro-phenoxy)-ethylcarbamoyl]-5-(4-fluoro-phenyl)-isoxazol-3-yl]-phenyl}-acetic acid; {3-[4-[2-(2,4-Dichloro-phenoxy)-ethylcarbamoyl]-5-(4-nitro-phenyl)-isoxazol-3-yl]-phenyl}-acetic acid; (3-{5-(2-Chloro-phenyl)-4-[2-(2,4-dichloro-phenoxy)-ethylcarbamoyl]-isoxazol-3-yl}-phenyl)-acetic acid; (3-{5-(3-Chloro-phenyl)-4-[2-(2,4-dichloro-phenoxy)-ethylcarbamoyl]-isoxazol-3-yl}-phenyl)-acetic acid; (3-{5-(4-Chloro-phenyl)-4-[2-(2,4-dichloro-phenoxy)-ethylcarbamoyl]-isoxazol-3-yl}-phenyl)-acetic acid; {3-[4-[2-(2,4-Dichloro-phenoxy)-ethylcarbamoyl]-5-(2-methoxy-phenyl)-isoxazol-3-yl]-phenyl}-acetic acid; {3-[4-[2-(2,4-Dichloro-phenoxy)-ethylcarbamoyl]-5-(3-methoxy-phenyl)-isoxazol-3-yl]-phenyl}-acetic acid; {3-[4-[2-(2,4-Dichloro-phenoxy)-ethylcarbamoyl]-5-(4-methoxy-phenyl)-isoxazol-3-yl]-phenyl}-acetic acid; {3-[4-[2-(2,4-Dichloro-phenoxy)-ethylcarbamoyl]-5-(2-trifluoromethyl-phenyl)-isoxazol-3-yl]-phenyl}-acetic acid; {3-[4-[2-(2,4-Dichloro-phenoxy)-ethylcarbamoyl]-5-(3-trifluoromethyl-phenyl)-isoxazol-3-yl]-phenyl}-acetic acid; {3-[4-[2-(2,4-Dichloro-phenoxy)-ethylcarbamoyl]-5-(4-trifluoromethyl-phenyl)-isoxazol-3-yl]-phenyl}-acetic acid; (3-{4-[2-(2,4-Dichloro-phenoxy)-ethylcarbamoyl]-5-o-tolyl-isoxazol-3-yl}-phenyl)-acetic acid; and (3-{4-[2-(2,4-Dichloro-phenoxy)-ethylcarbamoyl]-5-m-tolyl-isoxazol-3-yl}-phenyl)-acetic acid.

6. A compound selected from: 3-(2,6-Dichloro-phenyl)-5-methyl-isoxazole-4-carboxylic acid [2-(2-nitro-4-trifluoromethyl-phenoxy)-ethyl]-amide; Dichloro-phenyl)-5-methyl-isoxazole-4-carboxylic acid methyl-[2-(2-nitro-4-trifluoromethyl-phenoxy)-ethyl]-amide; (3-Chloro-4-{4-[2-(2,4-dichloro-phenoxy)-ethylcarbamoyl]-5-methyl-isoxazol-3-yl}-phenyl)-acetic acid; (3-Chloro-4-{5-methyl-4-[2-(2-nitro-4-trifluoromethyl-phenoxy)-ethylcarbamoyl]-isoxazol-3-yl}-phenyl)-acetic acid; (4-{4-[2-(2,4-Bis-trifluoromethyl-phenoxy)-ethylcarbamoyl]-5-methyl-isoxazol-3-yl}-3-chloro-phenyl)-acetic acid; 2-(3-chloro-4-(5-cyclopropyl-4-(2-(2,4-dichlorophenoxy)ethylcarbamoyl)isoxazol-3-yl)phenyl)acetic acid; 2-(3-chloro-4-(4-(2-(2,4-dichlorophenoxy)ethylcarbamoyl)-5-isopropylisoxazol-3-yl)phenyl)acetic acid; 2-(3-chloro-4-(4-(2-(2,4-dichlorophenoxy)ethylcarbamoyl)-5-ethylisoxazol-3-yl)phenyl)acetic acid; 2-(4-(5-tert-butyl-4-(2-(2,4-dichlorophenoxy)ethylcarbamoyl)isoxazol-3-yl)-3-chlorophenyl)acetic acid; 2-(3-chloro-4-(4-(2-(2,4-dichlorophenoxy)ethylcarbamoyl)-5-(furan-2-yl)isoxazol-3-yl)phenyl)acetic acid; 2-(3-chloro-4-(4-(2-(2,4-dichlorophenoxy)ethylcarbamoyl)-5-(furan-3-yl)isoxazol-3-yl)phenyl)acetic acid; 2-(3-(4-(2-(2,4-dichlorophenoxy)ethylcarbamoyl)-5-(furan-2-yl)isoxazol-3-yl)phenyl)acetic acid; 2-(3-(5-cyclopropyl-4-(2-(2,4-dichlorophenoxy)ethylcarbamoyl)isoxazol-3-yl)phenyl)acetic acid; 2-(3-(4-(2-(2,4-dichlorophenoxy)ethylcarbamoyl)-5-methylisoxazol-3-yl)phenyl)acetic acid; 2-(3-(4-(2-(2,4-dichlorophenoxy)ethylcarbamoyl)-5-methylisoxazol-3-yl)phenyl)acetic acid; 2-(3-(4-(2-(2,4-dichlorophenoxy)ethylcarbamoyl)-5-propyl-isoxazol-3-yl)phenyl)acetic acid; 2-(3-(4-(2-(2,4-dichlorophenoxy)ethylcarbamoyl)-5-isopropylisoxazol-3-yl)phenyl)acetic acid; 2-(3-(5-tert-butyl-4-(2-(2,4-dichlorophenoxy)ethylcarbamoyl)isoxazol-3-yl)phenyl)acetic acid; 2-(3-(4-(2-(2,4-dichlorophenoxy)ethylcarbamoyl)-5-(furan-3-yl)isoxazol-3-yl)phenyl)acetic acid; 2-(3-(4-(2-(2,4-dichlorophenoxy)ethylcarbamoyl)-5-(pyridin-2-yl)isoxazol-3-yl)phenyl)acetic acid; 2-(3-(4-(2-(2,4-dichlorophenoxy)ethylcarbamoyl)-5-(pyridin-3-yl)isoxazol-3-yl)phenyl)acetic acid; 2-(3-(4-(2-(2,4-dichlorophenoxy)ethylcarbamoyl)-5-(pyridin-4-yl)isoxazol-3-yl)phenyl)acetic acid; and 2-(3-(4-(2-(2,4-dichlorophenoxy)ethylcarbamoyl)-5-(thiophen-2-yl)isoxazol-3-yl)phenyl)acetic acid.

7. A compound selected from 3-(2,6-Dichloro-phenyl)-5-methyl-4-[2-(2-nitro-4-trifluoromethyl-phenoxy)-ethoxymethyl]-isoxazole; (3-Chloro-4-{5-methyl-4-[2-(2-nitro-4-trifluoromethyl-phenoxy)-ethoxymethyl]-isoxazol-3-yl}-phenyl)-acetic acid; {3-Chloro-4-[5-methyl-4-(2-nitro-4-trifluoromethyl-phenoxymethyl)-isoxazol-3-yl]-phenyl}-acetic acid; (3-Chloro-4-{4-[2-(2,4-dichloro-phenoxy)-ethoxymethyl]-5-phenyl-isoxazol-3-yl}-phenyl)-acetic acid; and (3-Chloro-4-{4-[4-(2,4-dichloro-phenoxy)-butyryl]-5-phenyl-isoxazol-3-yl}-phenyl)-acetic acid.

* * * * *